(12) United States Patent
Bouvier et al.

(10) Patent No.: US 9,029,097 B2
(45) Date of Patent: May 12, 2015

(54) BIOSENSORS FOR MONITORING RECEPTOR-MEDIATED G-PROTEIN ACTIVATION

(75) Inventors: Michel Bouvier, Montreal (CA); Céline Gales, Toulouse (FR); Billy Breton, Montreal (CA)

(73) Assignee: Universite de Montreal, Montreal, Quebec (CA)

( * ) Notice: Subject to any disclaimer, the term of this patent is extended or adjusted under 35 U.S.C. 154(b) by 1880 days.

(21) Appl. No.: 11/816,517

(22) PCT Filed: Feb. 16, 2006

(86) PCT No.: PCT/CA2006/000233
§ 371 (c)(1),
(2), (4) Date: Apr. 3, 2008

(87) PCT Pub. No.: WO2006/086883
PCT Pub. Date: Aug. 24, 2006

(65) Prior Publication Data
US 2009/0298162 A1 Dec. 3, 2009

Related U.S. Application Data

(60) Provisional application No. 60/653,126, filed on Feb. 16, 2005.

(51) Int. Cl.
*C12Q 1/66* (2006.01)
*G01N 33/74* (2006.01)
*G01N 21/64* (2006.01)
*G01N 33/542* (2006.01)

(52) U.S. Cl.
CPC .............. *G01N 33/74* (2013.01); *G01N 21/6428* (2013.01); *G01N 33/542* (2013.01); *G01N 2333/726* (2013.01); *G01N 2500/00* (2013.01)

(58) Field of Classification Search
None
See application file for complete search history.

(56) References Cited

U.S. PATENT DOCUMENTS

| 7,932,080 | B2 * | 4/2011 | Bouvier et al. | ............ | 435/287.1 |
| 2009/0298162 | A1 * | 12/2009 | Bouvier et al. | ............ | 435/288.7 |

FOREIGN PATENT DOCUMENTS

CA 2335305 A1 12/1999

OTHER PUBLICATIONS

Milligan (Euro. J. of Pharm. Sci, vol. 21, Iss.4, Mar. 2004, pp. 397-405).*
Wells, Biochemistry, vol. 29, pp. 8509-8517, 1990.*
Heim et al. (PNAs, vol. 91, pp. 12501-12504, 1994).*
Dacres et al. (Biochem & Biophys Res Comm., vol. 425, 2012, pp. 625-629.*
Kosteinis et al. (Circulation, 2005, vol. 111, pp. 1806-1813).*
Kocan et al. (Frontiers in Endocrin. Jan. 2011, 1-8).*
Gales et al. (Nature Methods, 2005, vol. 2, No. 3, pp. 177-184).*
McVey et al. (JBC, vo. 276, 2001, pp. 14092-14099).*
Pfleger et al. (Biochem J. Immediate Publ., 2004, pp. 1-43).*
Milligan et al. (Life Sciences, vol. 74, 2003, pp. 181-188).*
Salahpour et al. (Frontiers in Endocrin., Aug. 2012, pp. 1-9).*
Barak et al. (JBC, vol. 272, No. 44, 1997, pp. 27497-27500).*
Conway et al. (Receptors & Channels, vol. 8, No. 5-6, pp. 331-341, 2002).*
Barak et al. (JBC, vol. 272, pp. 27497-27500, 1997).*
Charest et al. (EMBO reports, vol. 6, pp. 334-340, 2005).*
Subramanian et al. (The Plant Journal, 2006, vol. 48, pp. 138-152).*
Xu, Yao, et al., "A Bioluminescense Resonance Energy Transfer (BRET) System: Application to Interacting Circadian Clock Proteins", Proc. Natl. Acad. Sci., USA, vol. 96, pp. 151-156, Jan. 1999.
Gales, Celine, et al., "Real Time Assessment of GPCRs Activation-Deactivation Cycle in Living Cells Using Bioluminescense Resonance Energy Transfer (BRET)", IUBMB/ASBMB 2004: Meeting Abstracts.
Gilman, A.G., "G Proteins: Transducers of Receptor-Generated Signals", Annu. Rev. Biochem., 56, 615-649 (1987).
Bourne, H.R., "How Receptors Talk to Trimeric G Proteins", Curr. Opin. Cell Biol., 9, 134-142 (1997).
Cabrera-Vera, T.M., et al., "Insights into G Protein Structure, Function, and Regulation", Endocr. Rev., 24, 765-781 (2003).
Rebois, R.V., et al., "Does Subunit Dissociation Necessarily Accompany the Activation of all Heterotrimeric G Proteins?", Cell Signal., 9, 141-151 (1997).
Klein, S., et al., "Signal Transduction by a Nondissociable Heterotrimeric Yeast G Protein", Proc. Natl. Acad. Sci. U.S.A., 97, 3219-3223 (2000).
Bunemann, M., et al., "Gi Protein Activation in Intact Cells Involves Subunit Rearrangement Rather than Dissociation", Proc. Natl. Acad. Sci. U.S.A, 100, 16077-16802 (2003).
Frank, M., et al. "G Protein Activation without Subunit Dissociation Depends on a G{alpha}(i)-Specific Region", J. Biol. Chem., 280, 24585-24590 (2005).
Gales, C., et al., "Real-Time Monitoring of Receptor and G-Protein Interactions in Living Cells", Nat. Methods, 2, 177-184 (2005).

(Continued)

*Primary Examiner* — Hope Robinson
(74) *Attorney, Agent, or Firm* — Sheridan Law, LLC

(57) ABSTRACT

The present invention relates to novel biosensors that are based on bioluminescence resonance energy transfer (BRET). These biosensors may be used to monitor rapid interaction and conformational changes within G protein-coupled receptor/G protein complexes and, in this way, reflect the activation status of the receptor. Advantageously, the biosensors may be used as a highly sensitive and quantitative assay for the identification of ligands (agonists, antagonists, inverse agonists, partial agonists, etc.) targeting G protein-coupled receptors (GPCRs) as well as for the analysis of the activation status of these receptors. Moreover, multiplexing different biosensors within receptors/G protein complexes allows for mapping ligand textures. Additionally, the biosensors permit the direct, real-time examination of interactions between receptors and G protein in their natural environment, the living cell.

29 Claims, 53 Drawing Sheets

(56) References Cited

OTHER PUBLICATIONS

Sprang, S.R., "G Protein Mechanisms: Insights frm Structural Analysis", Annu. Rev. Biochem., 66, 639-678 (1997).
Noel, J.P., et al., "The 2.2 A Crystal Structure of Transducin-Alpha Complexed with GTP Gamma S", Nature, 366, 654-663 (1993).
Sondek, J., et al., "GTPase Mechanism of Gproteins from the 1.7-A Crystal Structure of Transducin Alpha-GDP-AIF-4", Nature, 372, 276-279 (1994).
Cherfils, J., et al., "Activation of G-Protein Galpha Subunits by Receptors through Galpha-Gbeta and Galpha-Ggamma interactions", Trends Biochem. Sci., 28, 13-17 (2003).
Ceruso, Ma, et al., "Molecular Dynamics Simulations of Transducin: Interdomain and Front to Back Communication in Activation and Nucleotide Exchange", J. Mol. Bio., 338, 469-481 (2004).
Rondard, P., et al., "Mutant G Protein Alpha Subunit Activited by Gbeta Gamma: A Model for Receptor Activation?", Proc. Natl. Acad. Sci. U.S.A., 98, 6150-6155 (2001).
Iiri, T., et al., "G-Protein Diseases Furnish a Model for the Turn-On Switch", Nature, 394, 35-38 (1998).
Pfleger, K.D., et al., "Monitoring the Formation of Dynamic G-Protein-Coupled Receptor-Protein Complexes in Living Cells", Biochem. J., 385, 625-637 (2005).
Miyawaki, A., "Visualization of the Spatial and Temporal Dynamics of Intracellular Signaling", Dev. Cell, 4, 295-305 (2003).
Tateyama, M., et al., "Ligand-Induced Rearrangement of the Dimeric Metabotropic Glutamate Receptor 1Alpha", Nat. Struct. Mol. Bio., 11, 637-642 (2004).
Vilardaga, J.P., et al., "Measurement of the Millisecond Activation Switch of G Protein-Coupled Receptors in Living Cells", Nat. Biotechnol, 21, 807-812 (2003).
Charest, P.G., et al., Monitoring Agonist-Promoted Conformational Changes of Beta-Arrestin in Living Cells by Intramolecular, BRET. EMBO, Re., 6, 334-340 (2005).
Schaufele, F., et al., "The Structural Basis of Androgen Receptor Activation: Intramolecular and Intermolecular Amino-Carboxy Interactions", Proc. Natl. Acad. Sci. U.S.A., 102, 9802-9807 (2005).
Tsuboi, T., et al., "ATP-Dependent InteraCtion of the Cytosolic Domains of the Inwardly Rectifying K+ Channel Kir6.2 Revealed by Fluorescence Resonance Energy Transfer", Proc. Natl. Acad. Sci. U.S.A., 101, 76-81 (2004).
Mercier, J.F., et al., "Quantitive Assessment of Beta 1- and Beta 2-Adrenergic Receptor Homo- and Heterodimerization by Bioluminescense Resonance Energy Transfer", J. Biol. Chem., 277, 44925-44931 (2002).
Ramsay, D., et al., "High-Affinity Interactions Between Human Alpha1A-Adrenoceptor C-Terminal Splice Variants Product Homo- and Heterodimers But Do Not Generate the Alpha1L-Adrenoceptor", Mol. Pharmacol., 66, 228-239 (2004).
Oakley, R.H., et al., "Molecular Determinants Underlying the Formation of Stable Intracellular G Protein-Coupled Receptor-Beta-Arrestin Complexes After Receptor Endocytosis", J. Biol. Chem., 276, 19452-19480 (2001).
Perroy, J., et al., "Real-Time Monitoring of Ubiquitination in Living Cells by BRET", Nat. Methods, 1, 203-208 (2004).
Rebois, R.V., et al., "Protein Complexes Involved in Heptahelical Receptor-Mediated Signal Transduction", Receptor Channels, 9, 169-194 (2003).
Neubig, R. R., "Membrane Organization in G-Protein Mechanisms", FASEB J., 8, 939-946 (1994).
Fanelli, F., et al., "Rhodopsin Activation Follows Precoupling with Transducin: Inferences from Computational Analysis (,)", Biochemistry, 44, 14695-14700 (2005).
Janetopoulos, C., et al., "Receptor-Mediated Activation of heterotrimeric G-Proteins in Living Cells", Science, 291, 2408-2411 (2001).
Yi, T.M., et al., "A Quantitive Characterization of the Yeast Heterotrimeric G Protein Cycle", Proc. Natl. Acad. Sci. U.S.A. 100, 10764-10769 (2003).

Wall, M.A., et al., "The Structure of the G Protein Heterotrimer GI Alpha 1 Beta 1 Gamma 2", Cell, 83, 1047-1058 (1995).
Kenakin, T., "Llgand-Selective Receptor Conformations Revisited: The Promise and the Problem", Trends Pharmacol. Sci., 24, 346-354 (2003).
Kenakin, T., "New Concepts in Drug Discovery: Collateral Efficacy and Permissive Antagonism", Nat. Rev. Drug Discov., 4, 919-927 (2006).
Nagai, T., et al., "A Variant of Yellow Flourescent Protein with Fast and Efficient Maturation for Cell-Biological Applications", Nat. Biotechnol., 20, 87-90 (2002).
Milligan, G., "Applications of Bioluminescense and Fluorescense Resonance Energy Transfer to Drug Discovery at G Protein-Coupled Receptors", Eur. J. Pharm. Sci., 21, 397-405 (2004).
Gales, C., et al., "Mutation of Asn-391 Within the Conserved NPSSY Motif of the Cholecystokinin B Receptor Abolishes GQ Protein Activation without Affecting Its Association with the Receptor", J. Biol. Chem., 275, 17321-17327 (2000).
Krieger, E., et al., "Increasing the Precision of Comparative Models with Yasara Nova—A Self Parameterizing Force Field", Proteins, 47, 393-402 (2002).
Weng, G., et al., "Structural Basis for the Function of the Heterotrimeric G-Proteins", Seminars in Neuroscience, 9, 175-188. (1998).
Bockaert, J., et al., "G Protein-Coupled Receptors: Dominant Players in Cell-Cell Communication", Int. Rev. Cytol., 212, 63-132 (2002).
Bouvier, M., "Oligomerization of G-Protein-Coupled Transmitter Receptors", Nat. Rev. Neurosci., 2, 274-286 (2001).
Angers, S., et al., "Detection of Beta 2-Adrenergic Receptor Dimerization in Living Cells Using Bioluminescense Resonance Energy Transfer (BRET)", Proc. Natl. Acad. Sci. U. S.A., 97, 3684-3689 (2000).
Yu, J.Z., et al., "Real-time Visualization of a Fluorescent G(alpha)(s): Dissociation of the Activated G Protein from Plasma Membrane", Mol. Pharmacol., 61, 352-359 (2002).
Ruiz-Velasco, V., et al., "Functional Expression and FRET Analysis of Green Gluorescent Proteins Fused to G-Protein Subunits in Rat Sympathetic Neurons", J. Physio, 537, 679-692 (2001).
Evanko, D.S., at al., "Gbeta Gamma Isoforms Selectively Rescue Plasma Membrane Localization and Palmitoylation of Mutatnt Galphas and Galphaq", J.Biol. Chem., 276, 23945-23953 (2001).
Wenzel-Seifert, K., et al., "Molecular Analysis of Beta(2)-Adrenoceptor Coupling to G(s)-, G(i)-, and G(q)-proteins", Mol. Pharma., col. 58, 954-966 (2000).
Huang, J.S., et al., "Cell Signaling Through Thromboxane A2 Receptor", Cell Signal., 16, 521-533 (2004).
Kinsella, B.T., "Thromboxane A2 Signaling in Humans: A 'Tail' of Two Receptors", Biochem. Soc. Trans., 29, 641-654 (2001).
Crespo, P., et al., "Duel Effect of Beta-Adrenergic Receptors on Mitogenactivated Protein Kinase. Evidence for a Beta Gamma-Dependent Activation and a G Alpha S-Campmediated Inhibition". J. Biol. Chem., 270, 25259-25265 (1995).
Chung, F.Z., et al., "Site-Directed Mutagenesis and Continuous Expression of Human Beta-Adrenergic Receptors. Identification of a Conserved Aspartate Residue Involved in Agonist Binding and Receptor Activation", J. biol. Chem., 263, 4052-4055 (1968).
Chidiac, P., et al., "Agonist-Induced Modulation of Inverse Agonist Efficacy at the Beta 2-Adrenergic Receptor", Mol. Pharmacol., 50, 662-669 (1996).
Levitzki, A., et al., "G-Protein Subunit Dissociation is Not an Integral Part of G-Protein Action". Chembiochem., 3, 815-818 (2002).
Jones, S.B., et al., "Desensitization of the Alpha-2 Adrenergic Receptor in HT29 and Opossum Kidney Cell Lines", J. Pharmacol. Exp. Ther., 254, 294-300 (1990).
Benovic, J.L., et al., "Regulation of Adenylyl Cyclase-Coupled Betaadrenergic Receptors", Annu. Rev. Cell Biol, 4, 405-428 (1988).
Clark, W.A., et al., "Independent and Synergistic Interaction of Retinal G-Protein Subunits with Bovine Rhodopsin Measured by Surface Plasmon Resonance", Biochem. J., 358, 389-397 (2001).
Waller, A., et al. "Techniques: GPCR Assembly, Pharmacology and Screening by Flow Cytometry", Trends Pharmacol. Sci., 25, 663-669 (2004).

(56) References Cited

OTHER PUBLICATIONS

Albert, P.R., et al., "G Protein Specificity: Traffic Direction Required", Cell Signal., 14, 407-418 (2002).

Bertrand, L., et al., "The BRET2/Arrestin Assay in Stable Recombinant Cells: A Platform to Screen for Compounds that Interact with G Protein-Coupled Receptors (GPCRS)", J. Recept. Signal. Transduct. Res., 22, 533-541 (2002).

Perroy, J., et al., "Phosphorylation-Independent Desensitization of GABA(B) Receptor by GRK4", EMBO J., 22, 3816-3824 (2003).

Morello, J.P., et al., "Pharmacological Chaperones Rescue Cell-Surface Expression and Function of Misfolded V2 Vasopressin Receptor Mutants", J. Clin. Invest, 105, 887-895 (2000).

Azzi, M. et al., "Allosteric Effects of G Protein Overexpression on the Binding of Beta-Adrenergic Ligands with Distinct Inverse Efficacies", Mol. Pharmacoi., 60, 999-1007 (2001).

\* cited by examiner

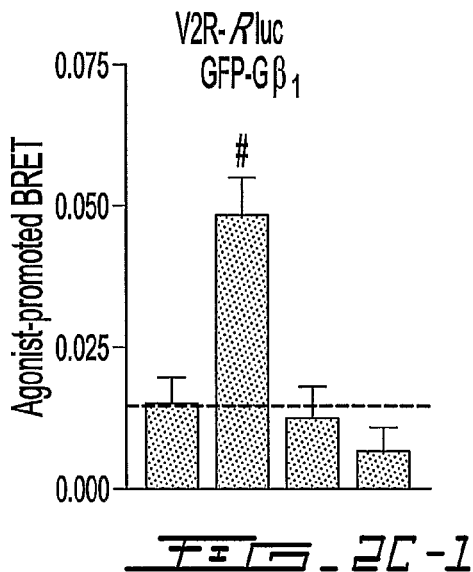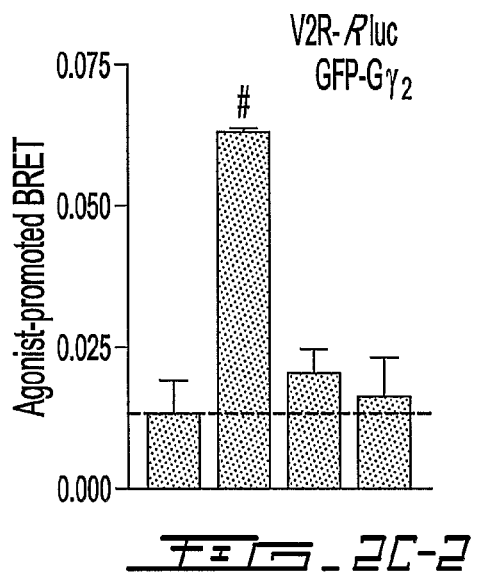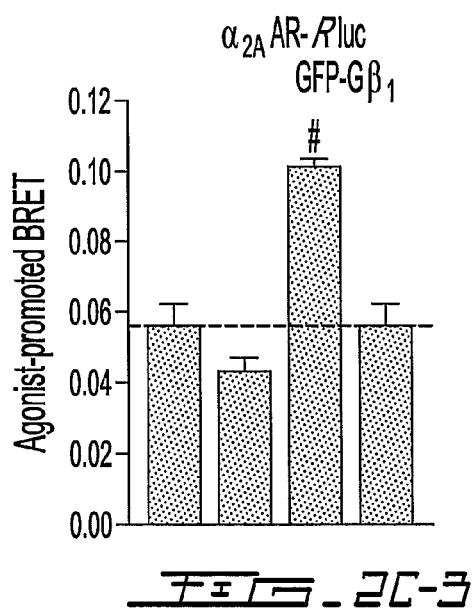

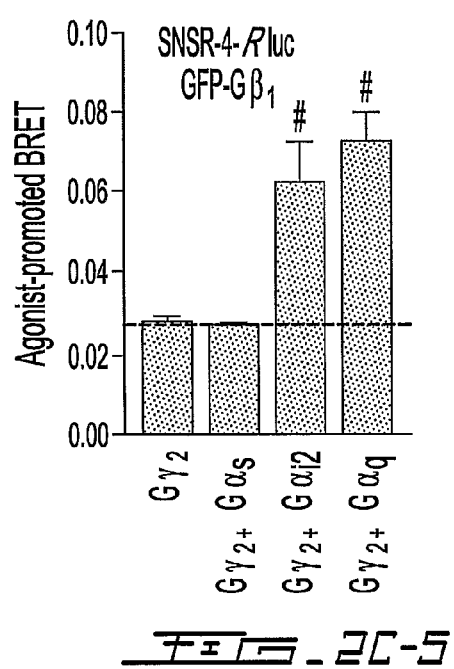
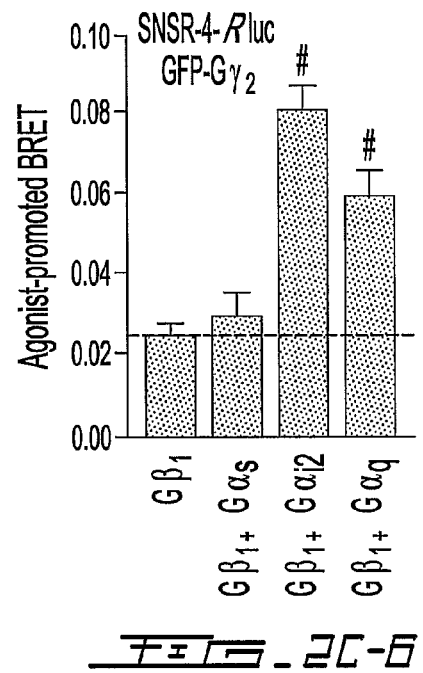
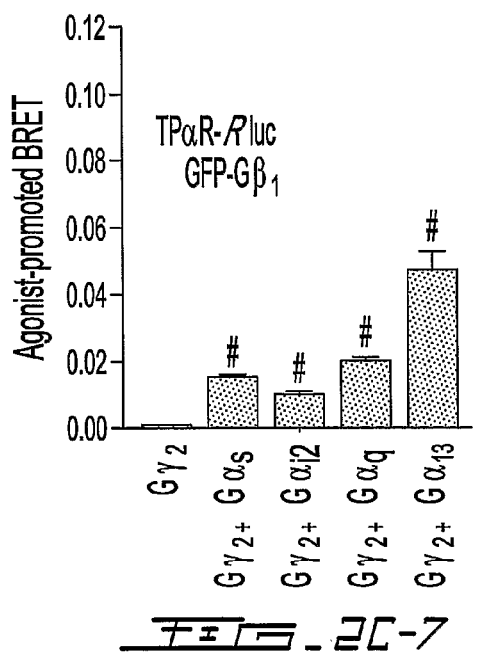
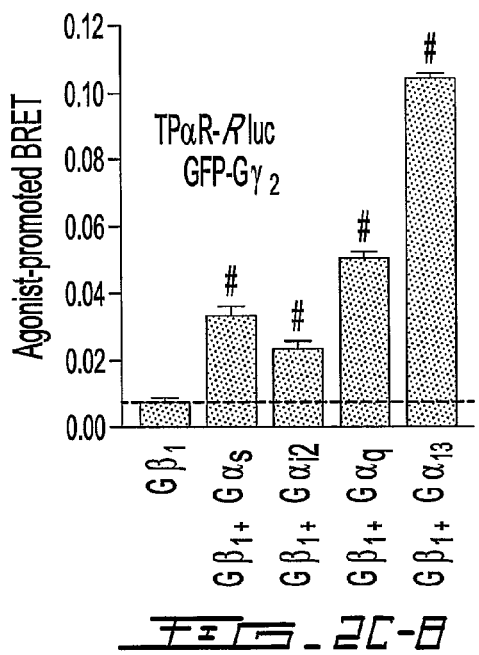

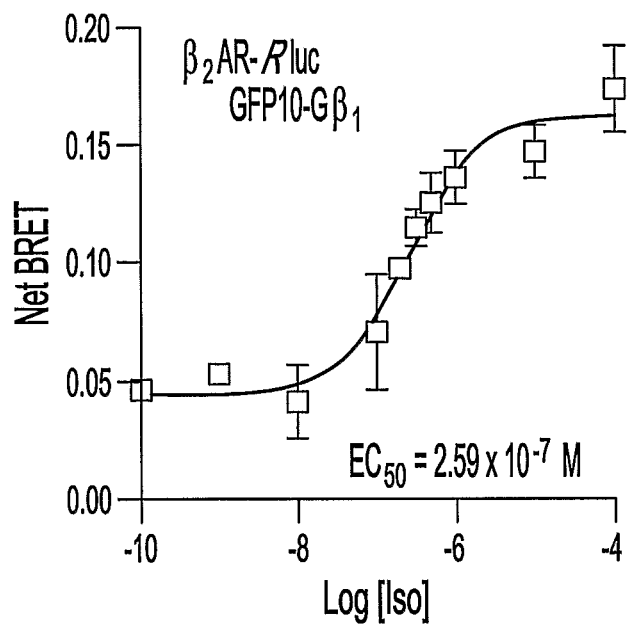
_FIG_3A-1_
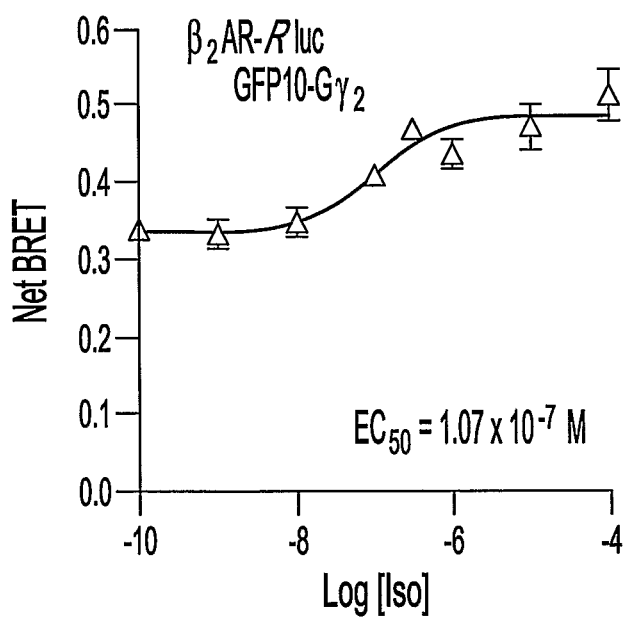
_FIG_3A-2_

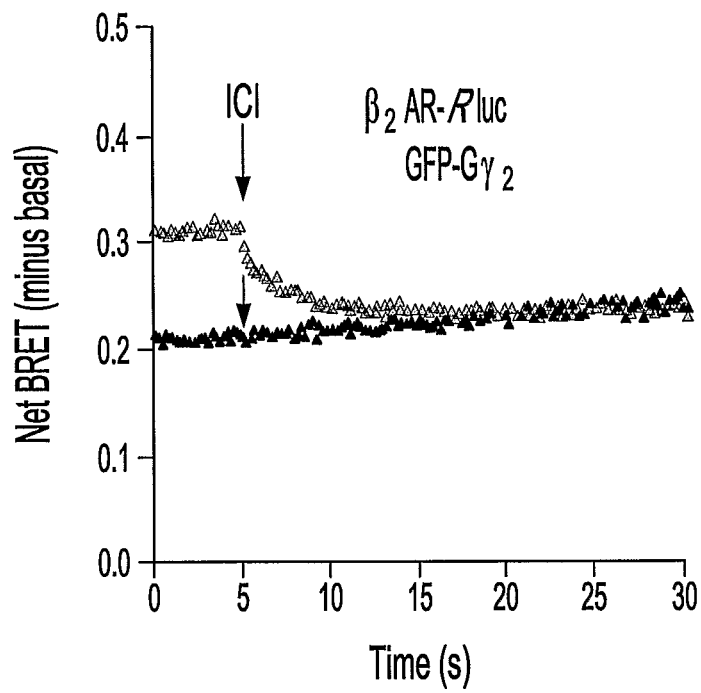
FIG_4B
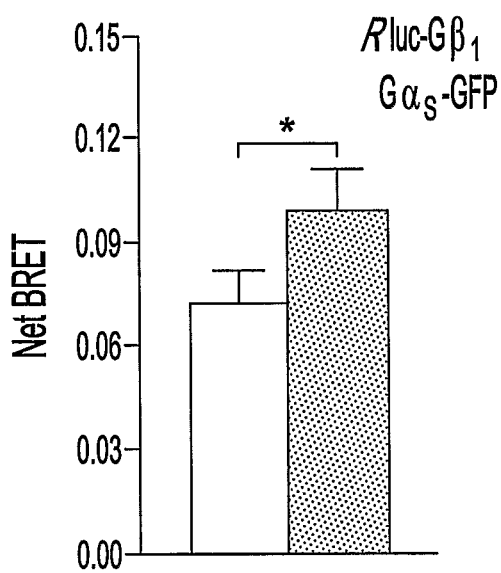
FIG_4C

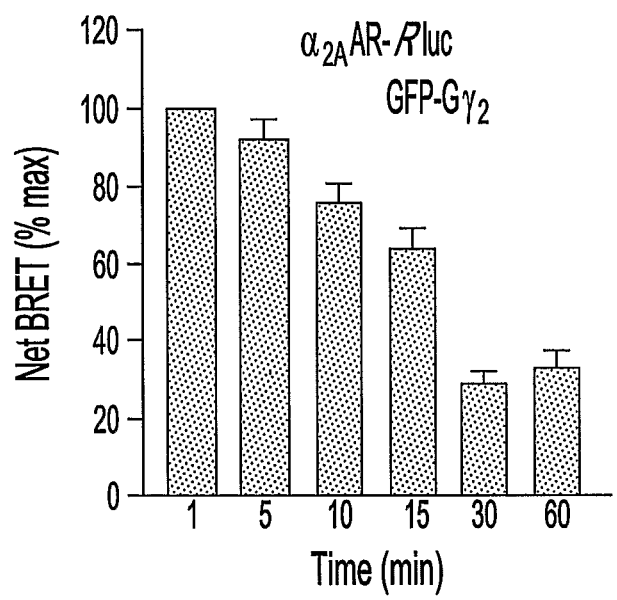
FIG_4F

HA-GBR2

CD8-*R*luc

HA-GBR2

$\beta_2$AR-*R*luc

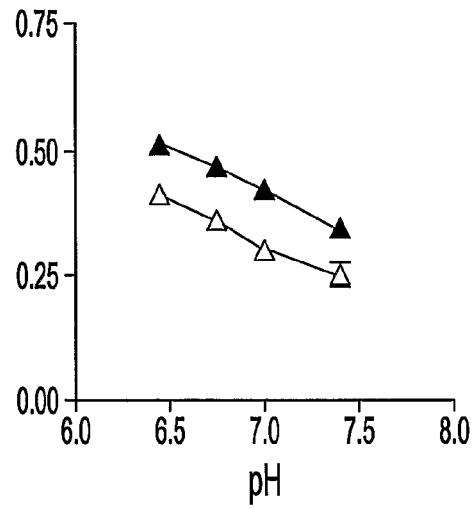
FIG_6
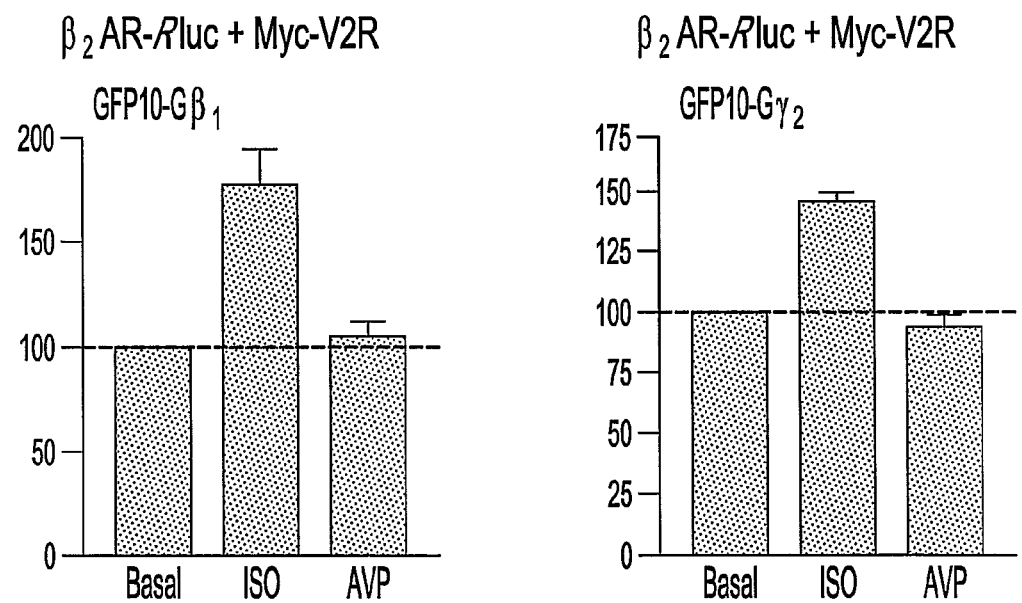
FIG_7-1
FIG_7-2

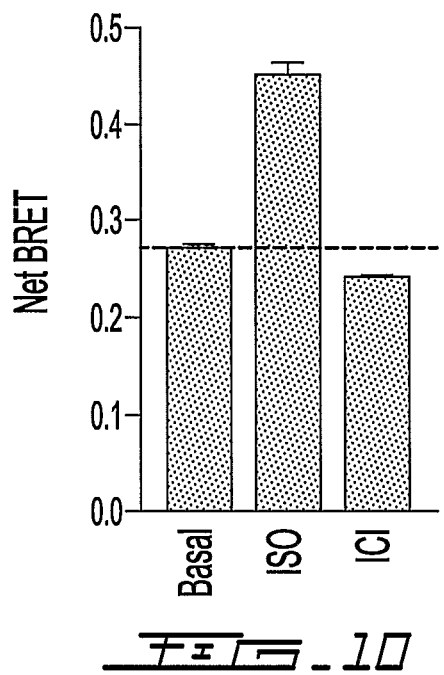
FIG_10
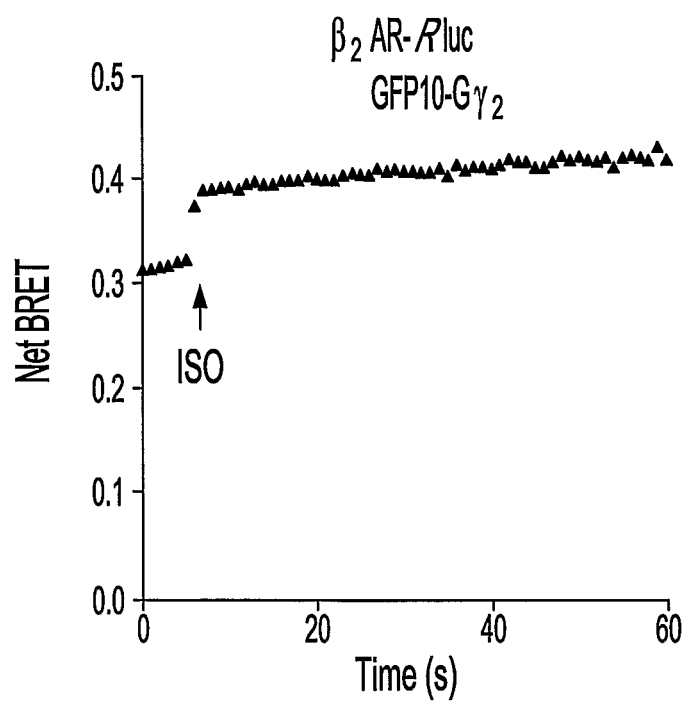
FIG_11

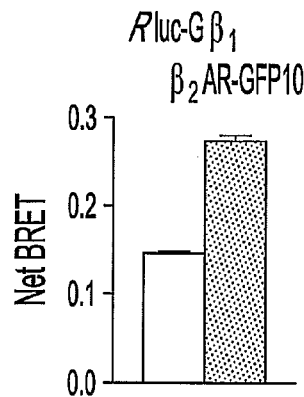
FIG. 14-1
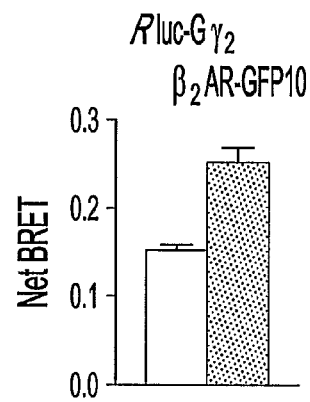
FIG. 14-2
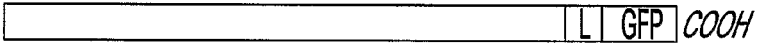
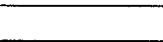
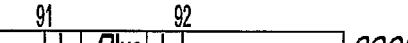
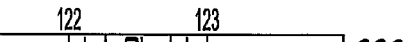
FIG. 15A

HA-GBR2

Gα$_{i1}$-91
Rluc

HA-GBR2

Gα$_{i1}$-122
Rluc

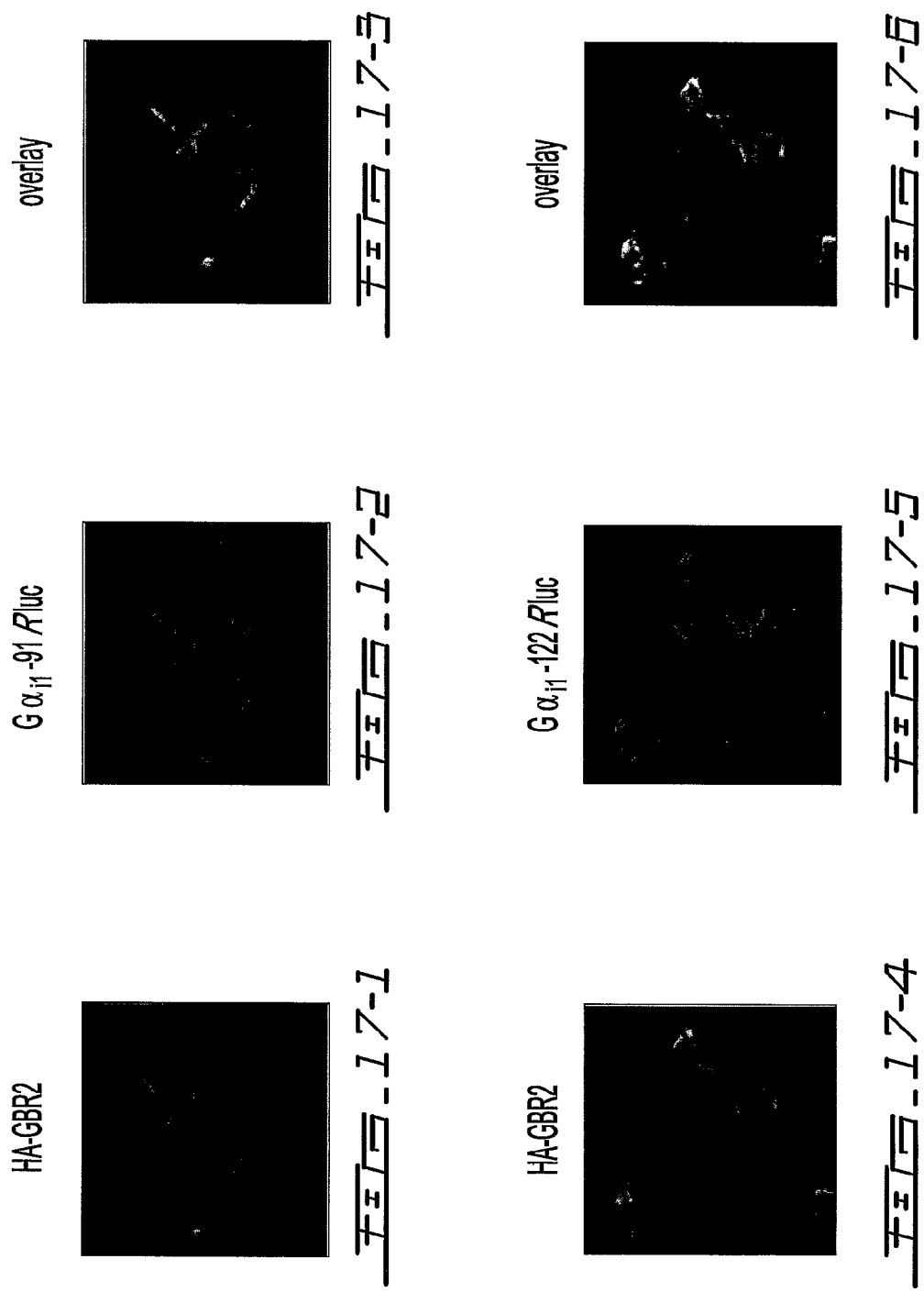

Receptor-Rluc / GFP-Gβ$_1$
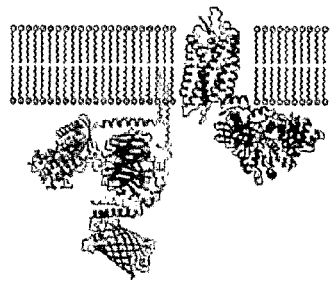
FIG_19A
Receptor-Rluc / GFP-Gγ$_2$
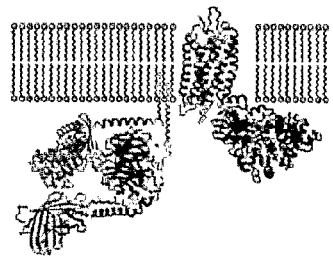
FIG_19B
Gα$_{i1}$-91 Rluc / receptor-GFP
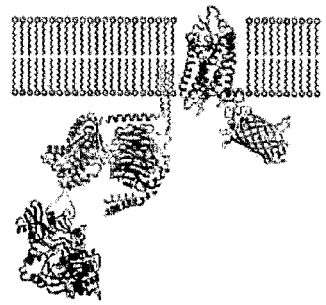
FIG_19C
Gα$_{i1}$-122 Rluc / receptor-GFP
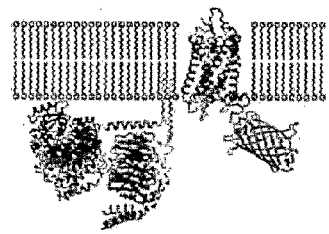
FIG_19D
Gα$_{i1}$-91 Rluc / GFPγ$_2$
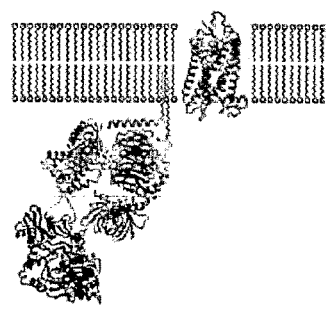
FIG_19E
Gα$_{i1}$-122 Rluc / GFP-Gγ$_2$
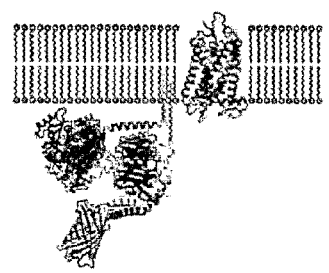
FIG_19F

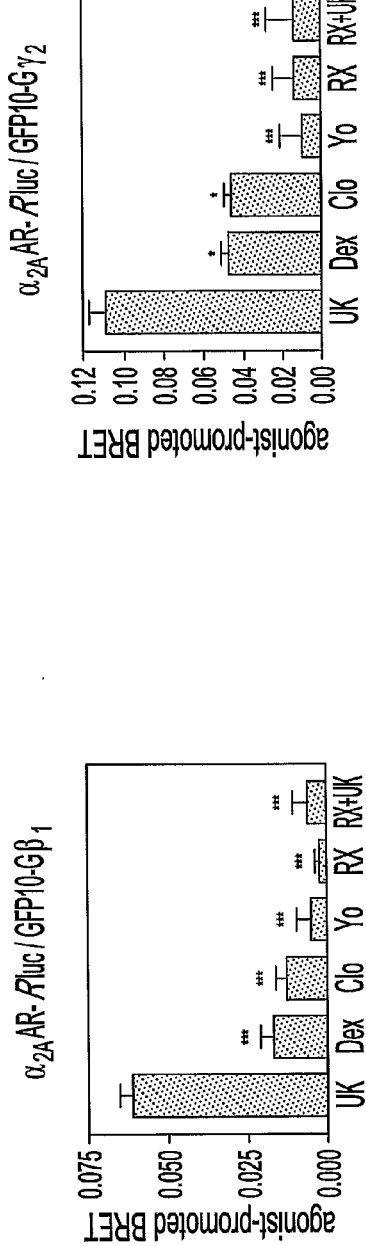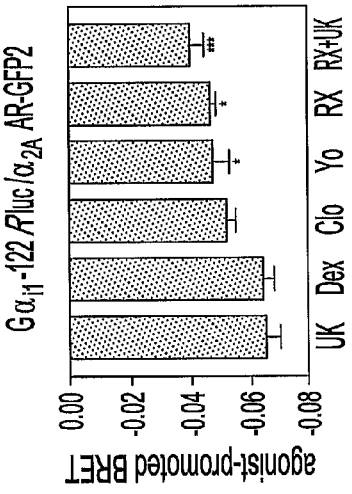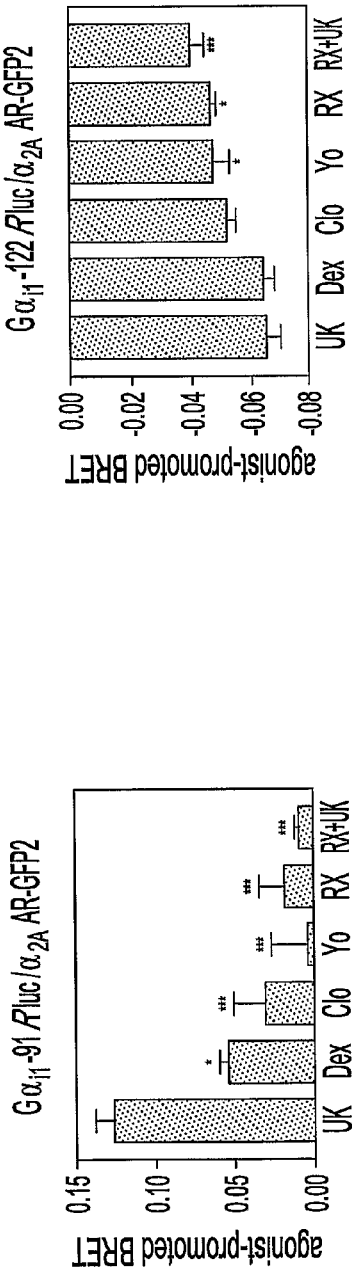
FIG. 25-1  FIG. 25-2  FIG. 25-3  FIG. 25-4

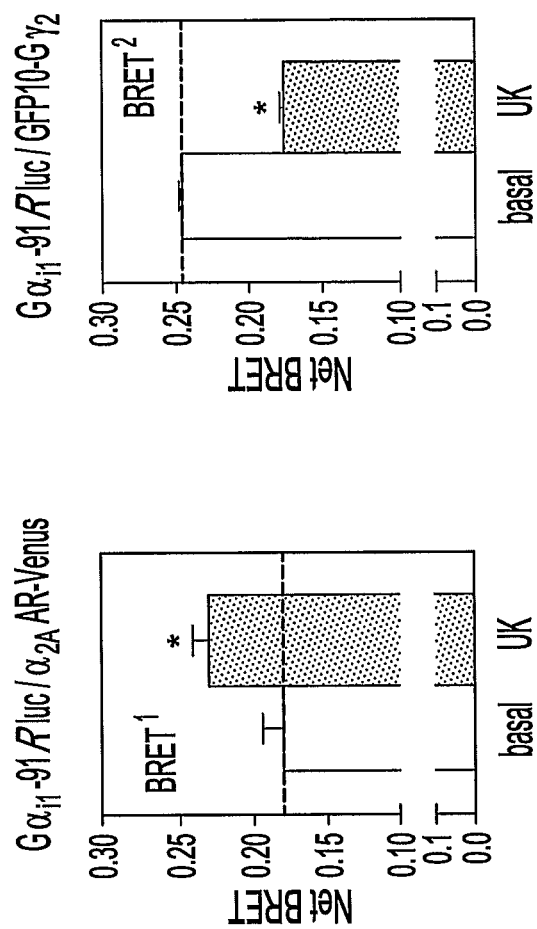
FIG. 27B-3
FIG. 27B-2
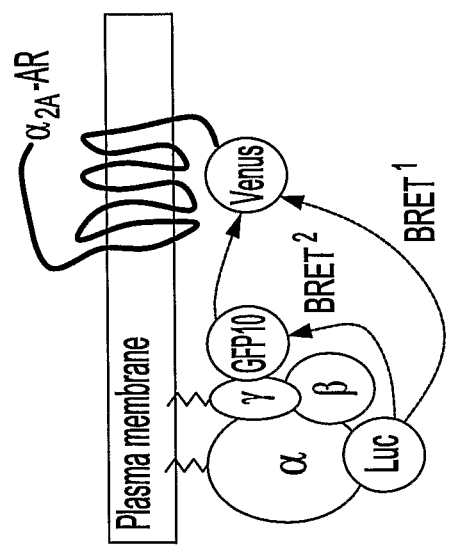
FIG. 27B-1

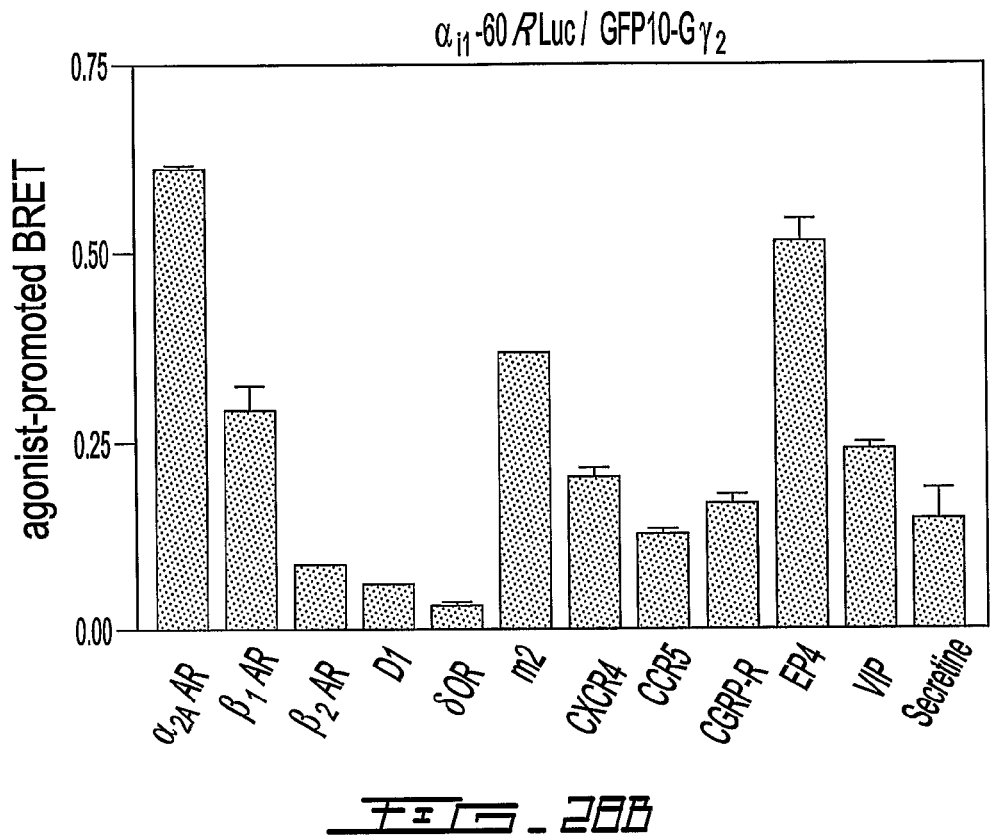
FIG_28B
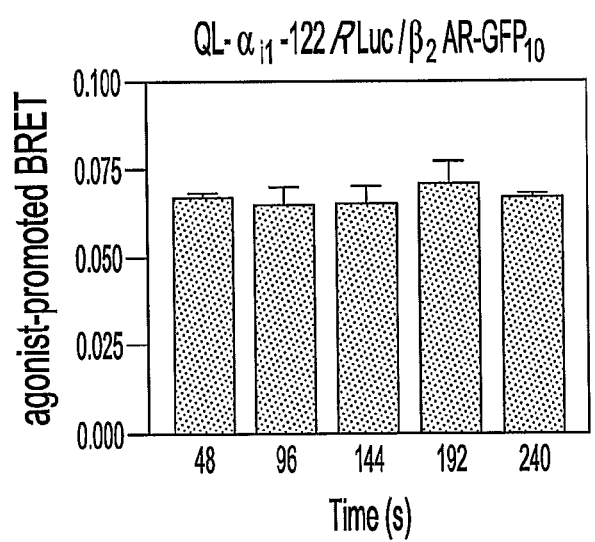
FIG_29

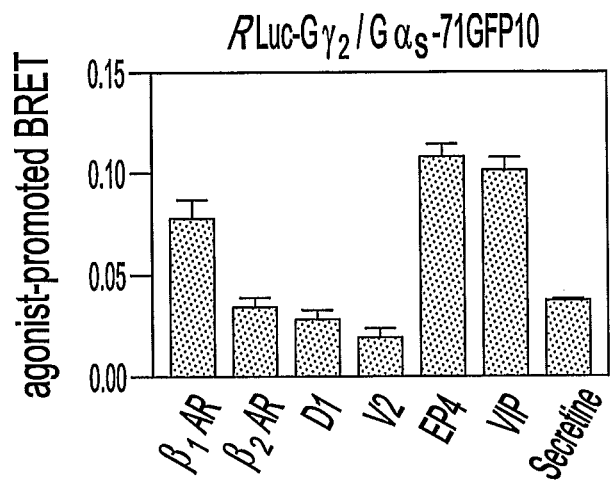
FIG_30
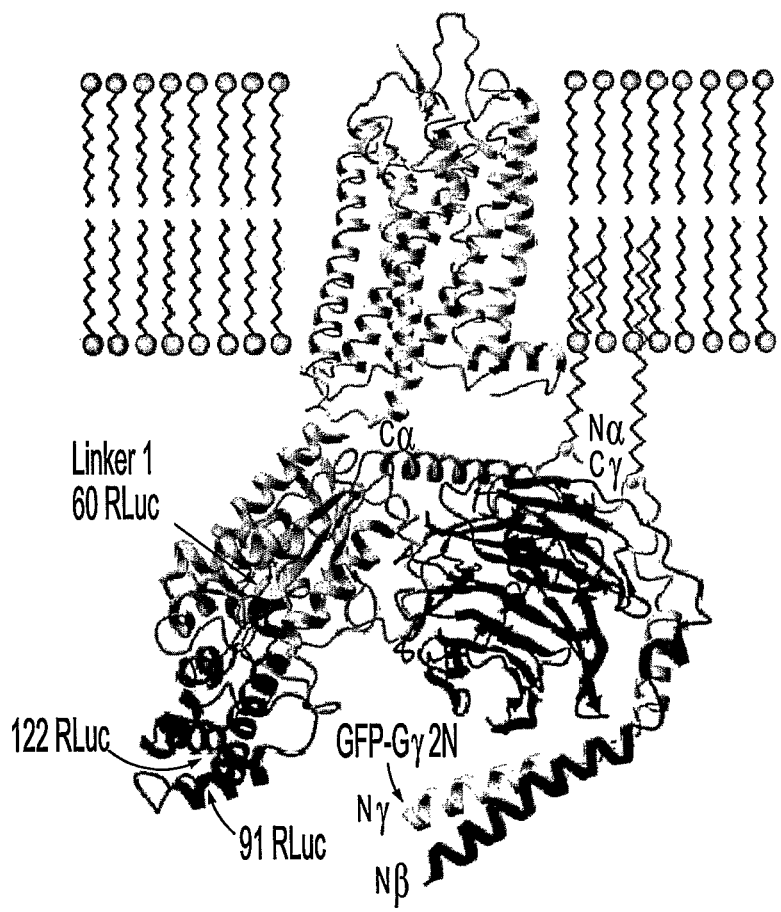
FIG_31A

BRET assay between receptor and G$\beta_1$ receptor-*R*luc / GFP-G$\beta_1$

BRET assay between receptor and G$\gamma_2$ receptor-*R*luc / GFP-G$\gamma_2$

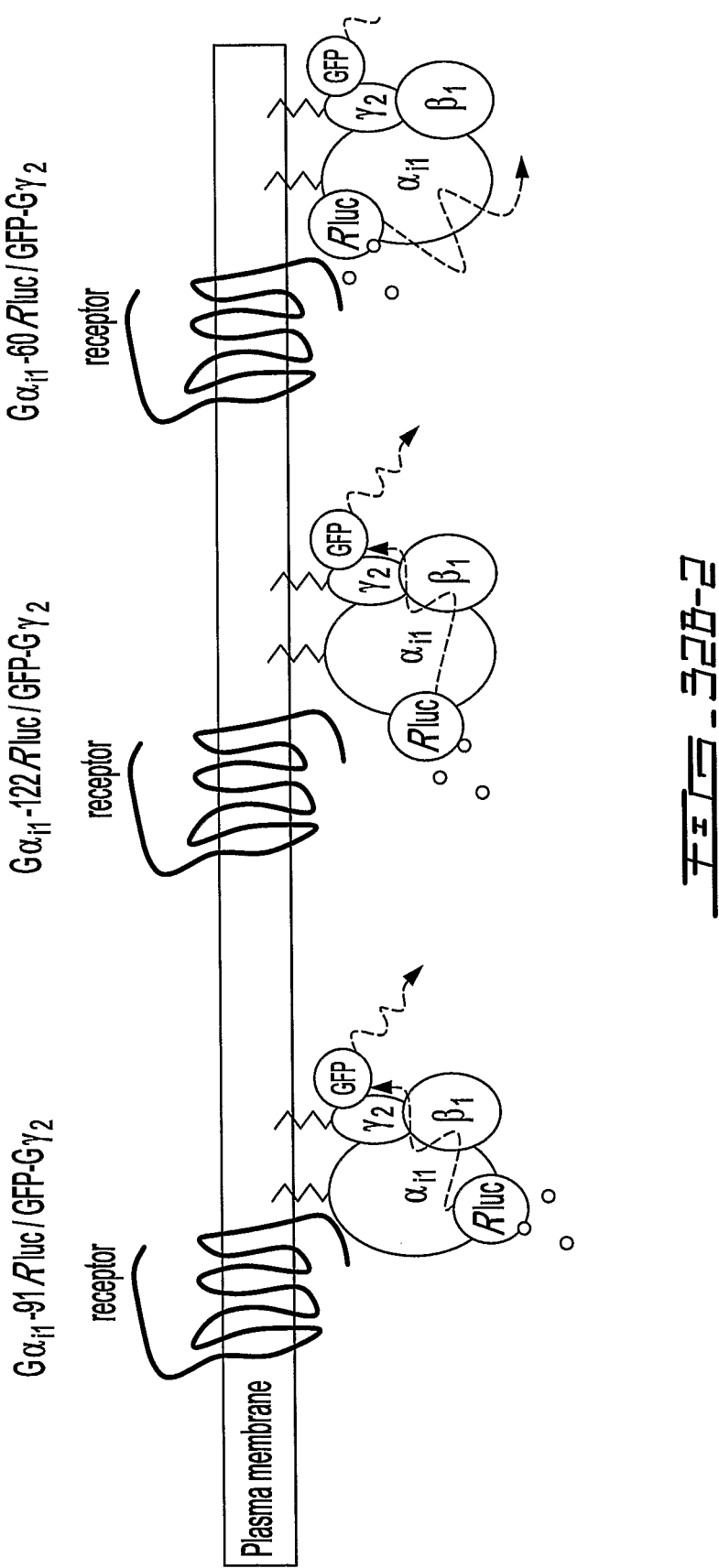

BIOSENSORS FOR MONITORING RECEPTOR-MEDIATED G-PROTEIN ACTIVATION

CROSS-REFERENCE TO RELATED APPLICATIONS

This application is a continuation of International Application No. PCT/CA2006/00233, filed Feb. 16, 2006, which claims priority from U.S. Provisional Application No. 60/653,126, filed on Feb. 16, 2005, both of which are hereby incorporated herein by reference.

FIELD OF THE INVENTION

The present invention relates to novel biosensors. Specifically, the invention relates to biosensors that are based on bioluminescence resonance energy transfer (BRET). These biosensors may be used to monitor rapid interaction and conformational changes within G protein-coupled receptor/G protein complexes and, in this way, reflect the activation status of the receptor. Advantageously, the biosensors may be used as a highly sensitive and quantitative assay for the identification of ligands (agonists, antagonists, inverse agonists, partial agonists, etc.) targeting G protein-coupled receptors (GPCRs) as well as for the analysis of the activation status of these receptors. Moreover, multiplexing different biosensors within receptors/G protein complexes allows for mapping ligand textures. Additionally, the biosensors permit the direct, real-time examination of interactions between receptors and G protein in their natural environment, the living cell.

BACKGROUND OF THE INVENTION

G-protein-coupled-receptors (GPCRs) also known as 7 transmembrane receptors (7TM) represent the largest family of cell surface receptors involved in signal transduction across biological membranes. They control a large diversity of physiological processes including vision, taste, olfaction, neuronal and hormonal transmission, cell growth and metabolism. Consequently, these receptors are important targets for the development of drugs with wide clinical applications. In recent years, increased knowledge about GPCR has facilitated the development and screening of many new therapeutically active molecules. However, our knowledge concerning the molecular events determining receptor signaling efficacy remains rudimentary.

Although recent advances in cellular biology have led to the identification of a broad range of proteins directly interacting with GPCRs[1], coupling with $\alpha\beta\gamma$ trimeric G proteins remains the common benchmark of all GPCR family members. Thus, these proteins constitute one of the most important and earlier plasma membrane transducers relaying information from activated cell surface GPCRs to intracellular signaling molecules. It is usually admitted that agonist binding promotes or stabilizes specific conformational states of the receptors that favor the engagement of the $G\alpha\beta\gamma$ complex by specific receptor domains. The ensuing exchange of guanosine diphosphate (GDP) for guanosine triphosphate (GTP) on the $G\alpha$ subunit is then believed to precipitate complex disassembly, leading to free GTP-bound $G\alpha$ and $G\beta\gamma$ subunits that can in turn interact and modulate downstream effectors. The termination of the signal results from the re-association of the holo-$G\alpha\beta\gamma$ inactive heterotrimer following GTP hydrolysis by the $G\alpha$ subunit[1-3]. However, this generally-accepted classical collision-based model, deduced largely from in vitro studies, has recently been challenged. Indeed, in vitro reconstitution assays[4], genetic studies in yeast[5] and resonance energy transfer studies carried out in living cells[6-8] have suggested that stable receptor/G protein and/or heterotrimeric G protein complexes may persist during the activation process. Information about these putative complexes and the structural rearrangement underlying their activation remain however rudimentary.

Resolution of crystal structures for active (GTP- or GTP$\gamma$S-bound), inactive (GDP-bound) and transition states (GDP-AlF$_4^-$ bound) of several $G\alpha$ subunits and of the inactive form of the $G\alpha_{i1}\beta_1\gamma_2$ and $G\alpha_t\beta\gamma_t$ heterotrimeric complexes has provided an initial basis for understanding the structural rearrangements involved in G protein activation[9]. However, the structural differences between active and inactive conformers are relatively modest, involving only local differences in the switch I, switch II and switch III regions that play key roles in guanine nucleotide exchange[10, 11]. Although models of activation have been proposed based on these three dimensional crystal structures, on analogy with the small G proteins[12, 13] and on site-directed mutagenesis studies or natural mutations found in diseases[2, 3, 14, 15], the static nature of the crystals and the absence of information about the empty state of $G\alpha$ limit the understanding of the dynamic changes occurring during receptor-promoted G protein activation.

At present, no method permits the direct assessment of the real-time interactions between receptors and G protein in living cells. Such assays would be particularly relevant given that the dynamics of protein interactions can be influenced by multiple spatio-temporal factors that cannot be easily recreated using in vitro assays. They would also provide new tools to test the ability of compounds to modulate the early steps in the signaling pathway, thus facilitating the identification of potential drug candidates.

There is therefore a need for biosensors that will allow the determination or assessment of the early steps in GPCR signaling and that may also serve to identify new ligands (agonists, antagonists, reverse agonists, partial agonists, etc.) for these receptors with defined signaling efficacy.

The present invention seeks to meet this and related needs.

SUMMARY OF THE INVENTION

In recent years, fluorescence and bioluminescence resonance energy transfer approaches (FRET and BRET) have been increasingly used to study protein-protein interactions and appreciate dynamic changes in protein conformation[16, 17]. The dependence of the energy transfer efficacy on the distance between energy donors and acceptors permits real time measurements that are both sensitive and specific to the labelling sites of the proteins thus allowing inference on the dynamic structural changes[18-22].

Taking advantage of multiple sites of energy donor and acceptor insertions in the protein-protein complex of interest, the present invention relies on the development of a BRET-based assay that directly monitors real-time interactions between GPCRs and their cognate G proteins and among the G protein subunits in living cells. In addition to monitor pre-assembled receptor/G protein complexes (reflected by basal BRET signal), the assay is capable of monitoring (as assessed by changes in the BRET signal detected in the assay) ligand-modulated interactions between receptor and G protein subunits (i.e., $G\alpha$, $G\beta$ and $G\gamma$ subunits) reflecting ligand-modulated G protein coupled receptor activation and G protein engagement as well as ligand-modulated interactions between G protein subunits reflecting G protein activation.

In addition, the invention provides a useful tool to probe for conformational changes occurring in the receptor/G protein complexes and G protein heterotrimer resulting from ligand binding to the receptor. As a result, by multiplexing different BRET-biosensors of the receptor/G protein or the G protein complex itself, the invention offers the possibility to set up pharmacological fingerprints that are specific to each receptor ligand, thus allowing to differentiate the distinct signalling modes of different ligand toward the various signalling pathways engaged.

Results demonstrate that GPCR fused to the energy donor *Renilla* luciferase (RLuc) and G protein subunits attached to a green fluorescent protein (YFP, GFP10 or GFP$^2$) energy acceptor or vice versa, provide reliable biosensors that can directly monitor the kinetic and selectivity of G protein engagement upon receptor activation. In addition to offering a new generally applicable method to probe dynamic protein interactions involved in G protein activation, the approach offers an advantageous tool to monitor the activation of distinct G protein subunits using a single assay mode. Receptor-mediated G protein activation can also be detected through a biosensor using the Gβ or Gγ subunits fused to RLuc and the Gα subunit fused to GFP10, GFP2 or YFP and/or vice versa, thus allowing to monitor interactions between Gα and Gβ or Gγ subunits fusion proteins as a result of activation of an untagged receptor. The data described herein provides direct kinetic measurement of the receptor-mediated activation of heterotrimeric G proteins in living cells, allowing the detection of both activation and desensitization events.

Due to its sensitivity and applicability for all major classes of Gα subunits (Gαs, Gαi/o, Gαq/11, Gα12/13), the receptor/Gβγ interaction BRET assay can be viewed as a general method to monitor receptor-mediated G protein activation. In that respect, it may be considered superior to the widely used GTPγS binding assay since the nucleotide binding method has proven difficult for Gs and Gq coupled receptor due to the very weak signal/noise ratio obtained with these Gα subunits. When compared with the classical second messenger-based read-out that are classically used to identify the G proteins that can be activated by a given receptor, the BRET-based assays present the advantage of a single and homogeneous assay mode that directly measure the engagement of the G protein. Thus the receptor/G protein interaction BRET assay could advantageously be used as a general strategy for the identification of ligands for GPCRs.

Directly monitoring the interaction between various receptors (fused to GFP2, GFP10 or YFP) and distinct Gα subunits (fused to Rluc) or between distinct Gα subunits (fused to Rluc) and various Gβγ subunits (fused to GFP2, GFP10 or YFP) also offers a tool to directly monitor the selectivity of interactions between the signaling partners in the response to a specific ligand (drug).

Even though the present invention has been exemplified through different receptor and G protein subunit constructs, seven of them have been newly generated and found to be useful for ligand texture fingerprinting in addition to the purposes described above:

phRluc-Gγ$_2$—The HindIII-XbaI fragment of pcDNA3.1-humanGγ$_2$ (Güthrie Research Institute, PA) was excised by double digestion with HindIII-XbaI and then subcloned into the HindIII-XbaI-digested humanized pRluc-C1 vector (Perkin Elmer, Lifescience). The final phRluc-Gγ$_2$ expression vector will encode the human Gγ$_2$ of heterotrimeric G protein subunit fused to its N-terminus to the humanized luciferase.

pGFP$^2$-Gγ$_2$—The HindIII-XbaI fragment of pcDNA3.1-humanGγ$_2$ (Güthrie Research Institute, PA) was excised by double digestion with HindIII-XbaI and then subcloned into the HindIII-XbaI-digested humanized pGFP$^2$—C3 vector (Perkin Elmer, Lifescience). The final pGFP$^2$-Gγ$_2$ expression vector will encode the human Gγ$_2$ of heterotrimeric G protein subunit fused to its N-terminus to the Green Fluorescent protein variant GFP$^2$.

phRluc-Gβ$_1$—The HindIII-XbaI fragment of pcDNA3.1-humanGβ$_1$ (Güthrie Research Institute, PA) was excised by double digestion with HindIII-XbaI and then subcloned into the HindIII-XbaI-digested humanized pRluc-C1 vector (Perkin Elmer, Lifescience). The final phRluc-Gβ$_1$ expression vector will encode the human Gβ$_1$ of heterotrimeric G protein subunit fused to its N-terminus to the humanized luciferase.

pGFP$^2$-Gβ$_1$—The HindIII-XbaI fragment of pcDNA3.1-humanGβ$_1$ (Güthrie Research Institute, PA) was excised by double digestion with HindIII-XbaI and then subcloned into the HindIII-XbaI-digested humanized pGFP$^2$-C3 vector (Perkin Elmer, Lifescience). The final pGFP$^2$-Gβ$_1$ will encode the human Gβ$_1$ of heterotrimeric G protein subunit fused to its N-terminus to the Green Fluorescent protein variant GFP$^2$.

pcDNA3.1-Gα$_{i1}$-60Rluc-pcDNA3.1-Gα$_{i1}$-91Rluc-pcDNA3.1-Gα$_{i1}$-122Rluc—Coding sequence of humanized Rluc (PerkinElmer, Lifescience) was PCR amplified without its STOP and inserted via flexible linkers (SGGGGS) in the coding sequence of human Gα$_{i1}$ (pcDNA3.1-human Gα$_{i1}$, Güthrie Research Institute, PA) between: residues L91 and K92 (Gα$_{i1}$-91Rluc, corresponding to Sequence ID No. 2) or residues E122 and L123 (Gα$_{i1}$-122Rluc, corresponding to Sequence ID No. 3) or residues G60 and Y61 (Gα$_{i1}$-60Rluc, corresponding to Sequence ID No. 1). The final pcDNA3.1-Gα$_{i1}$-91Rluc and pcDNA3.1-Gα$_{i1}$-122Rluc expression vectors will encode the human Gα$_{i1}$ of heterotrimeric G protein subunit fused to its helical domain to the humanized luciferase, while the pcDNA3.1-Gα$_{i1}$-60Rluc expression vector will encode the human Gα$_{i1}$ of heterotrimeric G protein subunit fused to its linker 1 region to the humanized luciferase.

Thus, in addition to shedding new light on the dynamics of receptor-mediated G protein activation, the BRET-based biosensors of the present invention can be used to directly probe the selectivity of interaction between receptors and G protein subunits and therefore offers a sensitive assay to monitor receptor-mediated G protein activation. The invention therefore provides a sensitive assay for the screening of candidate drugs acting on specific G protein coupled receptors, which may be incorporated in a kit for sale or distribution.

Other objects, advantages and features of the present invention will become apparent upon reading of the following n on restrictive description of preferred embodiments thereof, given by way of example only with reference to the accompanying drawings.

BRIEF DESCRIPTION OF THE FIGURES

FIG. 2C: BRET measured between GFP-Gβ1 (FIGS. 2C-1, 2C-3, 2C-5, and 2C-7) or GFP-Gγ2 (FIGS. 2C-2, 2C-4, 2C-6, and 2C-8) and Rluc-tagged V2 vasopressin receptor (V2R-Rluc), α$_{2A}$ adrenergic receptor (α$_{2A}$AR-Rluc), sensory neuron-specific receptor 4 (SNSR4-Rluc) and thromboxane A2α receptor (TPα-Rluc), as indicated, after coexpression of the indicated G protein subunits, and in the presence of their respective selective agonists (AVP, UK14304, BAM22 and U46619). Results are expressed as the difference in the BRET signal observed in the presence and the absence of agonists. FIG. 2D: BRET measured in cells co-expressing β2AR-Rluc or CD8-Rluc and GFP10-Gβ1 (+Gγ2+Gαs, FIG. 2D-1) or GFP10-Gγ2 (+Gβ1+Gαs, FIG. 2D-2) and stimulated (■) or not (□) with 10 μM Iso. Data represent the mean±SEM of 3-4 independent experiments. *, p<0.05. #, p<0.05 compared with Iso induced BRET in the absence of co-transfected Gα subunit (dashed line).

FIG. 3A: BRET measured in HEK293T cells co-expressing β2AR-Rluc with either GFP10-Gβ1 (FIG. 3A-1) or GFP10-Gγ2 FIG. 3A-2 in the presence of increasing concentrations of Iso.

(FIG. 4A-1) kinetics of net agonist-promoted BRET signal using data from FIG. 4A-2. Data are representative of 3-4 independent experiments each performed in quadruplicate. FIG. 4B: BRET measured every 0.05 sec for 30 sec in cells expressing β2AR-Rluc and GFP10-Gγ2, and pretreated (open triangle) or not (filled triangle) with 1 μM Iso. ICI (100 μM) was injected 5 seconds after the beginning of the reading. Data are representative of 3-4 independent experiments each performed in quadruplicate. FIG. 4C: BRET measured in HEK293T cells coexpressing β2AR with RLuc-Gβ1 and Gαs-GFP10, and stimulated (■) or not (□) with 10 μM Iso. Data represent the mean±SEM of 3 independent experiments. *, p<0.05. FIG. 4D: Comparison of long term agonist stimulation on BRET and cAMP production. FIG. 4D-1: BRET measured in cells expressing β2AR-Rluc and GFP10-Gγ2, and stimulated with 10 μM Iso for up to 1 hr. Results are expressed as percentage of the maximum Iso-induced BRET signal obtained at 1 minute. FIG. 4D-2: Iso-stimulated cAMP production measured in membranes derived from β2AR expressing cells, and pretreated or not with 10 μM Iso for the indicated times. Data represent the mean±SEM of 3 independent experiments each performed in triplicate FIG. 4F: BRET measured in cells expressing α$_{2A}$AR-Rluc and GFP10-Gγ2, and stimulated with 10 μM UK14304 for up to 1 hr. Results are expressed as percentage of the maximum UK14304-induced BRET signal obtained at 1 min and represent the mean±SEM of 3 independent experiments each performed in duplicate.

FIG. 7: Vasopressin-selective agonist AVP is unable to modulate BRET signal between β2AR-Rluc/GFP-Gγ2 (FIG. 7-1) or GFP-Gβ1 (FIG. 7-2). HEK293T cells were co-transfected with both β2AR-Rluc, Myc-V2R and either GFP-Gβ1 or GFP-Gγ2, and stimulated or not with 10 μM AVP or Iso. Data represent the mean±SEM of three different experiments, each performed in duplicate and are expressed as percentage of BRET signal obtained in the absence of agonist (basal).

FIG. 10: Basal BRET signal between β2AR-Rluc/GFP-Gγ2 is sensitive to a β2AR-inverse agonist. Membrane preparations were obtained from HEK293T cells transfected with β2AR-Rluc and GFP-Gγ2, and stimulated or not (basal) with 10 μM Iso or ICI-118551. Data represent the mean±SEM of three different experiments, each performed in duplicate.

FIG. 11: Kinetics analysis of β2AR/Gγ2 interactions. BRET was measured every second for 1 minute in cells expressing β2AR-Rluc and GFP-Gγ2. Iso (10 μM) was injected 5 seconds after the beginning of the reading. Data are representative of 5 independent experiments each performed in quadruplicate.

FIG. 12-4 shows the respective signals measured schematically.

FIG. 13-1 shows the respective signals measured schematically.

FIG. 14: BRET was measured in HEK293T cells co-expressing $β_2$AR-GFP and either Rluc-$Gβ_1$ (FIG. 14-1) or Rluc-$Gγ_2$ (FIG. 14-2), and stimulated (■) or not (□) with 10 μM Iso.

FIG. 15: FIG. 15A: Schematic representation of receptor and G protein subunits BRET constructs. Receptors were fused at their C-terminal with Rluc or GFP variants (GFP10; YFP; Venus). Human $Gβ_1$ and $Gγ_2$ G protein subunits were both fused at their N-terminal to Rluc or GFP10 while Rluc was inserted between L91 and K92 residues ($G\alpha_{i1}$-91Rluc) or between residues E122 and L123 ($\alpha_{i1}$-122Rluc) within $G\alpha_{i1}$ subunit.

FIG. 19: Configurations of the different BRET assays used to probe receptor-mediated G protein activation. Schematic representation of a GPCR (purple, Rhodopsin PDB code 1L9H) and a heterotrimeric G protein composed of αi1 (FIG. 19-A19-F), β1 (FIG. 19A), and γ2 subunits (FIG. 19B) (light blue, red and yellow respectively; PDB code 1GG2) interacting at the plasma membrane, fused to luciferase (blue; PBD code 1LC1) or to GFP (green; PDB code 1GFL), as indicated.

FIG. 23: BRET measured in cells coexpressing $G\alpha_{i1}$-91Rluc or $G\alpha_{i1}$-122Rluc with either GFP10-tagged $β_2$-adrenergic receptor ($β_2$AR-GFP10) (FIGS. 23A-1 and 23A-2) or YFP-tagged Calcitonin receptor like receptor (CGRP-R=CRLR-YFP+RAMP1) (FIGS. 23B-1 and 23B-2), and stimulated (black) or not (white) with their respective selective agonists (Isoproterenol [Iso] and CGRP, 10 μM). *, P<0.05.

FIG. 25: BRET measured as in FIG. 20 in the presence of selective $\alpha_{2A}$-adrenergic ligands (UK14,304 [UK], Dexmedetomidine [Dex], Clonidine [Clo], Yohimbine [Yo], RX821002 [RX], 10 μM). Results are expressed as the difference in BRET signal observed in the presence and absence of ligand. *, P<0.05; ***, P<0.001 compared with UK-promoted BRET with Gβ1 (FIG. 25-1) Gγ$_2$ (FIG. 25-2) Gα$_{i1}$-91 (FIG. 25-3), and Gα$_{i1}$-122 (FIG. 25-4).

FIG. 27: BRET measurements of Gα$_{i1}$β$_1$γ$_2$ subunits interactions in living cells. FIG. 27B: Cells cotransfected with Gα$_{i1}$-91Rluc, GFP10-Gγ$_2$ and α$_{2A}$AR-Venus were stimulated (black) or not (white) with 10 μM UK14,304. BRET (FIG. 27B-2) or BRET (FIG. 27B-3) was then measured by adding Coelenterazine h or DeepBlueC coelenterazine, respectively. Data represent the mean±s.e.m. of 4 independent experiments. *, P<0.05. Shown schematically in FIG. 27B-1.

FIG. 28: Insight into Gα$_{i1}$β$_1$γ$_2$ structural rearrangements. BRET measured in cells coexpressing either Gα$_{i1}$-91Rluc (FIG. 28A-1), Gα$_{i1}$-122Rluc (FIG. 28A-2) or Gα$_{i1}$-60Rluc (FIG. 28B) with GFP10-Gγ$_2$, in the presence of different GPCRs (α$_{2A}$-, β$_1$- and β$_2$AR, dopamine-D1, δ-opioid [δOR], muscarinic-M2 [m2], chemokine-CXCR4 and -CCR5, calcitonin gene related peptide [CGRP-R=CRLR+RAMP1], prostaglandine-EP4, vasoactive intestinal peptide [VIP] and secretine). Results are expressed as the difference in BRET signal observed in the presence and absence of ligand and represent the mean±s.e.m. of 3-4 independent experiments.

FIG. 29: Kinetic analysis of receptor and QL-Gαi1 mutant interaction. BRET measured in cells coexpressing QL-Gαi1-122Rluc and β2AR-GFP10 and stimulated or not with 10 μM Iso for up to 4 min. Results are expressed as the difference in the BRET signal observed in the presence and absence of ligand and represent the mean±s.e.m. of 2 independent experiments.

FIG. 30: BRET measurements of GPCRs and Gαs interactions. BRET was measured in cells coexpressing Gαs-71-GFP10 with Rluc-Gγ2 in the presence of different GPCRs (β1- and β2adrenergic, dopamine-D1, vasopressin-V2, prostaglandine-EP4, vasoactive intestinal peptide [VIP] and secretine). Results are expressed as the difference in BRET signal observed in the presence and absence of ligand and represent the mean±s.e.m. of 3 independent experiments.

FIG. 31: FIG. 31A: Schematic complex in the plasma membrane between rhodopsin (gray; PDB code 1GZM) and the inactive heterotrimeric G protein composed of α$_{i1}$, β$_1$, and γ$_2$ subunits (light blue/violet, red and yellow, respectively; PDB code 1GG2). Gα$_{i1}$ N-terminal helix (Nα) is shown in brown, while Gα$_{i1}$-GTPase and Gα$_{i1}$-helical domains (α$_{i1}$H) are in light blue and violet respectively. Linker 1 connecting Gα$_{i1}$-GTPase to the Gα$_{i1}$H is represented in green. Both Gα$_{i1}$N (Nα) and Gγ$_2$ C-terminal helix (Cγ) are anchored to the membrane trough lipid modification. Arrows highlight the different positions of Rluc or GFP probes inserted in the Gα$_{i1}$β$_1$γ$_2$ heterotrimer.

FIG. 32: Schematic representation of the complexes for the possible biosensors presented in the patent. FIGS. 32B-1, 32B-2, and 32B-3, respectively.

DESCRIPTION OF THE PREFERRED EMBODIMENTS

Definitions

Figure 1:
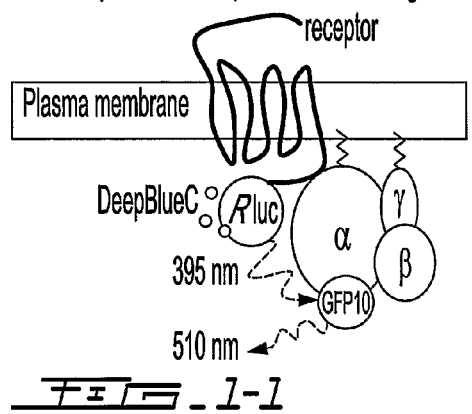
FIG. 1: Illustration of the receptor/G protein BRET2 assay. BRET was measured between receptor-Rluc and Gαs-GFP10 (FIG. 1-1), GFP10-Gγ2 (FIG. 1-3) or GFP10-Gβ1 FIG. 1-2 as indicated. Upon degradation of its substrate (DeepBlueC coelenterazine), the Rluc fused to the C-terminus of the receptor emits a blue light with an emission peak at 395 nm. When receptor and G protein are in close proximity (<100 Angstroms), a non-radiative transfer of energy will occur between Rluc and GFP10 fused to the different G protein subunits, resulting in re-emission of fluorescence with a peak at 510 nm.

Unless specifically defined, the terms used in the present application have the meanings that one of ordinary skill in the art would ascribe to them.

In order to provide a clear and consistent understanding of the terms used in the present specification, a number of definitions are provided below. Moreover, the present description refers to a number of routinely used chemical and technical terms; definitions of selected terms are provided for clarity and consistency.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or method steps.

The term "about" is used to indicate that a value includes an inherent variation of error for the device or the method being employed to determine the value.

| | |
|---|---|
| GPCR | G protein-coupled receptor |
| GDP | Guanosine diphosphate |
| GTP | Guanosine triphosphate |
| BRET | Bioluminescence resonance energy transfer |
| FRET | Fluorescence resonance energy transfer |

-continued

| Biosensor | Type of biomolecular probe that measures the presence or concentration of biological molecules, biological structures, etc., by translating a biochemical interaction at the probe surface into a quantifiable physical signal such as light, electric pulse or fluorescent signal. |
|---|---|
| Ligand texture fingerprint | Ligand-selective receptor conformations introduce the concept of 'texture' to drug effects, with respect to ligands possessing quality in addition to quantity of efficacy.[33] |
| $\beta_2$AR | beta 2-adrenergic receptor |
| Rluc | Renilla luciferase |
| GFP | Green fluorescent protein |
| Iso | Isoproterenol |
| Feno | fenoterol |
| ICI | ICI-118551 |
| V2R | V2-vasopressin |
| $\alpha_{2A}$AR | alpha 2-adrenergic receptor |
| SNSR-4 | Sensory neuron-specific receptor 4 |
| Ip | Immunoprecipitation |
| Ib | Immunoblot |

Materials and Methods
cDNA Expression Vectors

All receptor constructs were fused in frame at their carboxyl terminus to either the humanized Rluc, or GFP10, or YFP/Venus. GFP10 is a variant form of the green fluorescent protein (GFP) previously reported[23]. Plasmids encoding β2AR-Rluc and V2R-Rluc were described previously[23,58]. β2AR-D79N-Rluc construct was generated using oligonucleotide-directed mutagenesis (Quick-Change™ Site-directed Mutagenesis Kit, Stratagene) and pcDNA3.1-β2AR-Rluc as template. α2AAR-Rluc and TPα-Rluc were obtained by subcloning the α2AAR and TPα receptors coding sequences lacking their stop codon into the humanized Rluc-N1 and -N3 vectors, respectively (Perkin Elmer, Lifescience). Plasmid encoding SNSR4-Rluc (pcDNA3.1-SNSR4-Rluc) was a gift from Astra-Zeneca, Montréal.

To obtain $\alpha_{2A}$AR-Venus, the coding sequence of Venus[35] was PCR amplified and cloned in frame with the C-terminal of $\alpha_{2A}$AR by replacing the Rluc tag in the p$\alpha_{2A}$AR-Rluc vector. $\alpha_{2A}$AR-GFP2 and $\alpha_{2B}$AR-GFP2 were obtained by subcloning the receptor coding sequences lacking their stop codon into the humanized pGFP2-N1 vector (Perkin Elmer, Lifescience).

All Gβ and Gγ constructs were fused in frame at their amino-terminus to the humanized Rluc or GFP10. Plasmids encoding GFP10-Gβ1 and -Gγ2 were a gift from Biosignal/Perkin Elmer, Lifescience. Gαs-GFP10 was generated by subcloning GFP10 into EcoRI/BsrGI sites of the Gαs-EGFP construct generously provided by Dr. Rasenick[43].

Coding sequence of humanized Rluc (PerkinElmer, Lifescience) was PCR amplified without its STOP and inserted via flexible linkers (SGGGGS) in the coding sequence of human G$\alpha_{i1}$ between: residues L91 and K92 (G$\alpha_{i1}$-91Rluc) or residues E122 and L123 (G$\alpha_{i1}$-122Rluc) or residues G60 and Y61 (G$\alpha_{i1}$-60Rluc). Similar strategy was used to obtained the Rluc-tagged constitutively active Q204L-G$\alpha_{i1}$ mutant (QL-G$\alpha_{i1}$-122Rluc) but using Q204L-G$\alpha_{i1}$ as a template.

Plasmid encoding Rluc-Gγ2 was obtained by subcloning the human Gγ2 coding sequence coding sequence into the humanized Rluc-N1 vector (Perkin Elmer, Lifescience).

To generate a CD8-Rluc construct, the fragment of pcDNA-CD8-βARK-C18 encoding the extracellular and transmembrane domain of the CD8 lymphocyte-specific receptor (from codon 1 to 209) was subcloned into the humanized pRluc-N1 vector (Perkin Elmer, Lifescience). The resulting DNA construct, CD8-Rluc, expresses the extracellular and transmembrane domain of CD8 fused to Rluc at its carboxyl tail (intracellular domain).

Ramp1 and N-terminal tagged-HA-GABAB-R2 (GBR2) were a gift from GlaxoSmithkline and has been previously described[59]. The plasmid encoding N-terminal Myc-tagged vasopressin type-2 receptor (Myc-V2R) has also been described previously[60]. Vector encoding CRLR-YFP was a generous gift from Patrick Sexton.

Plasmid encoding the βarrestine1 truncated form, YFP-βarr1-T383, was a generous gift from Stephane Laporte[25].

All plasmids encoding wild type G protein subunits (Gαs, Gαi1, Gαi2, Gαq, Gα11, Gα13, Gβ1, Gγ2) were obtained from the Güthrie Research Institute (PA).

All generated constructs were confirmed by sequencing.

Cell Culture and Transfections

Human embryonic kidney 293 cells (HEK293T) were cultured in Dulbecco's modified Eagle's medium supplemented with 10% fetal bovine serum, 2 mM L-glutamine, 100 unit/ml penicillin/streptomycin at 37° C. in a humidified atmosphere at 95% air and 5% CO2. In all cases, transient transfections were performed 24 hours after cell seeding using the calcium phosphate precipitation method, except for the immunofluorescence studies where FuGENE6 (Roche Molecular Biochemicals) was utilized according to the manufacturer's protocol.

Immunofluorescence Confocal Microscopy

HEK293T cells were seeded and transfected in 6 well plates containing glass coverslips precoated with 1 mg/ml poly-L-Lysine. For CD8-Rluc or β2AR-Rluc and HA-GBR2 localization experiments, 48 hrs after transfection, HEK293T cells were incubated overnight at 4° C. with rat monoclonal anti-HA antibody (3F10) for cell surface immunostaining of GBR2. HA-labelling was revealed using a Alexa 488-conjugated goat anti-rat antibody (Molecular Probes) for 30 min at RT. Cells were then washed, fixed with 3% paraformaldehyde in PBS for 15 min, permeabilized for 10 min with 0.3% Triton X-100 in blocking buffer (PBS-0.2% BSA), and incubated for 30 min with a mouse anti-*Renilla* luciferase antibody (Chemicon International). Immunoreactivity was revealed using a Texas Red-conjugated secondary goat anti-mouse antibody (Molecular Probes). Images were acquired on a Leica TCS SP1 laser-scanning microscope.

Cell Membranes Preparation

Cell membranes used for the measurement of the adenylyl cyclase activity or the radioligand binding assay were prepared as previously described[61].

Adenylyl Cyclase Activity

Figure 3B:
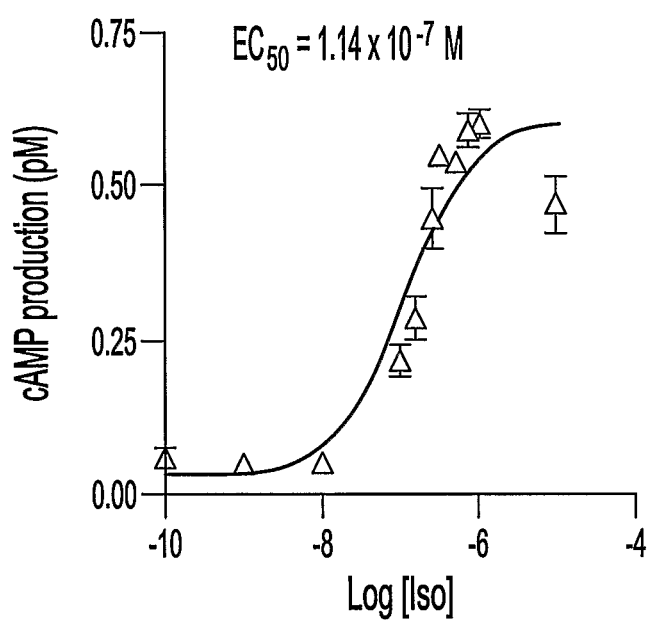
FIG. 3B: cAMP production measured in HEK293T cells expressing β2AR in the presence of increasing concentrations of Iso.

Adenylyl cyclase activity was determined in membrane preparation (FIG. 4c) or in whole cells (FIGS. 3b, d and e). Membrane adenylyl cyclase activity was determined using anion exchange chromatography, as previously described[61]. For whole cell cAMP production, cells were detached in PBS-5 mM EDTA and resuspended in PBS-0.1% glucose at RT and incubated at RT for 10 min in the presence of 0.7 mM 3-isobutyl-1-methylxanthine (IBMX). The indicated drugs were then added for 30 min at 37° C. and the reaction stopped by adding lysis buffer (pH 7.3) for 10 min at RT according to Molecular Devices Corporation. cAmp content of lysated cells was then measured using a fluorescent based-competitive immunoassay (Catchpoint™ cyclic-AMP Fluorescent Assay Kit-96-well format, Molecular Devices Corporation). Fluorescence readings were performed using the FlexStation™ instrument (Molecular Devices Corporation).

Radioligand Binding Assay

β2AR-Rluc or D79N-β2AR-Rluc binding properties were determined as previously described[61] by competitive binding of 30 pM $^{125}$I-cyanopindolol (CYP) (NEN, Perkin Elmer) by increasing concentrations of unlabeled isoproterenol. Non-specific binding was estimated in the presence of 10 μM unlabeled cyanopindolol.

Bioluminescence Resonance Energy Transfer (BRET) Assay

BRET$^2$ was used as previously described[23].

Rluc-tagged receptors and G protein constructs were transiently co-transfected in HEK293T cells. Except when otherwise specified, all BRET measurements were made in cells coexpressing receptor-Rluc and either Gαs-GFP10, GFP10-Gβ1 or GFP10-Gγ2 along with their complementary subunits (Gβ1γ2, Gγ2αs or Gβ1αs, respectively). For the experiment using α2AAR-Rluc (FIG. 4f), the G protein heterotrimer was complimented with the most specific Gαi2. Forty-eight hours post-transfection, cells were washed twice with PBS, detached with PBS-5 mM EDTA and resuspended in PBS-0.1% glucose at RT. Cells (50 μg of proteins per well) were then distributed in a 96-well microplate (white Optiplate, PerkinElmer) and incubated in the presence or absence of different ligands for 1 min except in the case of the kinetic studies where the times are indicated. DeepBlueC™ coelenterazine (PerkinElmer) was added at a final concentration of 5 μM, and readings (except for the kinetic studies; see below) were collected using a modified top-count apparatus (TopCount.NX™, Packard Bioscience) that allows the sequential integration of the signals detected in the 370-450 nm and 500-530 nm windows using filters with the appropriate band pass (Chroma). The BRET signal was determined by calculating the ratio of the light emitted by GFP10 (500-530 nm) over the light emitted by the Rluc (370-450 nm). The net BRET values were obtained by subtracting the BRET background signal detected when the Rluc-tagged construct was expressed alone from BRET signals detected in cells coexpressing both Rluc- and GFP10-tagged constructs. Identical background values of 0.15 were obtained for all Rluc-tagged constructs expressed alone. The expression level of each protein was determined by direct measurement of total fluorescence and luminescence on aliquots of the transfected cells. The GFP10 total fluorescence was measured using a Fluoro-Count (PerkinElmer) with an excitation filter at 400 nm, an emission at 510 nm, and the following parameters: gain 1; PMT 1100 V; time 1.0 s. After fluorescence measurement, the same cells were incubated for 8 min with Coelenterazine h (Molecular Probes) at a final concentration of 5 μM and the total luminescence of cells was measured using a LumiCount (PerkinElmer Life Sciences) with the following parameters: gain 1; PMT 900 V; time 0.5 s. In contrast to DeepBlueC coelenterazine, Coelenterazine h does not lead to energy transfer between Rluc and GFP10 and thus allows the assessment of the total Rluc activity. To avoid variations in the BRET signal that could result from fluctuations in the relative expression levels of the energy donor and acceptor, transfection conditions were designed so as to maintain a constant GFP10/Rluc expression ratio in each experimental set.

For titration experiments (FIG. 26a-c), the expression level of each tagged-protein was determined by direct measurement of total fluorescence and luminescence on aliquots of the transfected cells. Total fluorescence was measured using a FluoroCount (PerkinElmer) with an excitation filter at 400 or 485 nm and an emission filter at 510 or 530 nm in the case of GFP2/GFP10 or YFP/Venus, respectively, and the following parameters: gain 1; PMT 1100 V; time 1.0 s. After fluorescence measurement, the same cells sample was incubated for 8 min with coelenterazine h (Molecular Probes) at a final concentration of 5 μM and the total luminescence of cells was measured using a LumiCount (PerkinElmer Life Sciences) with the following parameters: gain 1; PMT 900 V; time 0.5 s.

For kinetic analysis of receptor/Gαβγ interactions, Deep-BlueC™ or Coelenterazine h luciferase substrate was added prior to the injection of the different ligands using the Mithras LB 940 apparatus (Berthold) and MicroWin2000 software. Readings were then collected at 0.05 or 0.1 sec intervals. Injection of the different ligands was included with in the kinetic program to allow a baseline recording followed by real-time recording of the BRET changes. The BRET signals were determined for each time by calculating the ratio of the light emitted by GFP over that emitted by the Rluc. To determine the half-time (t½) of Iso-induced BRET, data were represented as the difference between the Iso-induced BRET signals and the average of basal BRET signal (net agonist-promoted BRET signal). Curves were fitted using a non-linear regression and one phase exponential association fit equation (GraphPad Prism).

For kinetic analysis of QL-Gα$_{i1}$-122Rluc/α$_2$AR-GFP10 interactions (FIG. 24), DeepBlueC™ coelenterazine was added to the cells prior to agonist addition and readings were collected at 24 s intervals using the modified TopCount. NXT™ instrument.

For agonist stimulations longer than 1 minute, cells were first treated with the ligand (agonist, antagonist, inverse agonist) and DeepBlueC™ coelenterazine added immediately before BRET readings in the modified TopCount.NXT™ apparatus. For these experiments, readings were taken directly in 96 well plates 72 hours post-transfection without detaching the cells.

Immunoprecipitation of Receptor/Gβγ Complexes

HEK293T cells were cotransfected in 100-mm plates with plasmids encoding either GFP10-Gβ$_1$ or -Gγ$_2$ in the presence or absence of α$_2$AR-Rluc. Forty-eight hours after transfection, cells were stimulated or not with 10 μM Iso for 30 sec and proceeded as previously described[37]. Immunoprecipitation was performed using the anti-α$_2$AR polyclonal antibody (SantaCruz). Immune complexes were eluted with Laemmli buffer containing 1 M urea and 50 mM dithiotreitol for 15 min at 45° C. Immunoblotting of α$_2$AR-Rluc was performed using a mouse anti-Rluc (ChemiconInternational) while immunoblotting of GFP10-Gβ$_1$ or -Gγ$_2$ were performed using a monoclonal anti-GFP (Clontech). Immune complexes were then visualized by chemiluminescence detection using anti-mouse horseradish peroxidase-conjugated IgG.

Statistical Analysis

One-way ANOVA followed by Student's t test was used (*) to determine statistically significant differences. When indicated, one-way ANOVA followed by Dunnett's test (#) was used as supplementary analysis to determine statistically significant differences from indicated control.

BRET Measurements Between Receptors and Gαβγ Fusion Proteins

The prototypical family 1 GPCR, β2-adrenergic receptor (β2AR), was used as the main model to probe the interaction with its preferred Gα subunit, Gαs, and the ubiquitous Gβ1 and Gγ2 subunits following receptor activation. For this purpose, a proximity-based BRET$^2$ assay was developed (FIG. 1) that relies on the non-radiative transfer of energy between the energy donor *Renilla reniformis* luciferase (Rluc) and a blue shifted variant of the *Aequorea Victoria* green fluorescent protein known as GFP10 that serves as the energy acceptor[23]. The receptor/G protein interaction assay was conceived by fusing Rluc to the carboxyl terminus of the β2AR while GFP10 was covalently attached to either Gαs, Gβ1 or Gγ2. For Gαs, the fluorophore was inserted within the linker 1 region between the helical and GTPase domains, as previously described[43], while the Gβ1 and Gγ2 subunits were fused to GFP10 at their amino terminus. Also as previously described[23], binding and signaling properties of the β2AR-Rluc were identical to those of the wild-type receptor. In agreement with previous reports[44,43], the fusion of GFP10 to Gαs, Gβ1 and Gγ2 was well tolerated, the fusion proteins being well targeted and active at the plasma membrane (data not shown).

Figures 1, 2:
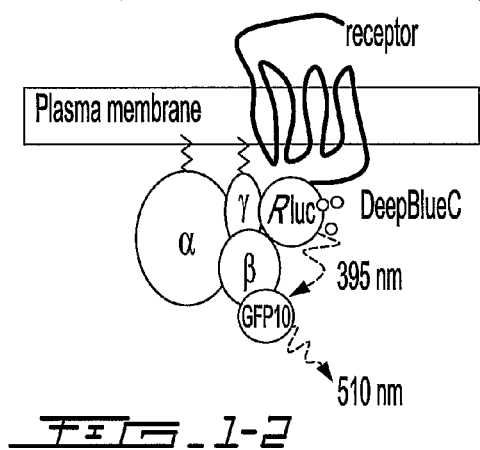
FIG. 2: BRET measurements of GPCRs/Gαsβ1γ2 interactions in living cells. GFP10 is referred to as GFP in the figure.
Figures 1, 2A:
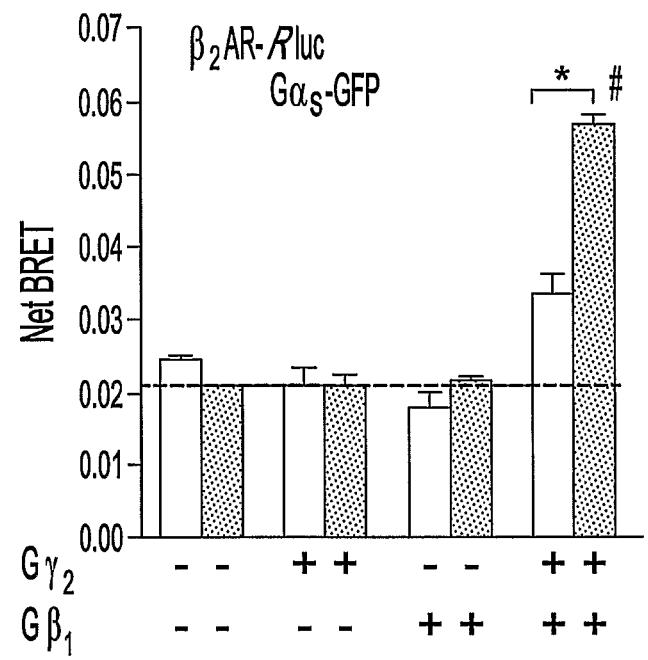
FIG. 2A: BRET measured in cells co-expressing Rluc-tagged β2 adrenergic receptor (β2AR-Rluc) with either Gαs-GFP10 (FIG. 2A-1), GFP10-Gβ1 (FIG. 2A-2), or GFP10-Gγ2 (FIG. 2A-3), in the presence of the indicated G protein subunits, and stimulated (■) or not (□) with 10 μM Iso.
Figures 2, 2A:
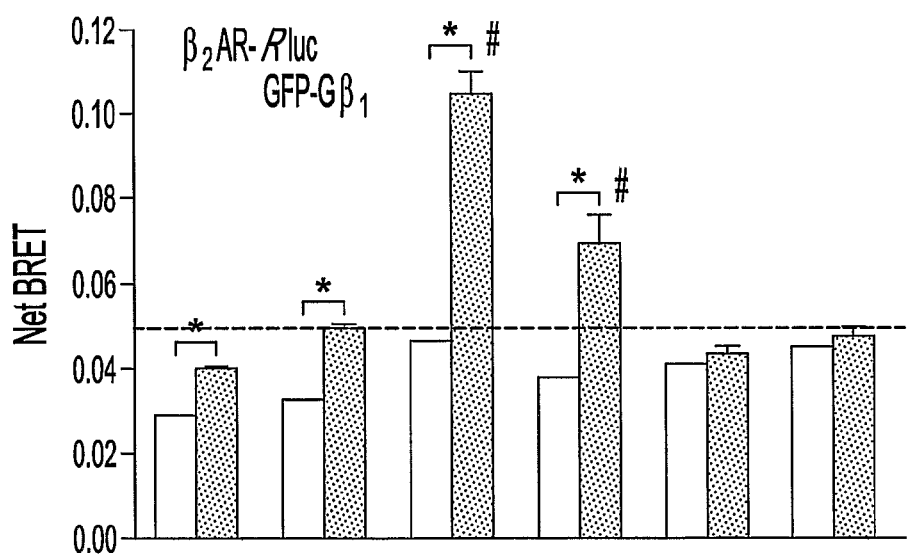
Figures 2, 2A, 3:
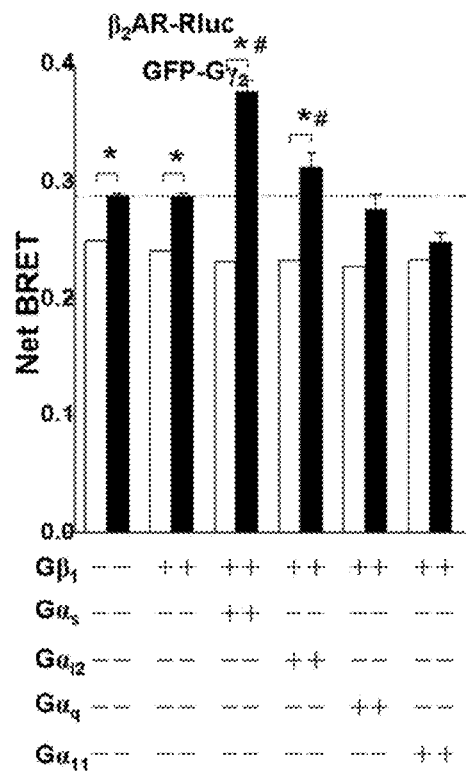

Receptor/G protein interactions were measured in living HEK293T cells co-expressing β2ARRluc and either Gαs-GFP10, GFP10-Gβ1 or GFP10-Gγ2 in combination or not with the complementary untagged G protein subunits (FIG. 2a). The same kind of assay was performed in HEK293T cells co-expressing RLuc-Gβ1 or RLuc-Gγ2 in combination with untagged Gαs with either β2ARGFP10 (FIG. 14). As shown in FIG. 2a, when GFP10-tagged G protein subunits were expressed individually with β2AR-Rluc, basal BRET signals were observed in all cases most likely reflecting constitutive interactions between the receptor and the G protein heterotrimer under basal conditions (see below). Exposure to the β-adrenergic agonist, isoproterenol (Iso), induced a modest but significant increase of BRET over the basal signal in cells co-expressing the β2AR-Rluc and either GFP10-Gβ1 (+36%) or GFP10-Gγ2 (+15%). Likewise, this agonist-modulated BRET signal was detected for the direct interaction between $Gα_{i1}$-Rluc and $β_2$AR-GFP10 in the absence of Gβ and Gγ subunits complementation, but not Gαs-GFP10 (FIG. 2c). This indicates that, in the absence of co-expressed complementary subunits, the agonist-promoted engagement of the G protein by the receptor could be detected by monitoring the BRET between the receptor and either Gβ1, Gγ2 or Gαi.

Co-expression of untagged complementary subunits significantly improved the sensitivity of the system to detect the agonist-promoted G protein engagement (FIG. 2a). In the case of Gαs-GFP10, co-expression of untagged Gβ1γ2 dimer (Gαs-GFP10+Gγ2+Gβ1) allowed the detection of an agonist-promoted increase in BRET with β2AR-Rluc (+68%). Similarly, for both GFP10-Gβ1 and GFP10-Gγ2, transfection with their complementary subunits (GFP10-Gβ1+Gγ2+Gαs or GFP10-Gγ2+Gβ1+Gαs) greatly favored the engagement of Gβγ by the receptor, as reflected by the substantial enhancement of the agonist-promoted BRET signal (+125% vs +36% with GFP10-Gβ1 and +63% vs +15% with GFP10-Gγ2). This potentiation most likely reflects the requirement for a stoichiometric expression of the three subunits for their proper processing and targeting to the plasma membrane[45] (data not shown).

Figure 2B:
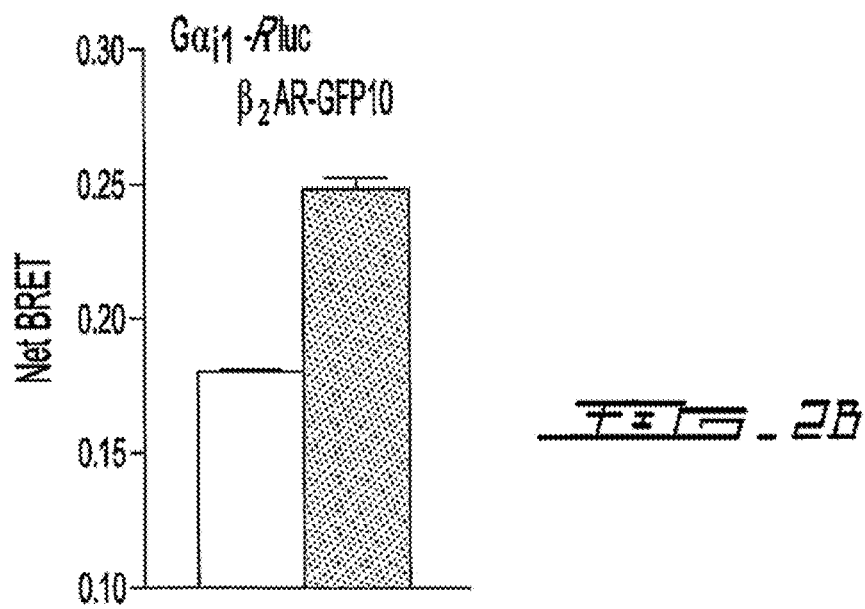
FIG. 2B: BRET measured in cells co-expressing Rluc tagged-Gα$_{i1}$ (Gα$_{i1}$-Rluc) and GFP tagged-β$_2$ adrenergic receptor (β$_2$AR-GFP10) only, in the presence (■) or not (□) of 10 μM Iso. Data represent the mean±SEM of 3-4 independent experiments.

Heterotrimer formation and trafficking of the Gβγ dimer to the cell surface is not sufficient to confer an agonist-stimulated BRET signal. Indeed, although all Gα subunits can promote the proper targeting of Gβ1 and Gγ2 to the cell surface[45] (data not shown), they showed significant selectivity in their ability to favor the agonist-stimulated BRET between the receptor-Rluc and GFP10-Gβ1 or GFP10-Gγ2. For instance, Gαs and to a lesser extent Gαi but not Gαq or Gα11 potentiated the agonist-induced BRET signal, despite similar expression levels of BRET donors and acceptors in each condition (FIG. 2a). This is consistent with the rank order of selectivity for various Gα subunits previously reported for the β2AR: Gs>Gi>>>Gq=G11[46]. The importance of the Gα subunit in directing the selectivity of Gβγ engagement was also observed for Rluc-tagged V2-vasopressin (V2R), α2A-adrenergic (α2AAR), sensory neuron-specific (SNSR-4) and thromboxane A2 receptor (TPαR) for which the agonist-stimulated BRET with GFP10-β1 and GFP10-Gγ2 was only potentiated by specific Gα subsets (FIG. 2b). V2R and α2AAR showed a very high level of selectivity, only one Gα subunit (Gαs and Gαi2 for V2R and α2AAR, respectively) potentiating the BRET response. For SNSR, both Gαq and Gαi2 potentiated the response, whereas for TPαR, the presence of Gα13 or Gαq, and to a lower extent Gαs or Gαi2 amplified the agonist-promoted BRET. In all cases, the Gα selectivity inferred indirectly through the receptor/βγ BRET assay reflected well the coupling specificity generally attributed to these receptors by functional assays[47,48].

This data therefore demonstrates that the identity of the Gα subunit plays a central role in determining the selectivity of interaction between receptors and specific Gβγ pairs. The data further demonstrates that the receptor-β/γ BRET-based assay can be advantageously used to probe the selectivity of interaction between receptors and the Gα subunits in living cells using a unique assay mode.

Figures 1, 5:
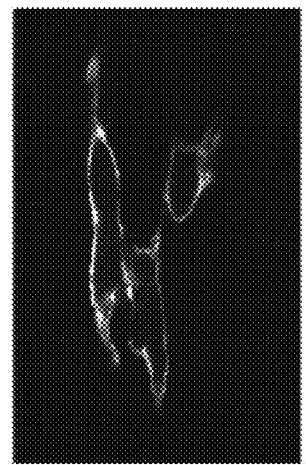
FIG. 5: Plasma membrane targeting of CD8-Rluc fusion protein. HEK293T cells were co-transfected with CD8-Rluc or β2AR-Rluc along with HA-GBR2 (used as a plasma membrane indicator). Localization of CD8-Rluc/β2AR-Rluc and HA-GBR2 was assessed by confocal immunofluorescence microscopy, as described below in Material and Methods, and shows colocalization of CD8-Rluc (FIG. 5-2) or β2AR-Rluc (FIG. 5-5) and HA-GBR2 (FIGS. 5-1 and 5-4) at the plasma membrane.
Figures 2, 5:
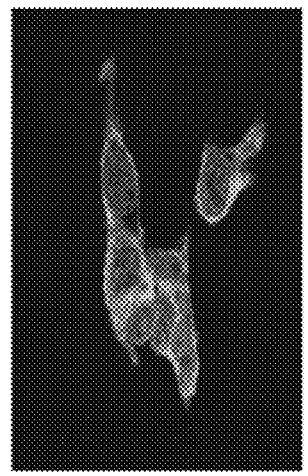
Figures 3, 5:
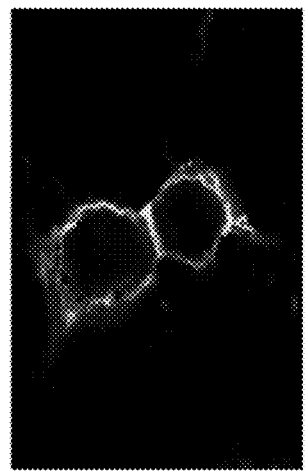
Figures 4, 5:
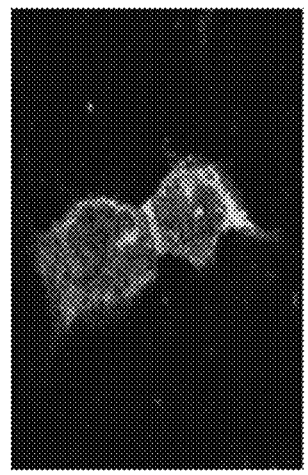
FIG. 4: Kinetics analysis of β2AR/Gβ1γ2 interactions. GFP10 is referred to as GFP in the figure.
Figures 1, 5:
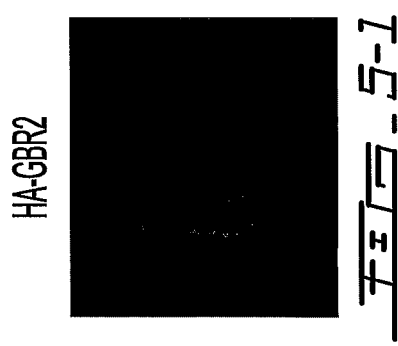
Figures 2, 5:
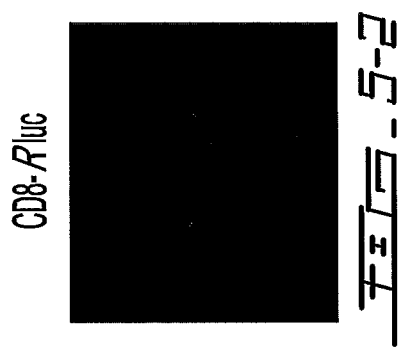
Figures 3, 5:
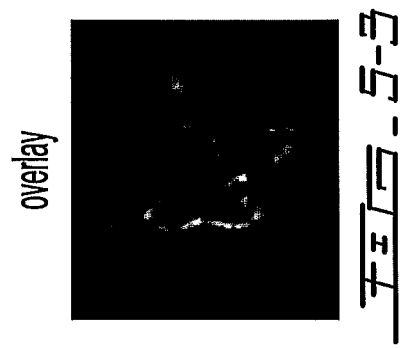
Figures 4, 5:
Figure 5:
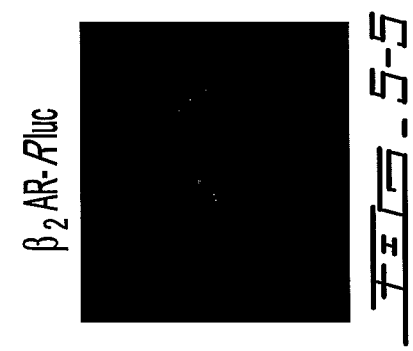

To confirm the specificity of the BRET signal observed between GFP10-Gβ1 or GFP10-Gγ2 and the receptor-Rluc, a negative control consisting of a truncated form of CD818 fused to Rluc (CD8-Rluc) was generated. This construct exhibits a subcellular distribution similar to that of the β2AR-Rluc (FIG. 5) and similarly exposes the Rluc moiety to the inner face of the plasma membrane. As shown in FIG. 2d, co-expression of CD8-Rluc with GFP10-Gβ1 or GFP10-Gγ2 in the presence of their complementary G protein subunits (GFP10-Gβ1+Gγ2+Gαs or GFP10-Gγ2+Gβ1+Gαs) only led to marginal basal BRET signals that were not modulated by agonist stimulation. This contrasted with the robust basal and agonist-promoted BRET signals observed between β2AR-Rluc and GFP10-Gβ1 or GFP10-Gγ2 for comparable Rluc and GFP10 expression levels, thus confirming the specificity of the BRET signals detected between the receptors and Gβγ subunits.

Agonist-Modulated BRET Signals Reflect Receptor-Mediated G Protein Activation

Figures 1, 2, 3:
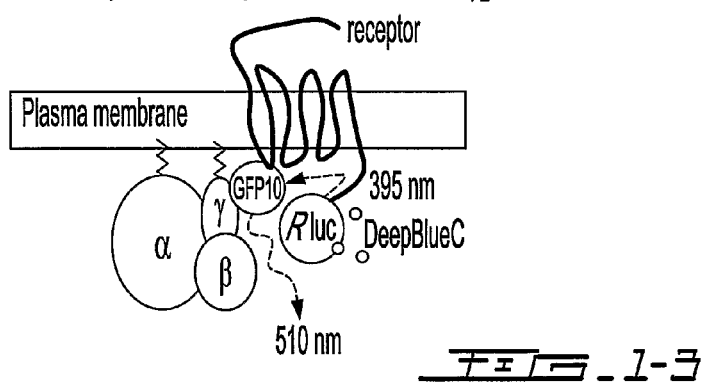
FIG. 3: BRET signals between β2AR and Gβγ reflect receptor-mediated G protein activation. GFP10 is referred to as GFP in the figure.
Figures 1, 3C:
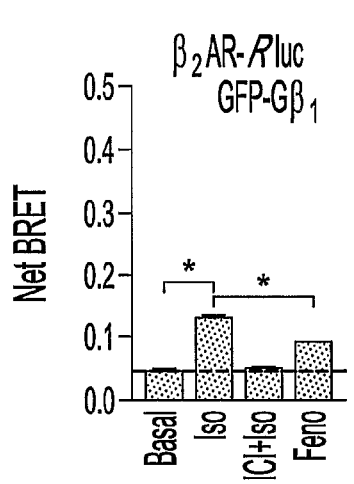
FIG. 3C: BRET measured in HEK293T cells coexpressing β2AR-Rluc and GFP10-Gβ1 (FIG. 3C-1) or GFP10-Gγ2 (FIG. 3C-2) in the absence (basal) or presence of the indicated β-adrenergic ligands.
Figures 2, 3C:
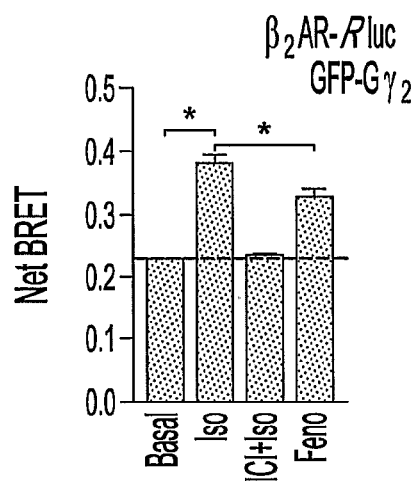
Figure 3D:
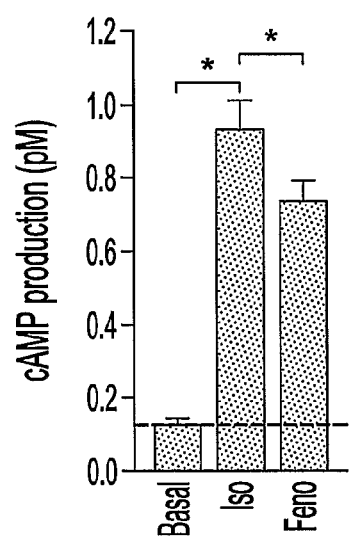
FIG. 3D: cAMP production measured in HEK293T cells expressing β2AR in response to stimulation with the indicated ligands.
Figure 3E:
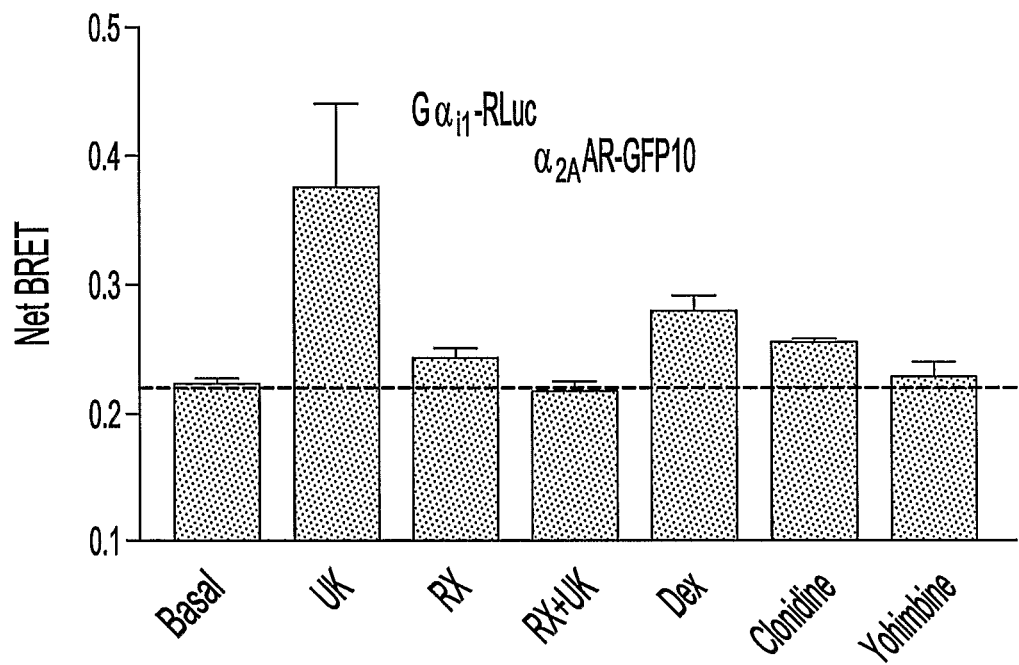
FIG. 3E: BRET measured in HEK293T cells coexpressing Gα$_{i1}$-Rluc and α$_{2A}$AR-GFP10, in the absence (basal) or presence of the indicated α-adrenergic ligands (10 μM UK14304, RX821002, Yohimbine, Dexmetodine, Clonidine).
Figures 5, 6:
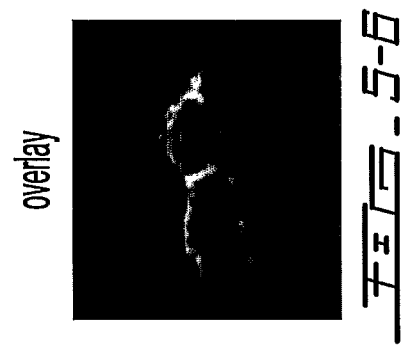
FIG. 6: Agonist-promoted BRET signal between β2AR-Rluc and GFP-Gγ2 is insensitive to pH. BRET was measured in membrane preparations derived from HEK293T cells transfected with β2AR-Rluc and GFP-Gγ2 in the absence (Δ) or presence (▲) of 10 μM Iso. Membranes were prepared as described in Materials and Methods in a lysis buffer at different pH (7.4, 7.0, 6.75, 6.45). Data represent the mean±SEM of three different experiments, each performed in duplicate.

Agonist stimulation led to a concentration-dependent elevation in the BRET between β2AR-RLuc and either GFP10-Gβ1 or -Gγ2 (FIG. 3a), which paralleled the rise in cAMP production (FIG. 3b), indicating that it faithfully reflects the activation state of the receptor. The intrinsic efficacies of different β-adrenergic agonists to activate the adenylyl cyclase (FIG. 3d) were also faithfully reflected in the ligand-promoted BRET responses detected between β2AR-Rluc and the GFP10-G protein subunits. Indeed, the partial agonist fenoterol (Feno) promoted only a fraction of the response evoked by the full agonist isoproterenol while the inverse agonist ICI-118551 (ICI) completely blocked the agonist-stimulated response (FIG. 3c). This is also true when considering the interaction between $Gα_{i1}$-Rluc and $α_{2A}$AR-GFP10 (FIG. 3e) for which the partial agonists Clonidine and Dexometodine (Dex), induced only a fraction of the full agonist modulation UK14304, while preincubation with the antagonist RX821002 completely blocked the agonist-stimulated response. Both α2 adrenergic antagonists RX821002 and Yohimbine are unable to modulate the BRET signal between the α2 receptor and the $Gα_{i1}$ subunit to exclude the possibility that the observed changes in BRET reflect local variations in pH that could modify the properties of Rluc and/or GFP10, additional measurements were carried out in buffered membrane fractions rather than in whole cells. Identical agonist-induced increases in BRET between β2AR-Rluc and GFP10-Gγ2 were detected for all pH values tested (6.5 to 7.5) (FIG. 6). Non-specific cellular changes resulting from GPCR activation were also ruled out since stimulation of another untagged Gαs-coupled receptor, the V2R, did not promote any increase in BRET between β2AR-Rluc and either GFP10-Gβ1 or -Gγ2 subunits (FIG. 7).

Figure 3F:
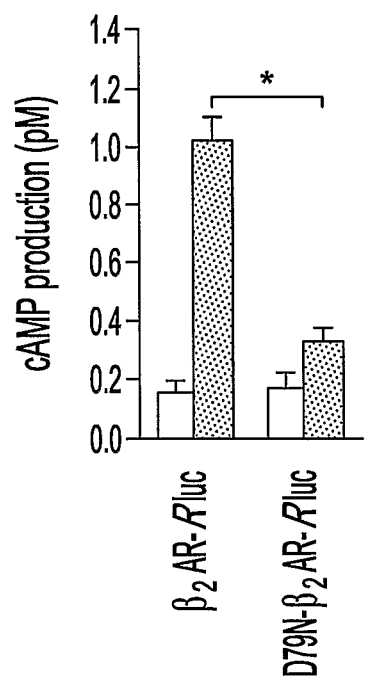
FIG. 3F: cAMP production measured in HEK293T cells expressing β2AR-Rluc or D79N-β2AR-Rluc in the absence (□) or presence (■) of Iso.
Figure 3G:
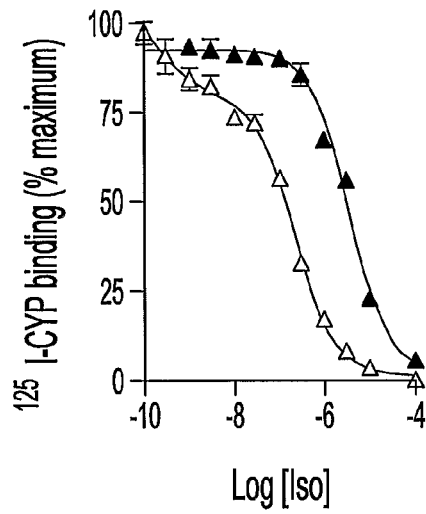
FIG. 3G: [$^{125}$I]-CYP competition binding by Iso in membranes derived from cells expressing β2AR-Rluc (Δ) or D79N-β2AR-Rluc (▲). Data are expressed as the percentage of maximal specific binding.
Figures 1, 3H:
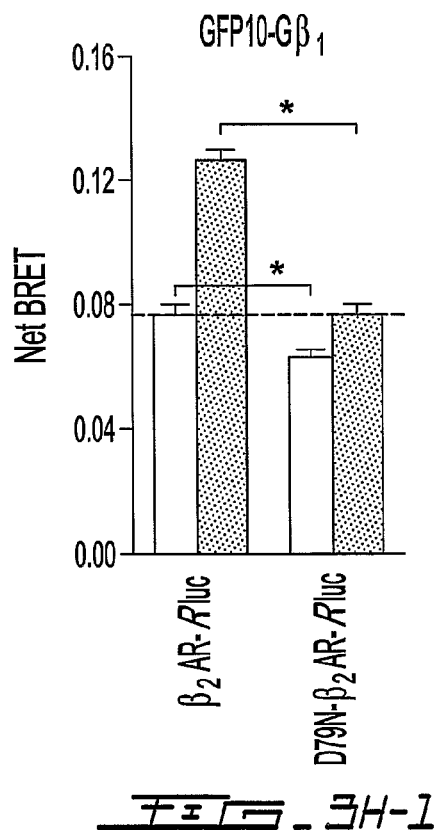
FIG. 3H: BRET measured in HEK293T cells expressing β2AR-Rluc or D79N-β2AR-Rluc with either GFP10-Gβ1 (FIG. 3H-1) or GFP10-Gγ2 (FIG. 3H-2), in the absence (□) or presence (■) of Iso.
Figures 2, 3H:
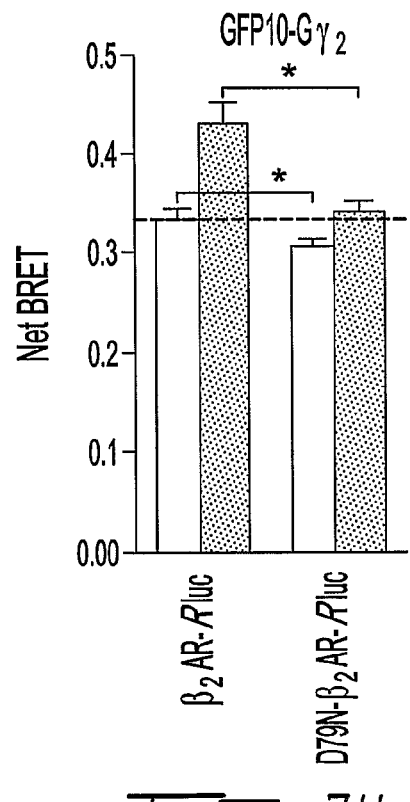
Figure 8:
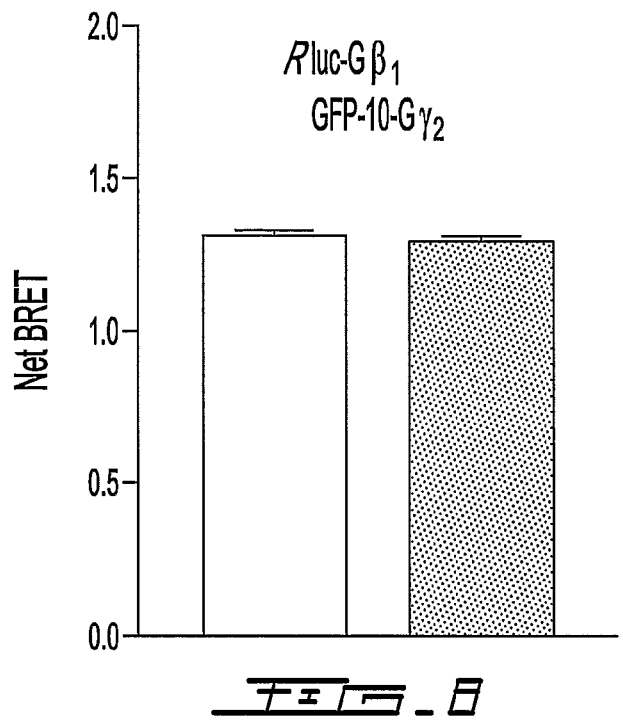
FIG. 8: Interactions between Gβ1 and Gγ2. BRET was measured in HEK293T cells coexpressing Rluc-Gβ1 and GFP-Gγ2 along with HAβ2AR and Gαs, and stimulated (■) or not (□) with 10 μM Iso. Data represent the mean±SEM of three different experiments, each performed in duplicate.

Finally, the specificity of the agonist-stimulated signal is further supported by the observation that isoproterenol did not promote any change in the strong BRET signal observed for the obligatory dimer between Rluc-Gβ1 and GFP10-Gγ2 (FIG. 8). The BRET-detected engagement of Gβγ following agonist binding appears to be a true reflection of the conformational changes linked to receptor activation. Indeed, mutation of aspartate 79 by an asparagine (D79N-β2AR-Rluc), which disrupts β2AR mediated-adenylyl cyclase activation without preventing agonist binding[50] (FIG. 3f, g), almost completely abolished the agonist-promoted BRET between the β2AR and either GFP10-Gβ1 or GFP10-Gγ2 (FIG. 3h).

Figures 1, 3I:
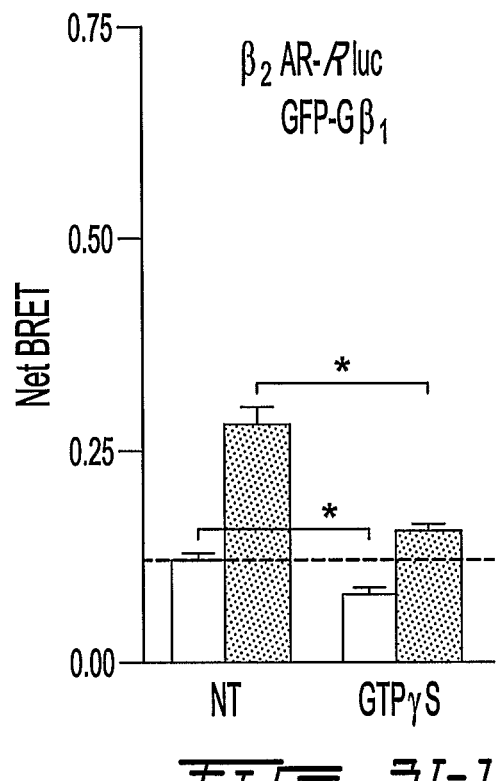
FIG. 3I: BRET measured in the absence (□) or presence (▲) of Iso in membrane preparations derived from HEK293T cells co-expressing β2AR-Rluc with either GFP10-Gβ1 (FIG. 3I-1) or GFP10-Gγ2 (FIG. 3I-2), and pretreated (GTPγS) or not (NT) with GTPγS during 90 min at 25° C. Data represent the mean±SEM of 3-4 independent experiments each performed in duplicate. *, p<0.05. Treatments: Iso, 10 μM; Feno, 10 μM; ICI, 100 μM; GTPγS, 200 μM.
Figures 2, 3I:
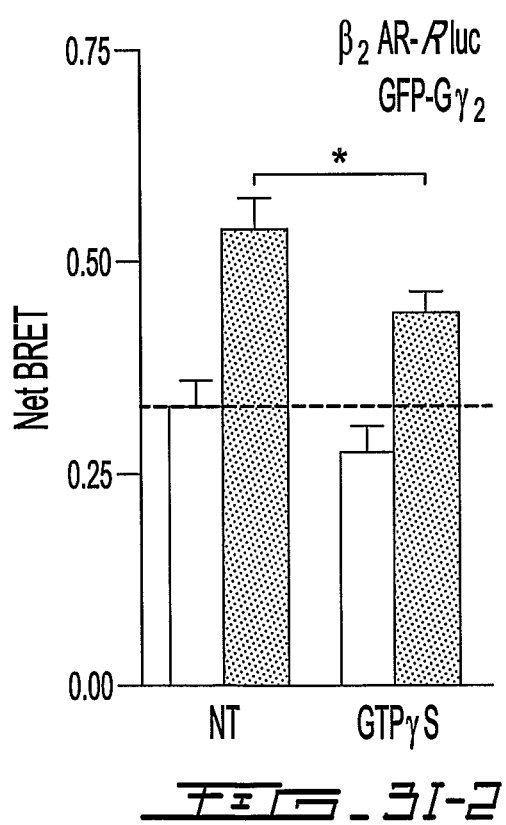
Figures 1, 9:
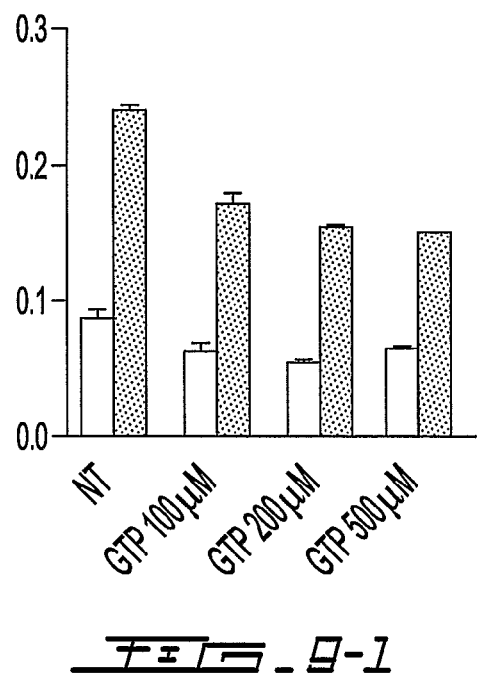
FIG. 9: BRET signal between β2AR-Rluc/GFP-Gβ1 or GFP-Gγ2 is GTP sensitive. Membrane preparations were obtained from HEK293T cells transfected with β2AR-Rluc and GFP-Gβ1 (FIG. 9-1) or -Gγ2 (FIG. 9-2), and pretreated or not (NT) with the indicated GTP concentrations during 90 min at 25° C. BRET was then measured in the absence (□) or presence (■) of 10 μM Iso.
Figures 2, 9:
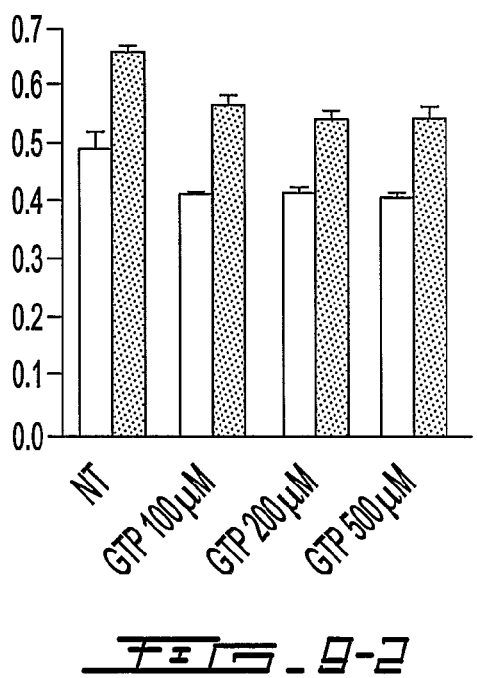

Interestingly, the basal BRET signal detected between the activation deficient D79N-β2AR-Rluc and GFP10-Gβ1 or GFP10-Gγ2 was lower than that observed for the wild type receptor, indicating that it reflects, at least in part, a receptor/G protein coupling resulting from receptor constitutive activity[51]. Also, consistent with the notion that the agonist-promoted increase in BRET reflects receptor-mediated G protein activation is the observation that the non hydrolysable GTP analog GTPγS, which interrupts the activation/inactivation cycle of the G protein, attenuated the agonist-promoted signal (FIG. 3i). In addition to its effect on the agonist stimulated BRET, the nucleotide also reduced the basal BRET observed in the absence of agonist, reinforcing the notion that the basal BRET signal most likely reflects constitutive receptor-G protein interactions. Similar results were obtained when using high concentrations of the hydrolysable nucleotide GTP (FIG. 9). The β2AR-specific inverse agonist, ICI-118551 (ICI) was also found to significantly lower the basal BRET signal between β2AR-Rluc and GFP10-Gγ2 (FIG. 10), thus confirming that the basal BRET signal reflected constitutive receptor activity.

Figures 1, 4A:
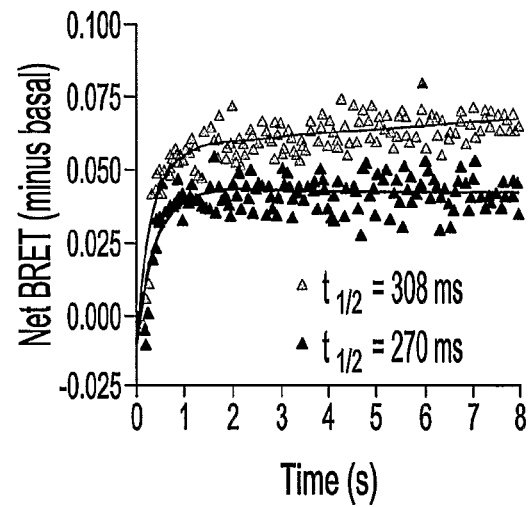
FIG. 4A: BRET measured every 0.05 seconds for 10 seconds in cells expressing β2AR-Rluc and GFP10-Gβ1 (filled triangle) or GFP10-Gγ2 (open triangle). Iso (10 μM) was injected 2 seconds after the beginning of the reading.
Figures 2, 4A:
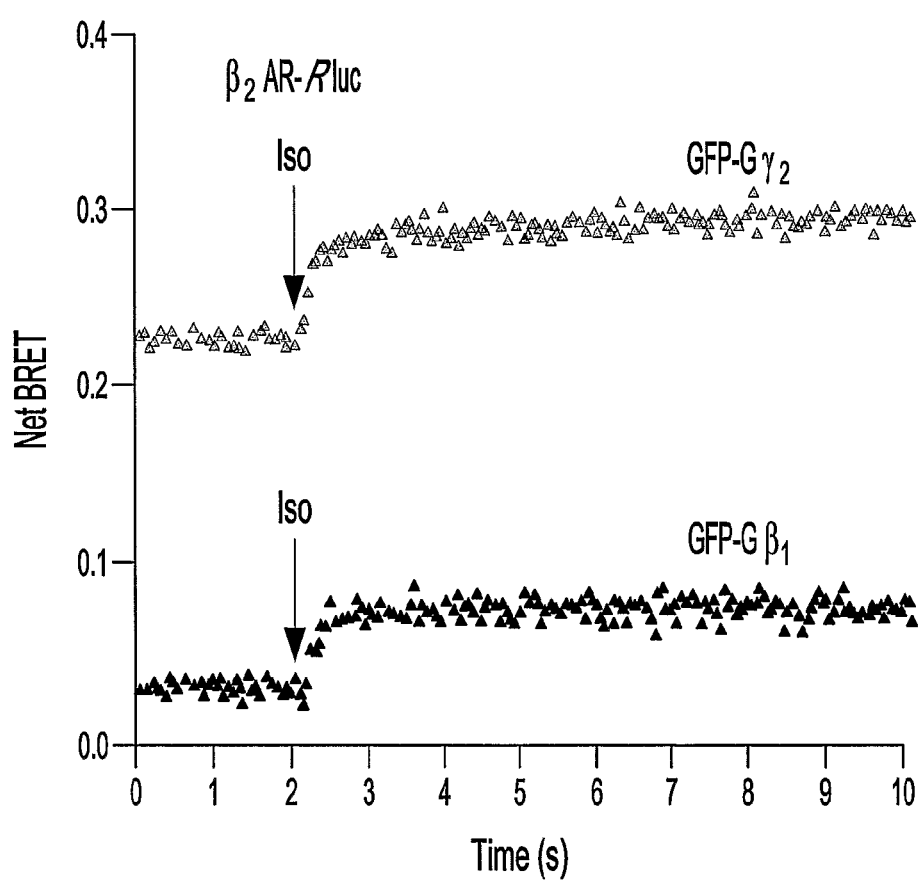
Figures 1, 40:
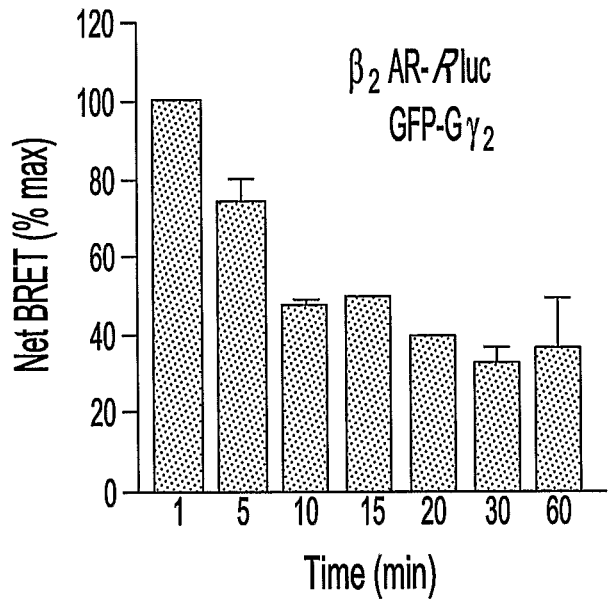
Figures 2, 40:
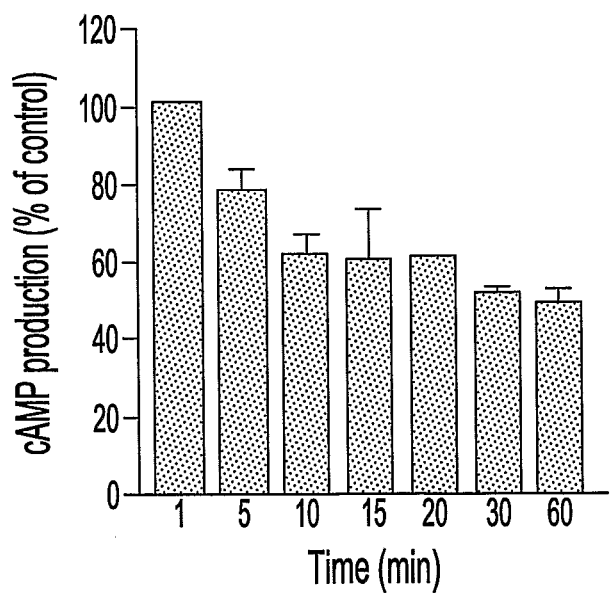

BRET Kinetics Reveal Millisecond Time-Scale G Protein Activation Followed by a Slower Desensitization The kinetics of Gβγ engagement by the receptor following agonist stimulation was then monitored using real time BRET measurements. As shown in FIG. 4a, the maximal increase in BRET between β2AR-Rluc and GFP10-Gβ or -Gγ occurred within the first second (t½~300 msec) after agonist addition. These kinetics are consistent with the very fast GPCR conformational activation switch determined by FRET in living cells[19]. The elevated BRET signal remained constant for at least 1 minute in the continued presence of the agonist (FIG. 11). However, the signal rapidly returned to basal values following the addition of the inverse agonist ICI-118551, indicating that the active conformation of the receptor is essential for the sustained engagement of Gβγ (FIG. 4b). The persistent BRET signal observed in the presence of an agonist can be reconciled with the classical view that a rapid dissociation of Gα and Gβγ from the receptor follows the initial recruitment of the heterotrimer by suggesting that the agonist triggers a new equilibrium between Gβγ-associated and -dissociated β2AR that results in a new steady state where the elevated BRET signal reflects a greater proportion of receptor being associated with Gβγ in the continued presence of agonist. Alternatively, the data may indicate that βγ does not readily dissociate from the receptor following activation.

To further explore the dynamics between Gαs and Gβ1γ2, constructs Rluc-Gβ1 and Gαs-GFP10 were used to assess the influence of β2AR activation on the Gα/βγ interaction by BRET. In the absence of β2AR activation, a basal BRET signal was detected between Rluc-Gβ1 and Gαs-GFP10 (FIG. 4c) consistent with the existence of a preassembled G protein heterotrimer. Addition of the β2AR-agonist induced a significant increase in BRET signal, most likely reflecting conformational changes within Gα and Gβγ complexes following receptor-mediated G protein activation.

Figures 1, 4E:
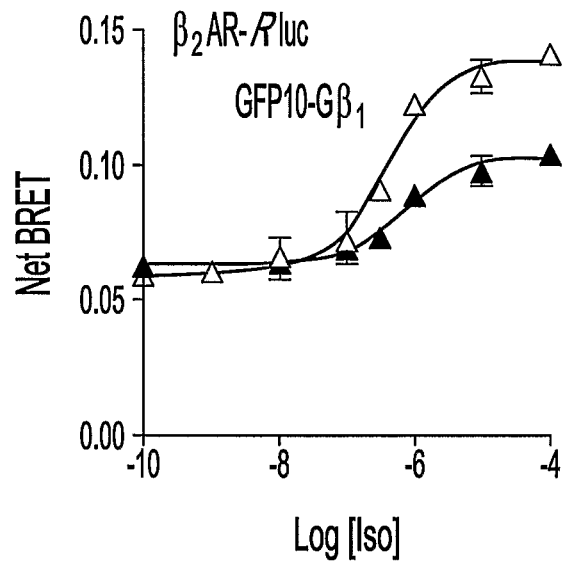
FIG. 4E: BRET measured in the presence of increasing concentrations of Iso in cells expressing β2AR-Rluc and GFP10-Gβ1 (FIG. 4E-1) or GFP10-Gγ2 (FIG. 4E-2), and pretreated (▲) or not (Δ) with 10 μM Iso for 1 hour. Data represent the mean±SEM of 3-4 independent experiments.
Figures 2, 4E:
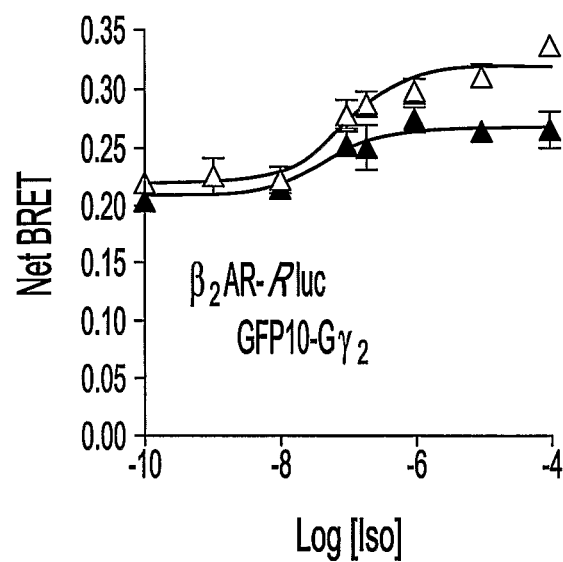

To assess whether reduction in the receptor-G protein coupling efficacy that follows sustained agonist-stimulation (desensitization) could be detected using the receptor-Gβγ interaction BRET-based assay, the effect of longer term agonist stimulation on the BRET detected between β2AR-Rluc and GFP10-Gγ2 was determined. Although the BRET signal was stable for at least 1 minute, sustained agonist exposure led to a time-dependent reduction in the BRET signal observed that reached 53% of the maximal BRET signal 10 minutes after the initial application of the stimulus (FIG. 4d, left panel). This progressive decrease in BRET most likely reflects the agonist-promoted desensitization of the receptor, since the loss of BRET signal over time paralleled the reduction in agonist-stimulated cAMP production (FIG. 4d, right panel). Similarly, the concentration-dependent increase in agonist-promoted BRET was considerably blunted in cells pretreated for 1 hour with the agonist isoproterenol (FIG. 4e). The assay also allows the reliable study of the kinetics of desensitization as it occurs in living cells. Indeed, when similar BRET experiments were conducted with the α2AAR, a receptor known to undergo slower desensitization[53], the loss of BRET signal between α2AAR-Rluc and GFP10-Gγ2 upon stimulation with the α2AAR agonist, UK14304, occurred with slower kinetics, decreasing by only 24% after 10 minutes (as compared with 53% for the β2AR) (FIG. 4f). The reduced BRET signal observed between the receptor and βγ during the desensitization process is consistent with the known reduced ability of the desensitized receptors to engage G proteins[54]. Whether this results from a reduced ability of the receptor to recruit G proteins or from a diminished conformational switch within a pre-assembled receptor/G protein complexes remains to be investigated.

The results presented here clearly establish receptor/G protein BRET assays as reliable real-time biosensors for receptor-mediated G protein activation in living cells.

In recent years, several sophisticated in vitro approaches, such as surface plasmon resonance[55] or flow cytometry[56], have been developed to measure real-time interactions between GPCRs and their cognate G proteins. Because they rely on the use of purified proteins, these methods permit the accurate determination of the kinetics and affinity of interactions between select members of the ligand-receptor-G protein ternary complex. However, because they are performed outside the natural environment of the cell, such techniques cannot integrate the possible regulatory influence of other cellular factors. Moreover, the immobilization of one of the partners on a cell surface may restrict its movements and influence the dynamics of the interaction. It follows that the real time BRET assay provides the first method allowing the direct kinetic measurement of the receptor/G protein interaction in their natural environment, the living cells.

The BRET-based approach allowed monitoring the direct interaction between GPCR-Rluc or -GFP10 and each of the individual components of the heterotrimeric G proteins (Gαs-GFP10, Gαi-Rluc, Gβ1-GFP10, Gγ2-GFP10). In addition, the selectivity of interaction between a receptor and a given Gα subunit can be indirectly assessed using the receptor/Gβ1 or receptor/Gγ2 sensors by assessing the ability of specific unmodified Gα isoforms to potentiate the agonist-promoted BRET responses. Based on these results, there is reason to believe that the selectivity of Gβ and Gγ isoforms can also be determined using the receptor/Gα sensor. This should prove to be an important aspect of the method, since establishing the selectivity of interaction between receptors and their cognate G protein isoforms has been a difficult task with currently available in vitro assays[57].

Extension of the invention: use of three resonance energy transfer (RET) technologies (BRET[1]+BRET[2]+FRET) in a unique assay for the detection of receptor-mediated G protein activation within three independent interactions in the receptor-G protein complex.

Advantage: the measurement of three different but related proteins interactions in a unique assay allows the determination of all aspects of a same biological phenomenon, the receptor-mediated G protein activation. This increases the opportunity to detect consequent modulated-BRET signals that reflect specific G protein activation mechanisms.

Proof of Principle:

I) Technological Basis

Resonance energy transfer technologies, BRET (Bioluminescence resonance energy transfer) or FRET (Fluorescence resonance energy transfer), rely on a common principle: the transfer of energy between a donor and an acceptor that share overlap in emission and excitation spectrum. Based on that concept, different generations of BRET/FRET have been conceived:

BRET[1] is resulting from an energy transfer between the bioluminescent energy donor *Renillia* Luciferase (Rluc), following degradation of its substrate Coelenterazine h ($\lambda$em=470 nm), and the fluorescent acceptor, Enhanced Yellow Fluorescent protein (EYFP) ($\lambda$exc=515 nm; $\lambda$em=528 nm).

BRET[2] is a modification of BRET[1] based on the use of another substrate of Rluc, with spectral properties different from that of coelenterazine h. Herein, the BRET[2] results from an energy transfer between the energy donor *Renillia* Luciferase (Rluc), following degradation of the substrate DeepBlueC ($\lambda$em=400 nm), and a different fluorescent acceptor (with compatible spectral properties to be excited), the Green Fluorescent protein (GFP[2]) ($\lambda$exc=395 nm; $\lambda$em=510 nm).

Because YFP and GFF[2] have different excitation and emission wavelengths, it should be easy to detect both resonance energy transfers in a unique assay, using these two energy acceptors (BRET[1]+BRET[2]) and their selective substrates as energy sources.

FRET is based on the transfer of energy between two fluorophores. Classically, FRET studies rely on CFP/EYFP donor/acceptor pairs. However, because GFP[2] has an emission spectrum overlapping exactly with the excitation wavelength of EYFP, these two fluorophores could be used as a donor and acceptor of energy respectively in a FRET assay.

Because BRET[1], BRET[2] and GFP[2]/EYFP-FRET all share common energy donors or acceptors, these three RET-based approaches were used to detect at the same time (i.e., in three independent interactions in the same assay).

II) Experimental Validation of a BRET[1]/BRET[2]/FRET-Assay

To validate this RET-assays combination, the interaction between the obligatory dimeric receptor GABAbR1-GABAbR2 and the heterotrimeric G protein was assessed.

Figures 1, 12:
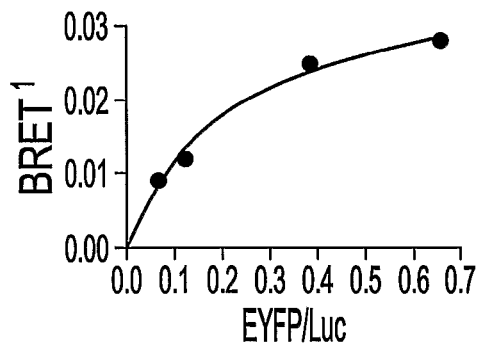
FIG. 12: $BRET^1$, $BRET^2$, FRET (FIG. 12-3) titration curves. HEK293T cells were co-transfected with $G\alpha_{i1}$-Rluc, GBR1-GFP2 and increasing amounts of GBR2-EYFP. $BRET^1$ (FIG. 12-1) and $BRET^2$ (FIG. 12-2) signals were detected after addition of DeepBlueC or Coelenterazine h, respectively, on the cells. $BRET^1$ and $BRET^2$ were measured using the Fusion-α and the modified TopCount (PerkinElmer), respectively. FRET signal was measured using the Flexstation (Molecular Devices).
Figures 2, 12:
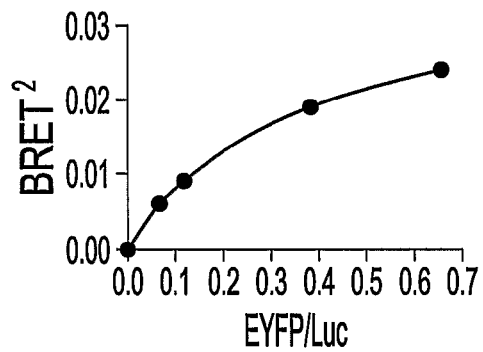
Figures 3, 12:
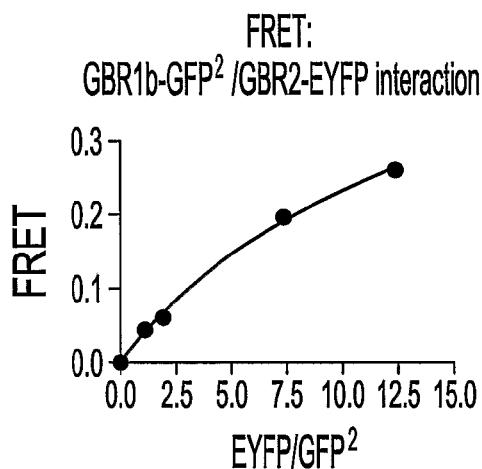
Figures 4, 12:
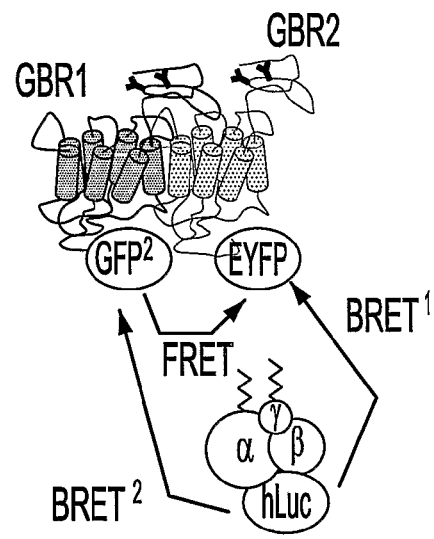

For that purpose, GABAbR1 (GBR1) and R2 (GBR2) receptors were tagged with GFP[2] and EYFP respectively, at their C-terminus (Cf. FIG. 12). FRET between GFP2 and EYFP was thus measured to detect dimerization of GABAbR1/GABAbR2 subunits.

G$\alpha_{i1}$ subunit was tagged with Rluc in its helical domain. Thus, we detected interaction of G$\alpha_{i1}$-Rluc with the GABAbR1-GFP2 using BRET2 while the interaction of G$\alpha_{i1}$-Rluc with GABAbR2-EYFP was followed using BRET[1].

HEK293T cells were co-transfected with a fixed amount of GBR1-GFP[2], G$\alpha_{i1}$-Rluc and G$\beta_1\gamma_2$ while increasing the level of GBR2-EYFP. As shown in FIG. 12, when cells were incubated with specific Rluc substrates (coelenterazine h or DeepBlueC for BRET) or excitated with a specific laser (for FRET), for all generation of RET-technologies, the energy transfer increased hyperbolically as a function of the GBR2-EYFP expression level, indicative of specific interactions between GBR1 and GBR2 receptor subunits as reflected by FRET, between G$\alpha_{i1}$-Rluc and GBR1-GFP10 as reflected by BRET[2], and finally between G$\alpha_{i1}$-Rluc and GBR2-EYFP as reflecting by BRET[1].

In conclusion, we demonstrate that it is feasible to measure three different protein interactions in a same population of transfected cells, by using proteins tagged with specific energy donors/acceptors amenable for concomitant BRET[1], BRET[2] and FRET measurements.

III) Application of BRET[1]/BRET[2]/FRET-Assay for Detection of Multiple Interactions in the Receptor/G$\alpha$/G$\beta\gamma$ Complex As it is currently designed, the single BRET-based biosensor, described previously in the present invention, that we have elaborated for receptor-mediated G protein activation, is solely based on the use of BRET[2] for the detection of individual protein-protein interactions in the receptor/G protein complex (G$\alpha$ or G$\beta$ or G$\gamma$ interaction with the receptor-G$\alpha$ and G$\beta$ interactions). Thus, measurement of all protein interactions occurring in the receptor/G protein complex necessities independent BRET assays. The BRET[1]/BRET[2]/FRET-assay presented above could then be advantageously be applied to the BRET-based receptor/G protein interaction assay for the detection of all the interactions in the receptor/G protein complex but in a unique assay.

Figures 1, 2, 3, 4, 13:
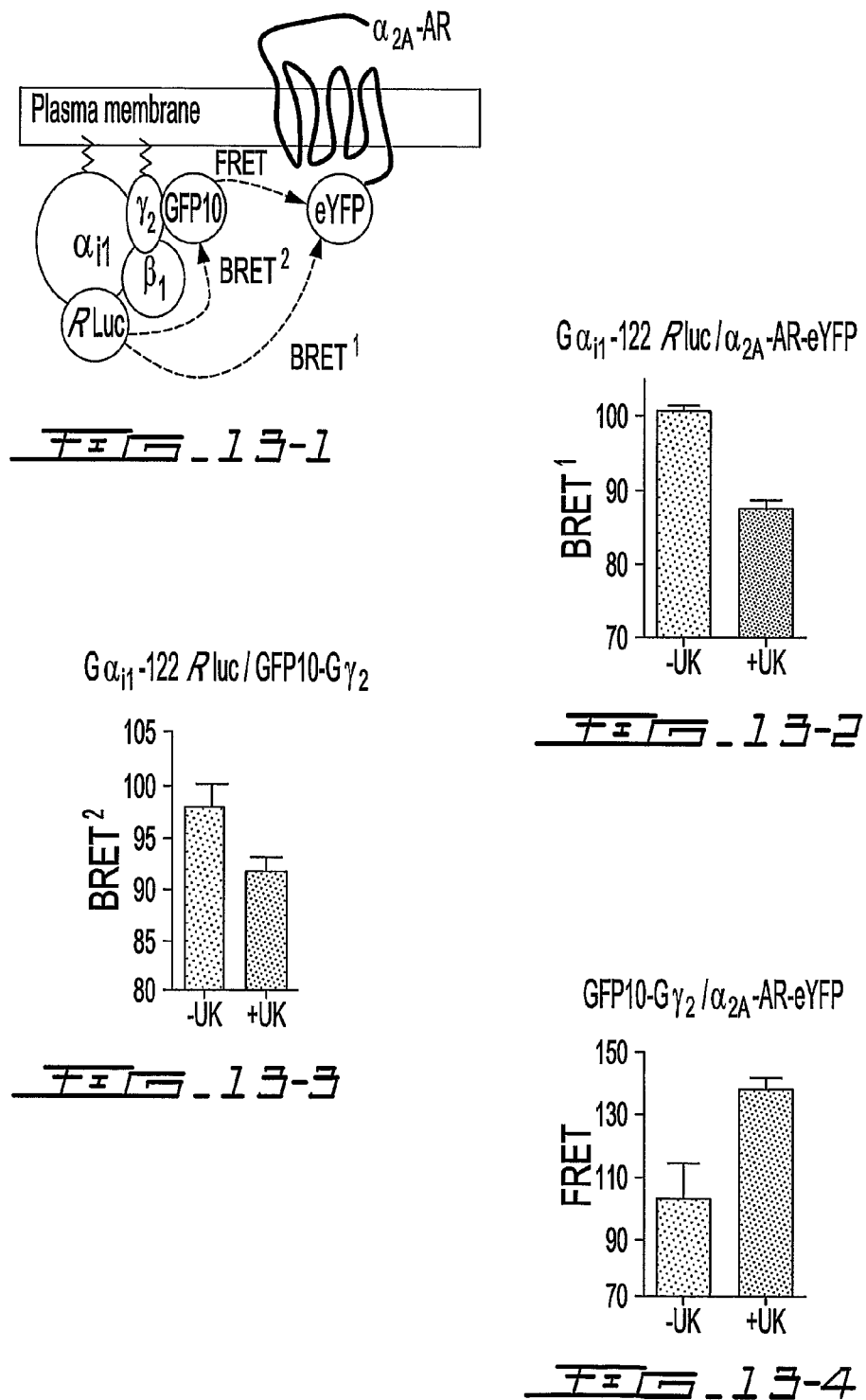
FIG. 13: HEK293T cells will be co-transfected with $G\alpha_i$122-Rluc, GFP10-$G\gamma_2$ together with $\alpha_{2A}$AR-eYFP. $BRET^1$ (detecting interactions between $G\alpha_i$122-Rluc and $\alpha_{2A}$AR-eYFP) and $BRET^2$ (detecting interactions between $G\alpha_i$122-Rluc and GFP10-$G\gamma_2$) signals were detected after addition of DeepBlueC or Coelenterazine h, respectively, on the cells. $BRET^1$ (FIG. 13-2) and $BRET^2$ (FIG. 13-3) signals were measured using the Fusion-α and the modified TopCount (PerkinElmer), respectively. FRET signal (FIG. 13-4) (detecting interactions between GFP10-$G\gamma_2$ and $\alpha_{2A}$AR-eYFP) was measured using the Flexstation (Molecular Devices).

FIG. 13 illustrates the idea behind an experiment where receptor-EYFP, G$\alpha$-Rluc and GFP[2]-G$\beta$ or -G$\gamma$ would be co-transfected all together. FRET signal would reflect interaction between receptor and G protein $\beta\gamma$ subunits (GFP[2]-G$\beta$ or -G$\gamma$ receptor-EYFP). BRET[1] would allow measurement of receptor/G$\alpha$ subunit (receptor-EYFP/G$\alpha$-Rluc) while interaction between G protein subunits would be followed by BRET[2] (G$\alpha$-Rluc/GFP[2]-G$\beta$ or -G$\gamma$).

Example 1

Figure 15B:
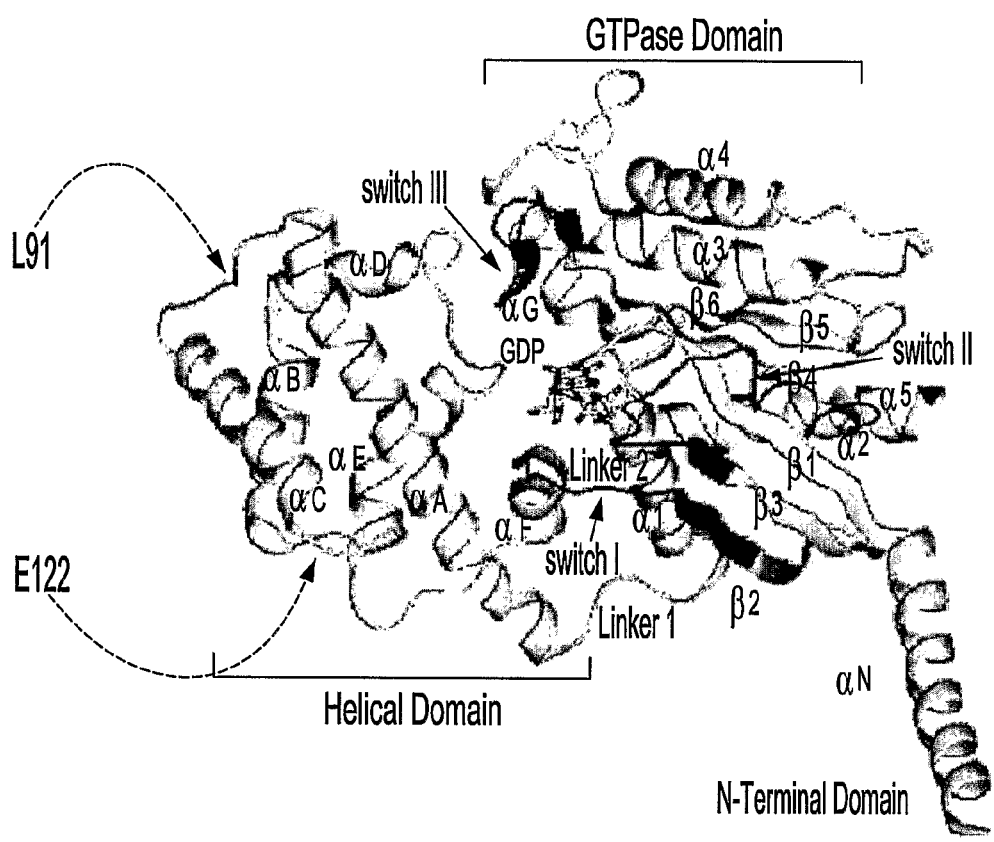
FIG. 15B: Overall architecture of Gα modified from Weng et al.[39], consisting of three major domains (the GTPase domain, the helical domain (connected by linker 1) and the N-terminal domain) and three switch regions (switch I, II, and III). Arrows indicate the different positions of the two main Rluc probes used in the study.
Figures 3, 16:
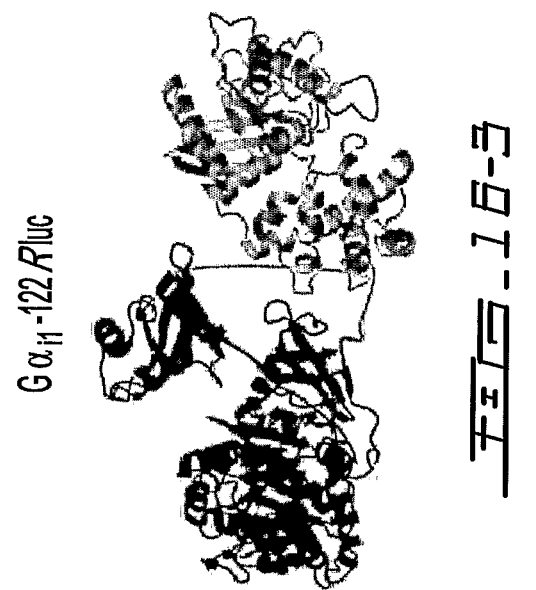
FIG. 16: View of the structures of Gαi1 (FIG. 16-1), Gαi1-91Rluc (FIG. 16-2) and Gαi1-122Rluc (FIG. 16-3). Schematic representation of $G\alpha_{i1}$ structure (light blue; PDB code 1GG2) fused or not to luciferase (Dark blue; PBD code 1LC1) in different positions within the protein, as indicated. The flexible linker, SGGGGS, used to fuse luciferase is shown in green. Structures were visualized by means of the software YASARA.
Figures 2, 16:
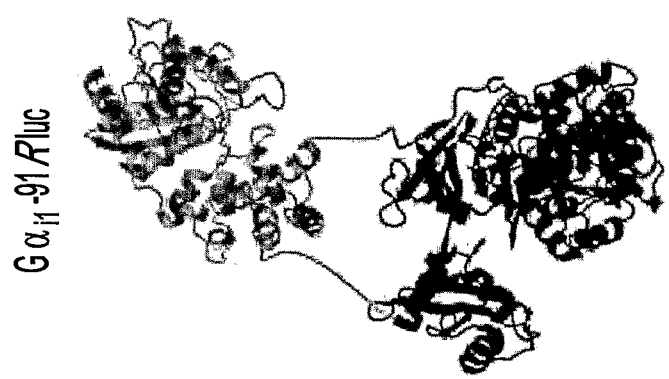
Figures 1, 16:
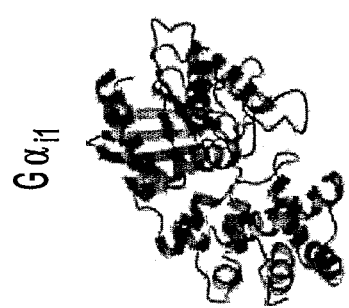

Configuration of the BRET Partners Used to Monitor Receptor-Mediated G Protein Activation To monitor the interactions between GPCRs and their cognate G proteins and among the G proteins subunits, BRET[1] and BRET[2] signals were measured between the different partners in living cells in the presence and absence of selective receptor ligands. Receptors, G$\alpha_{i1}$, G$\beta_1$ and G$\gamma_2$ were fused to BRET energy donor or acceptor (FIG. 15a). The receptors ($\alpha_2$AR, $\beta_2$AR and CRLR) were fused at their carboxyl tail to the *Renilla reniformis* luciferase (Rluc) or *Aequorea victoria* green fluorescent proteins (GFP2, GFP10 or YFP, depending on the partners considered). G$\beta_1$ and G$\gamma_2$ were fused to their N-terminus to either Rluc or GFP10. For G$\alpha_{i1}$, two different constructs were engineered so as to allow a better monitoring of the relative movements of the partners. Rluc was inserted in connecting loops located at opposite sides within the helical domain of the protein (FIG. 15b). One of the insertion site between L91 and K92 in the loop connecting helices A and B (G$\alpha_{i1}$-91Rluc) has previously been described[6], whereas the second, located between E122 and L123 in the loop connecting helices B and C ($G\alpha_{i1}$-122Rluc), is presented here for the first time. The same flexible linker (SGGGGS) was used at both N- and C-terminus of the RLuc for the two positions. (Structures are represented in FIG. 16.)

Figures 1, 17:
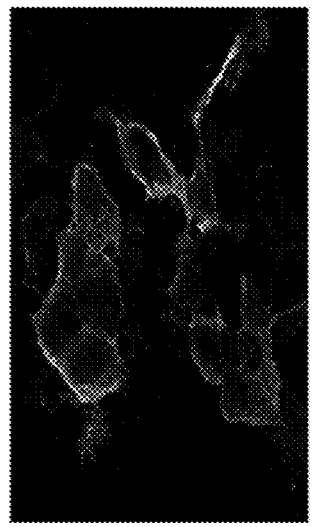
FIG. 17: Plasma membrane targeting of Gαi1-91Rluc (FIG. 17-2) and $G\alpha_{i1}$-122Rluc (FIG. 17-5) fusion proteins. HEK293T cells were co-transfected with either $G\alpha_{i1}$-91Rluc or $G\alpha_{i1}$-122Rluc along with HA-GBR2 (used as a plasma membrane indicator)(FIGS. 17-1 and 17-4). Localization of $G\alpha_{i1}$-91Rluc or $G\alpha_{i1}$-122Rluc and HA-GBR2 was assessed by confocal immunofluorescence microscopy, as described in material and methods and shows co-localization of $G\alpha_{i1}$-91Rluc or $G\alpha_{i1}$-122Rluc and HA-GBR2 at the plasma membrane.
Figures 2, 17:
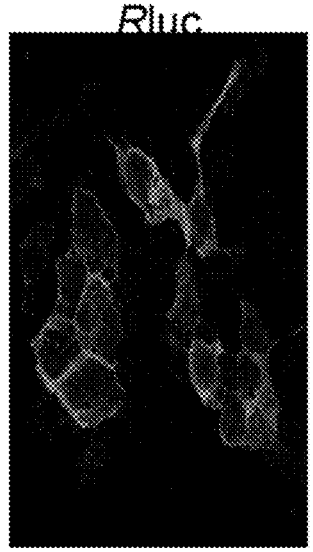
Figures 3, 17:
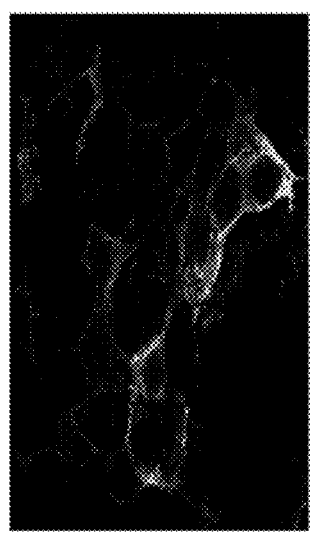
Figures 4, 17:
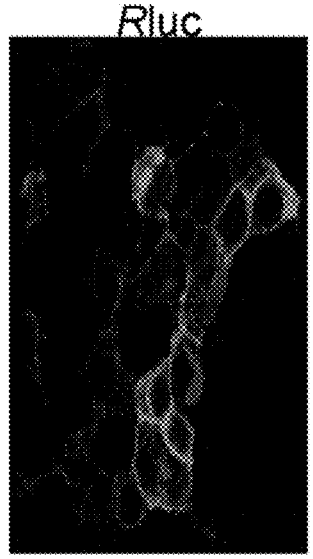
Figure 18:
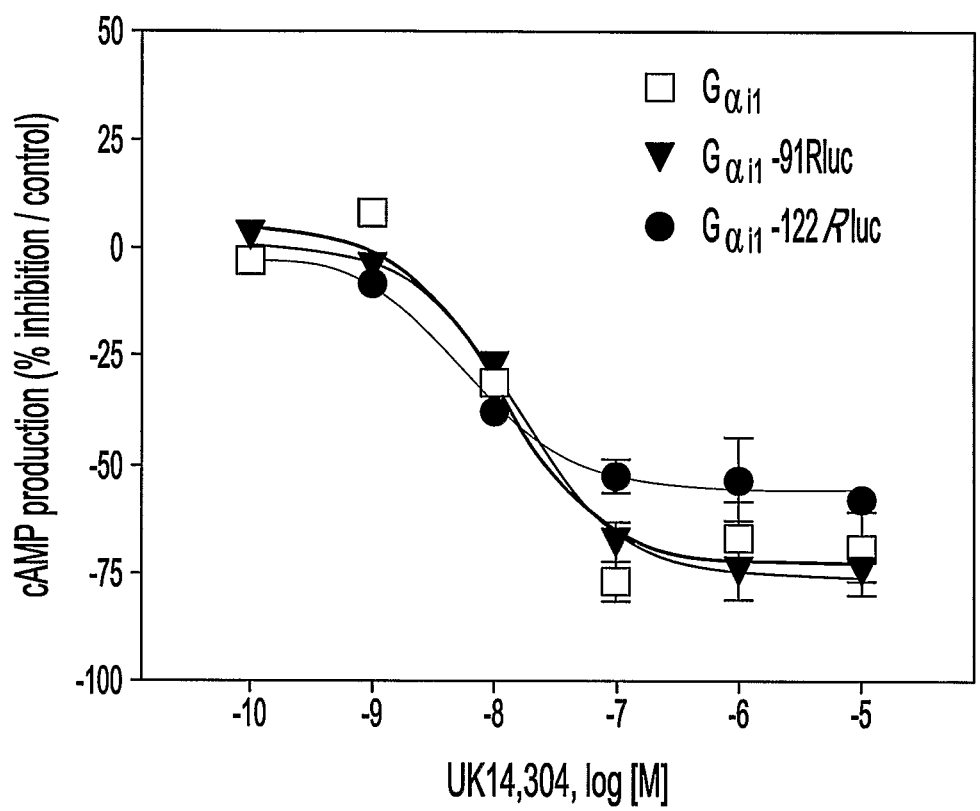
FIG. 18: Functionality of Gαi1-91Rluc and Gαi1-122Rluc fusion proteins. Inhibition of cAMP production in HEK293T cells expressing $\alpha_{2A}$AR-eYFP and either Gαi1, Gαi1-91Rluc or Gαi1-122Rluc was measured in the presence of increasing concentrations of UK14,304. Data are expressed as percentage decrease of cAMP level relative to control and represent the mean±S.E.M. of 4 independent experiments. No inhibition of the cAMP production could be observed in the absence of co-transfected Gαi.
Figures 3, 20:
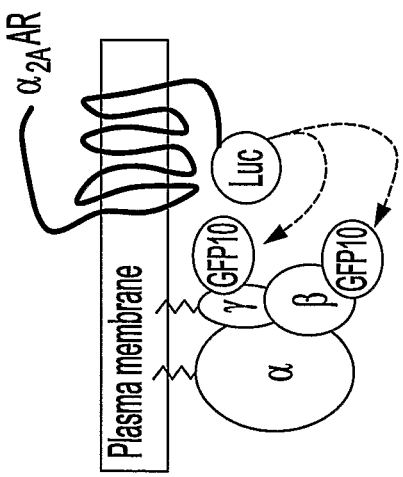
Figures 2, 20:
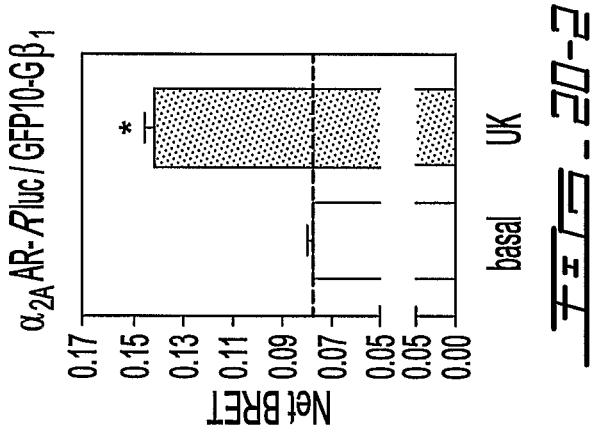
Figures 1, 20:
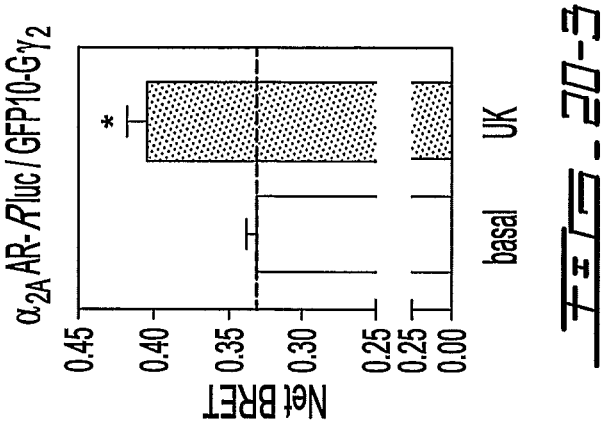
Figures 6, 20:
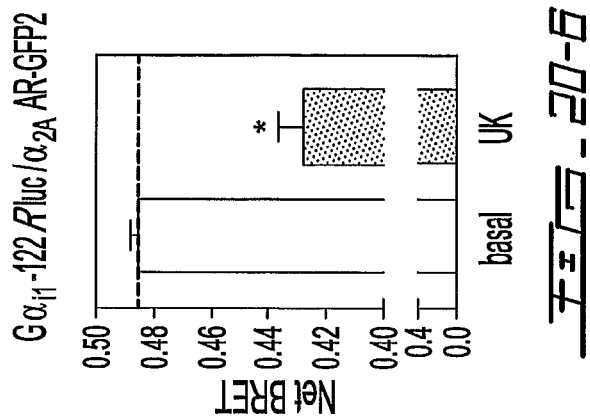
Figures 5, 20:
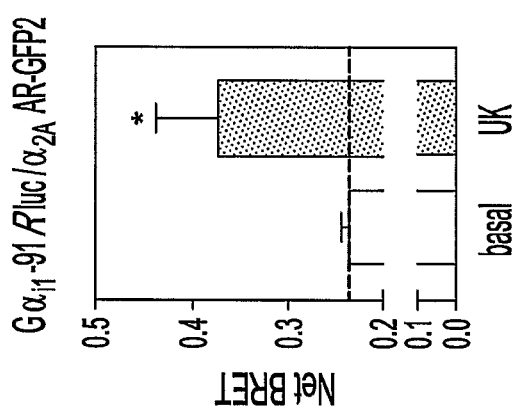
Figures 4, 20:
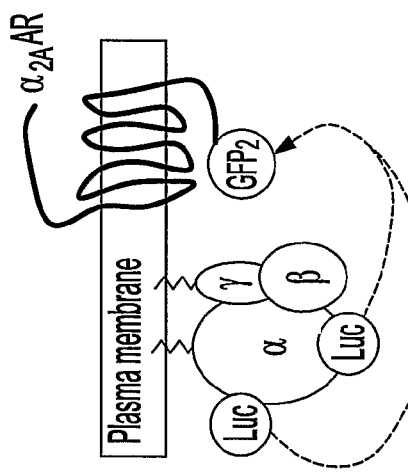

The receptor fusion proteins are functional, as reflected by their ability to bind their selective ligands and to regulate adenylyl cyclase activity (data not shown). As previously reported[8], the attachment of Rluc or GFPs to the N terminus of both $G\beta_1$ and $G\gamma_2$ constructs did not affect their targeting to the plasma membrane or their ability to activate the G protein-gated inward rectifying K+ channel (data not shown). Similarly to what was previously found for the insertion of a GFP at position 91[6], the introduction of Rluc at either position 91 or 122 of $G\alpha_{i1}$ was also well tolerated. Immunofluorescence confocal microscopy revealed that both $G\alpha_{i1}$-91Rluc and $G\alpha_{i1}$-122Rluc were properly targeted to the plasma membrane when co-expressed with their complementary $G\beta_1\gamma_2$ subunits (FIG. 17). They were also found to be functional, as illustrated by their ability to enhance the $\alpha_{2A}$AR-promoted inhibition of adenylyl cyclase activity (FIG. 18).

The configurations of the BRET partners used to probe the receptor-mediated G protein activation are illustrated in FIG. 19. The interactions between the receptors and $G\beta\gamma$ subunits were measured in cells co-expressing receptor-Rluc and GFP10-$G\beta_1$ (FIG. 19a) or GFP10-$G\gamma_2$ (FIG. 19b) while receptor-$G\alpha$ interactions were monitored in cells co-expressing receptor-GFP and $G\alpha_{i1}$-91Rluc (FIG. 19c) or $G\alpha_{i1}$-122Rluc (FIG. 19d). For the interactions among the G protein subunits, BRET was measured between GFP10-$G\gamma_2$ and $G\alpha_{i1}$-91Rluc (FIG. 19e) or $G\alpha_{i1}$-122Rluc (FIG. 19f in the presence of untagged receptors. In all cases, tagged-G protein subunits were co-expressed with their complementary untagged subunits to maintain stoichiometric expression of the three subunits in order to assure their proper targeting to the plasma membrane[8].

Example 2

Figures 1, 20:
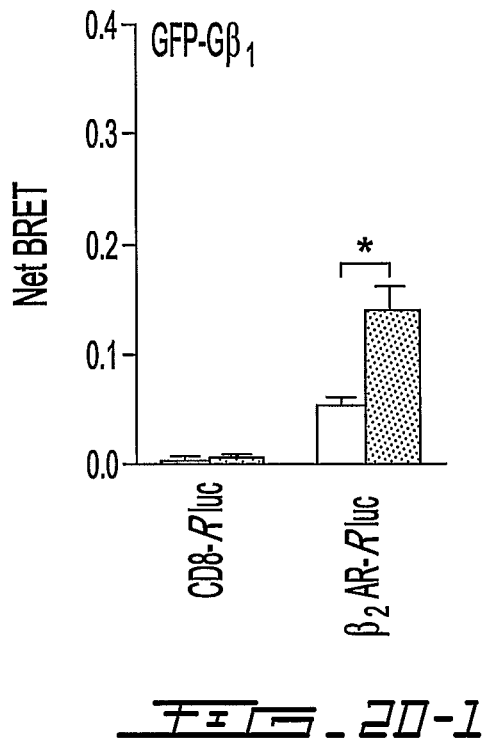
FIG. 20: BRET measurements of GPCRs and $G\alpha_{i1}β_1γ_2$ interactions in living cells. BRET was measured in cells coexpressing Rluc-tagged $\alpha_{2A}$AR ($\alpha_{2A}$AR-Rluc) with either GFP10-$Gβ_1$ or GFP10-$Gγ_2$ (FIGS. 20-1, 20-2 and 20-3) or in cells coexpressing GFP2-tagged $\alpha_{2A}$AR ($\alpha_{2A}$AR-GFP2) with either $G\alpha_{i1}$-91Rluc or $G\alpha_{i1}$-122Rluc (FIGS. 20-4, 20-5 and 20-6), and stimulated (black) or not (white) with 10 μM UK14,304. Data represent the mean±S.E.M. of 3-4 independent experiments. *, P<0.05.
Figures 2, 20:
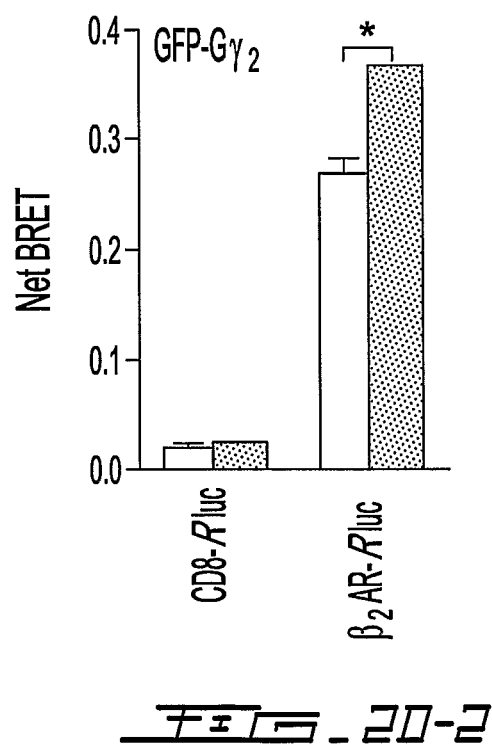
Figure 21:
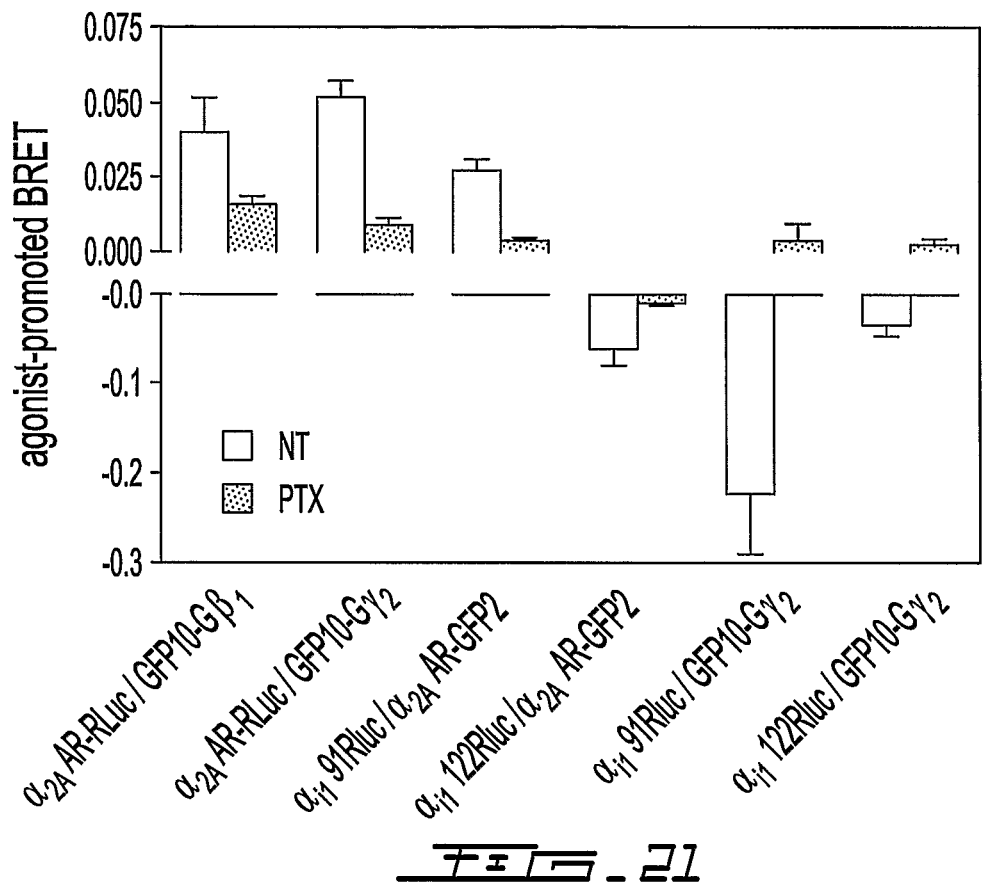
FIG. 21: Pertussis toxin-sensitivity of receptor-mediated G protein activation. BRET measured in the absence or presence of UK14,304 in cells coexpressing α2AAR-Rluc in the presence of either GFP10-Gβ1 or GFP10-Gγ2, or in cells expressing Gαi1-91Rluc or Gαi1-122Rluc with either α2AAR-GFP2 or GFP10-Gγ2, as indicated, and pretreated (PTX) or not (NT) with pertussis toxin during 16 h at 37° C. Results are expressed as the difference in BRET signal observed in the presence and absence of ligand and represent the mean±s.e.m. of 4 independent experiments, each performed in duplicate.

Receptor-Ligand Binding Promotes Conformational Rearrangement within Receptor/G Protein Complexes BRET[2] was monitored between the human $\alpha_{2A}$-adrenergic receptor ($\alpha_{2A}$AR-Rluc or $\alpha_2$AR-GFP2) and each of the G protein subunits (GFP10-$G\beta_1$; GFP10-$G\gamma_2$; $G\alpha_{i1}$-91Rluc or $G\alpha_{i1}$-122Rluc). As shown in FIG. 20, a basal BRET signal was detected in all cases, indicative of a constitutive receptor-$G\alpha\beta\gamma$ complex that may reflect pre-association[8]. The specificity of this interaction, was confirmed by the observation that no significant signal was detected between a form of the transmembrane protein CD8 fused to Rluc or GFP2 at its C-terminus[8] and any of the GFP2 or Rluc tagged-G protein subunits (data not shown). Stimulation of the receptor with the full agonist, UK14,304, significantly increased the BRET detected for the $\alpha_{2A}$AR-Rluc/GFP10-$G\beta_1$, $\alpha_{2A}$AR-Rluc/GFP10-$G\gamma_2$ and $G\alpha_{i1}$-91Rluc/$\alpha_{2A}$AR-GFP2 pairs (FIG. 20a). In contrast, the BRET was significantly reduced by the agonist stimulation for the $G\alpha_{i1}$-Rluc122/$\alpha_{2A}$AR-GFP2 pair (FIG. 20a). In all cases, the changes in BRET signals were blocked by a pre-treatment with pertussis toxin indicating that they reflected receptor-mediated G protein activation (FIG. 21).

Figures 1, 22:
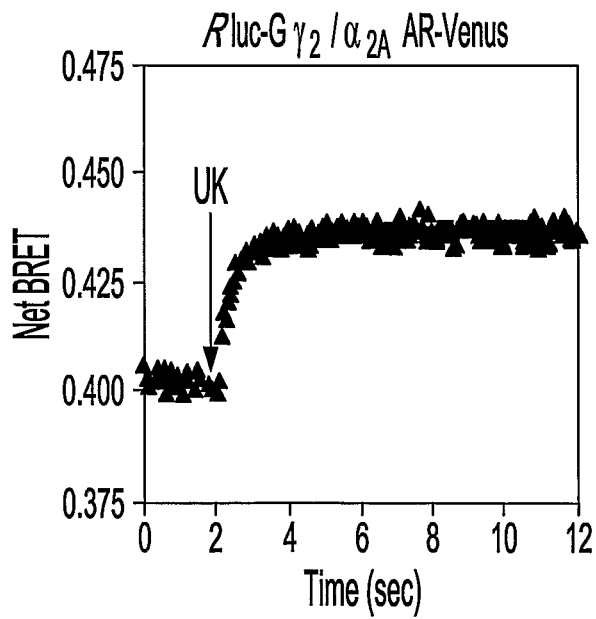
FIG. 22: BRET measured every 0.05 s for 12 s in cells expressing $\alpha_{2A}$AR-Venus with either Rluc-$Gγ_2$ (FIG. 22-1), or $G\alpha_{i1}$-91Rluc (FIG. 22-2) or $G\alpha_{i1}$-122Rluc (FIG. 22-3). UK14,304 (10 μM) was injected 2 s after the beginning of the readings. Data are representative of 3-4 experiments, each performed in quadruplicate.
Figures 2, 22:
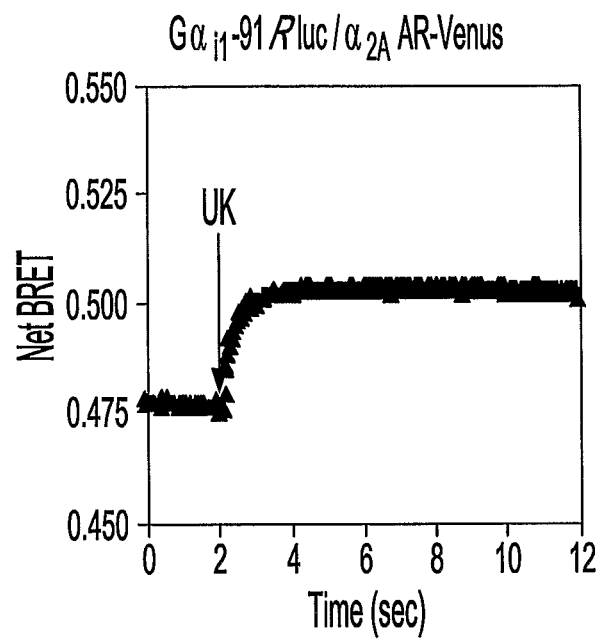
Figures 3, 22:
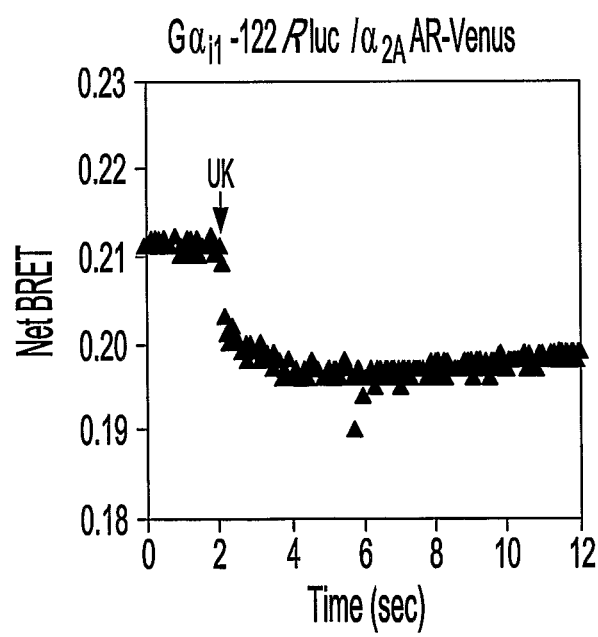
Figures 1, 23A:
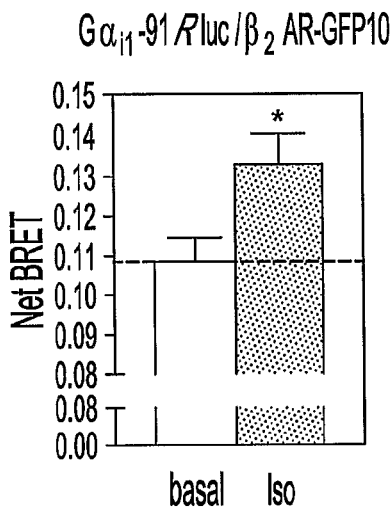
Figures 2, 23A:
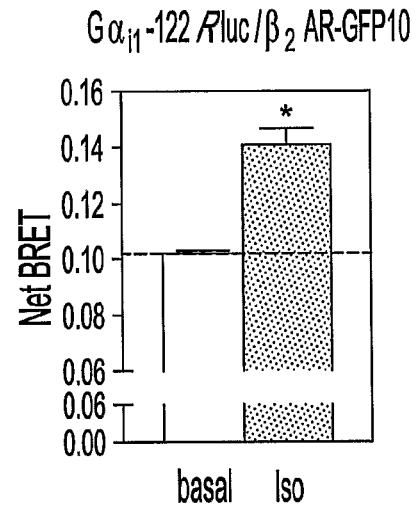
Figures 1, 23B:
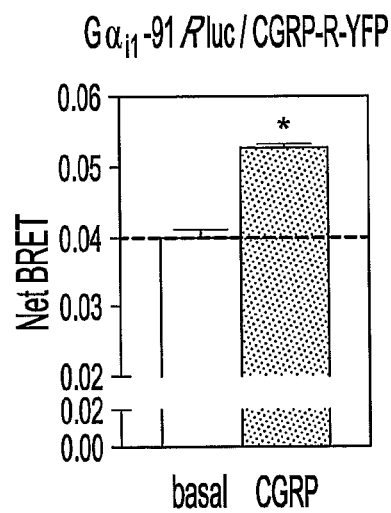
Figures 2, 23B:
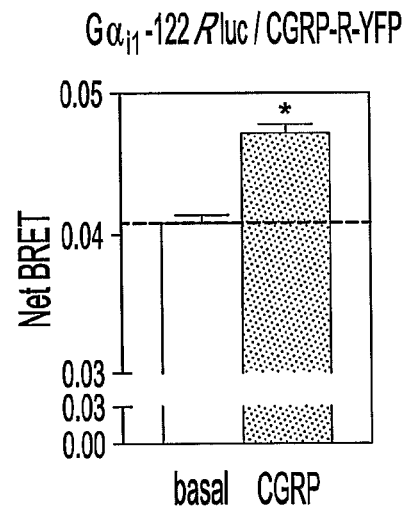

The kinetics of agonist-promoted changes were then assessed by monitoring in real time the evolution of the BRET[1] signal between $\alpha_{2A}$AR-Venus and either $G\alpha_{i1}$-91Rluc, $G\alpha_{i1}$-122Rluc or Rluc-$G\gamma_2$. As shown in FIG. 22, constitutive BRET signals are stable under basal conditions but addition of the agonist UK14,304, promoted rapid increases in the BRET for the Rluc-$G\gamma_2$/$\alpha_{2A}$AR-Venus and $G\alpha_{i1}$-91Rluc/$\alpha_{2A}$AR-Venus pairs and a similarly rapid decrease in BRET[1] for the $\alpha_{2A}$AR-Venus/$G\alpha_{i1}$-122Rluc pair. In all cases, the BRET levels reached following agonist stimulation remained constant for at least 12 seconds with no evidence of a return toward basal values, indicating that, at any given time during the early phase of activation, a significant fraction of the receptor is engaged in a ternary (agonist-receptor-G protein) complex. These results are difficult to reconcile with the classical model suggesting that a rapid dissociation of the G protein subunits from the receptors follows their initial agonist-promoted engagement. Indeed, in such a model the changes in BRET signals should be independent of the relative position of the energy donor on the $G\alpha$ subunit. It follows that the opposite BRET changes detected when using $G\alpha_{i1}$-122Rluc or $G\alpha_{i1}$-91Rluc as the energy donor most likely reflect an agonist-promoted conformational rearrangement within the receptor-$G\alpha\beta\gamma$ complex that is differentially sensed depending on the position of the energy donor. It may alternatively be suggested that the agonist-modulated BRET signal reflects the equilibrium between the association and dissociation phases of the activation cycle and that the position of the tags could affect the kinetics of the cycle. For instance, the GFP10-$G\beta_1$, GFP10-$G\gamma_2$ and $G\alpha_{i1}$-91Rluc probes could detect the association, whereas $G\alpha_{i1}$-122Rluc could detect the dissociation. This is, however, unlikely since both $G\alpha_{i1}$-91Rluc and $G\alpha_{i1}$-122Rluc led to an increase in BRET signal following the activation by two other GPCRs, the human $\beta_2$-adrenergic receptor ($\beta_2$AR-GFP10) (FIG. 23a) and the human calcitonin gene related peptide receptor (CGRP-R=CRLR-YFP+RAMP1) (FIG. 23b). The directions of the BRET changes are therefore not a reflection of intrinsic kinetic properties of $G\alpha_{i1}$-91Rluc and $G\alpha_{i1}$-122Rluc but rather appear to reflect specific conformational rearrangements that are differentially sensed by the two positions of the BRET partners.

Figure 24:
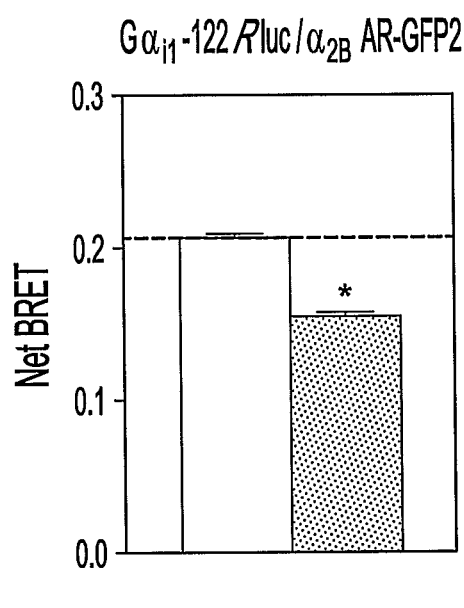
FIG. 24: BRET measurements of α2BAR and Gαi1 interaction in living cells. BRET measured in cells coexpressing Gαi1-122Rluc and α2BAR-Rluc, and stimulated (black) or not (white) with 10 μM Dexmedetomidine. Data represent the mean±s.e.m. of 3 independent experiments. *, P<0.05.

The observation that the BRET between receptors and $G\alpha_{i1}$-122Rluc varied in opposite directions following activation depending on the receptor considered further indicates that they reflect relative movements between the carboxyl tail of the receptor and the helical domain of $G\alpha$. The different orientation of the change observed for the $\alpha$AR when compared to the $\beta$AR and the CRLR is not surprising given the much shorter carboxyl tail of the $\alpha$AR (23 aa compared to 87 and 78 respectively). Consistent with this interpretation, a decrease in BRET was also observed between another receptor with a short tail the short tail, the $\alpha$AR-GFP2 and $G\alpha$-122Rluc (FIG. 24).

The effect of a panel of $\alpha_{2A}$AR-selective ligands on the receptor/G protein BRET[2] signals was investigated next. As shown in FIG. 25, qualitatively similar patterns of modulation were observed when the molecules were tested on the $\alpha_{2A}$AR-Rluc/GFP10-$G\beta_1$, $\alpha_{2A}$AR-Rluc/GFP10-$G\gamma_2$ or $\alpha_{2A}$AR-GFP2/$G\alpha_{i1}$-91Rluc. The partial agonists clonidine and dexmedetomidine promoted partial increase in BRET when compared with that induced by the full agonist UK14, 304, whereas the antagonists yohimbine and RX821002 had little or no effect. Pretreatment with RX821002 completely blocked the UK14,304-promoted BRET increase, further confirming the pharmacological specificity of the modulations observed. When considering the $\alpha_{2A}$AR-GFP2/$G\alpha_{i1}$-122Rluc pair (FIG. 23), all compounds tested promoted significant decreases in BRET, UK14,304 and dexmedetomidine, leading to the larger responses. The observation that not only the agonists but also the antagonists RX821002 and yohimbine promoted a decrease in the BRET between the receptor and $G\alpha_{i1}$-122Rluc further confirms that the observed reduction in BRET does not necessarily reflect a dissociation of the G protein from the receptor but most likely a conformational change within the complex since antagonists would not be predicted to promote G protein dissociation.

Example 3

Ligand-Promoted Conformational Changes within Preformed Receptor/Gαβγ Complexes The following experiments were designed to determine whether the agonist-promoted structural reorganization of the receptor/G protein complex occurred as a result of an active recruitment of the G proteins to the receptor. Since an active recruitment presupposes that agonist stimulation increases the affinity of the receptor for the G protein subunits, BRET titration assays between $\alpha_{2A}$AR-Rluc and GFP10-Gβ$_1$ or GFP10-Gγ$_2$ and between $G\alpha_{i1}$-91Rluc or $G\alpha_{i1}$-122Rluc and $\alpha_{2A}$AR-GFP2 were carried out in the presence and absence of UK14,304. BRET$_{50}$ (the GFP/Rluc ratio leading to 50% of the maximal BRET signal) derived from such titration curves is used as relative indicator of the affinity between partners[23, 24].

Figures 1, 26A:
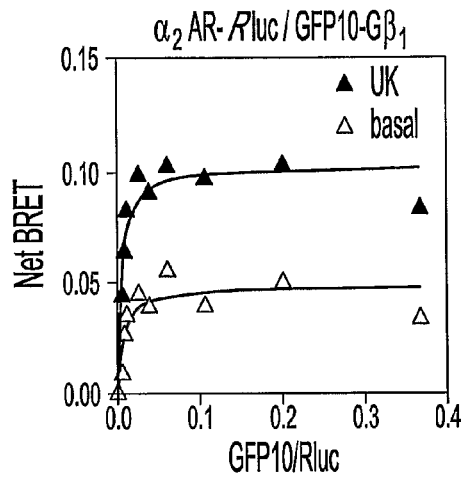
Figures 2, 26A:
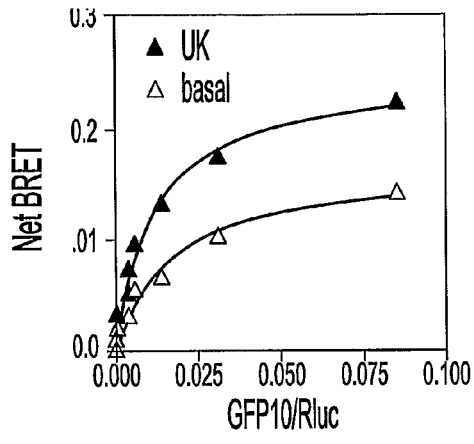
Figures 3, 26A:
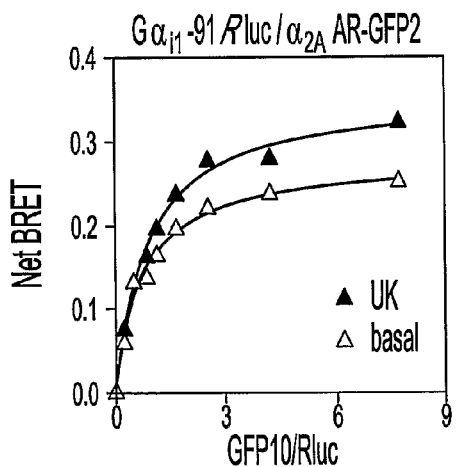
Figures 4, 26A:
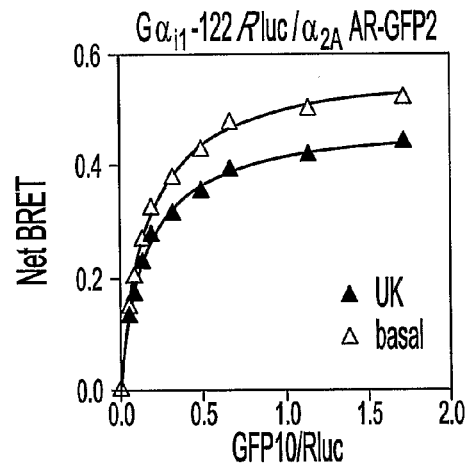
Figures 1, 26B:
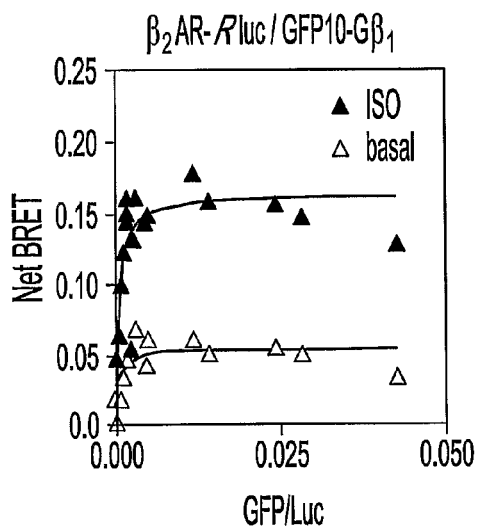
Figures 2, 26B:
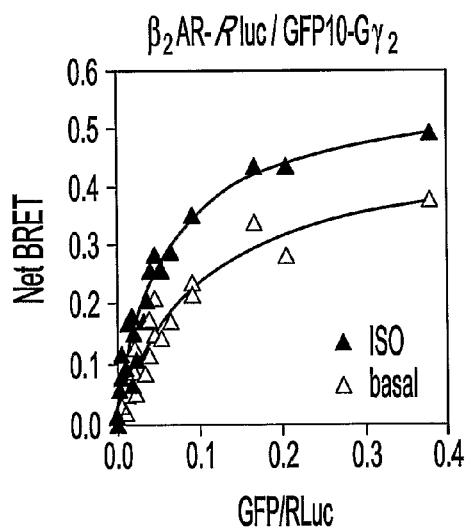
Figure 26C:
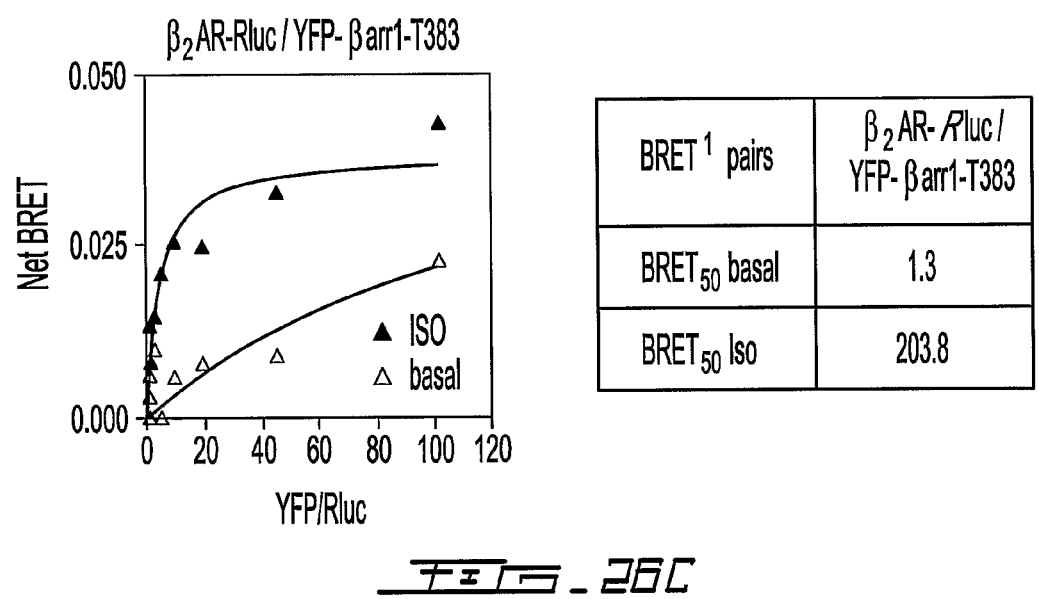
FIG. 26: Assessment of the dynamic nature of receptor/Gα$_{i1}$β$_1$γ$_2$ interactions. (a-c) BRET titration curves. BRET was measured in cells expressing a fixed amount of the indicated Rluc-tagged constructs and increasing amounts of the indicated GFP-tagged protein, and treated (▲) or not (Δ) with 10 μM UK14,304 (α$_{2A}$AR) (FIGS. 26A-1-4) or Iso (β$_2$AR) (FIGS. 26B-1-2, FIG. 26C). GFP/Rluc ratios leading to 50% of the maximal BRET (BRET$_{50}$) are presented in the tables. (d) Western blots illustrating the co-immunoprecipitation of β$_2$AR-Rluc with both GFP10-Gβ$_1$ (FIG. 26D-1) or GFP10-Gγ$_2$ (FIG. 26D-2). Co-immunoprecipitations were carried out in the presence or absence of 10 μM Iso. In parallel, control experiments were carried out in cells transfected only with GFP10-Gβ$_1$ or GFP10-Gγ$_2$. Data shown are representative of 3 independent experiments.
Figures 1, 26D:
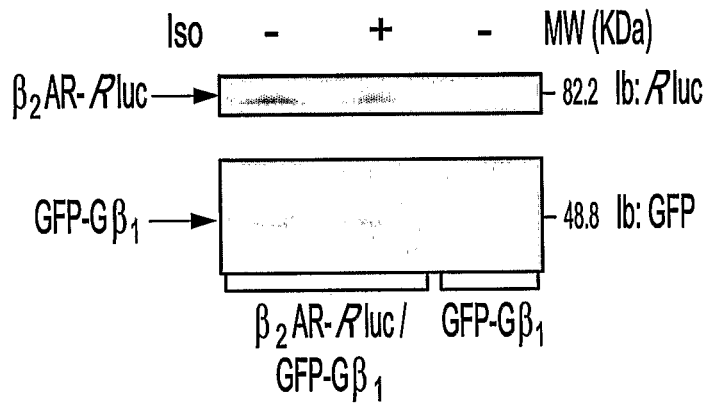
Figures 2, 26D:
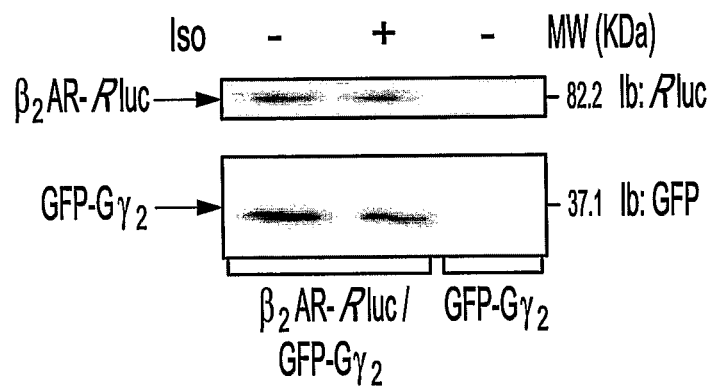

As shown in FIG. 26a, agonist treatment led to an increase ($\alpha_{2A}$AR-Rluc/GFP10-Gβ$_1$, /GFP10-Gγ$_2$ or $G\alpha_{i1}$-91Rluc/$\alpha_{2A}$AR-GFP2) or a decrease ($G\alpha_{i1}$-122Rluc/$\alpha_{2A}$AR-GFP2) of the maximal BRET but did not affect the BRET$_{50}$, indicating that receptor activation did not influence the relative affinity of the receptor for Gα, Gβ or Gγ (see table in FIG. 26a). This is not unique to the $\alpha_{2A}$AR since similar results were obtained when assessing the relative affinity between β$_2$AR-Rluc and GFP10-Gβ$_1$ or GFP10-Gγ$_2$ (FIG. 26b). The lack of change in the BRET$_{50}$ observed between the receptor and the G protein subunits contrasts with the significant agonist-promoted decrease in BRET$_{50}$ observed when assessing the recruitment of YFP-βarrestin-1-383T[25] to the β$_2$AR-Rluc (FIG. 26c), thus confirming that an active recruitment can be detected by a leftward shift of the BRET titration curve. The lack of such a shift in the BRET titration curves between the receptors and Gα, Gβ or Gγ subunits suggests that a significant fraction of the receptor and Gαβγ exists as a preformed complex which is subject to structural rearrangements upon ligand binding. The existence of a pre-assembled receptor/G protein complex that undergoes conformational rearrangements upon receptor activation is supported by the observation that Gβ$_1$ and Gγ$_2$ can be co-immunoprecipitated with β$_2$AR in the absence of agonist stimulation and that the extent of association was not affected by receptor activation (FIG. 26d). Altogether, this data does not support active agonist-dependent recruitment of Gαβγ to the receptor and may be more consistent with a model whereby agonist binding induces conformational changes within a pre-existing receptor/Gβγ complex.

Example 4

Receptor-Promoted Conformational Rearrangement in Heterotrimeric Gαβγ Protein Complex The effect of receptor activation was then assessed on the Gα/Gβγ interaction in cells co-expressing GFP10-Gγ$_2$ and either $G\alpha_{i1}$-91Rluc or $G\alpha_{i1}$-122Rluc in the presence of untagged $\alpha_{2A}$AR (FIG. 27). The full $\alpha_{2A}$AR agonist, UK14,304, promoted a reduction of BRET detected between both $G\alpha_{i1}$-91Rluc or $G\alpha_{i1}$-122 Rluc and GFP10-Gγ$_2$ (FIG. 27a). These BRET changes were abolished by a treatment with pertussis toxin confirming that they reflected G protein activation (FIG. 21). The similar modulations obtained with the two $G\alpha_{i1}$-Rluc constructs in the $G\alpha_{i1}$/Gγ$_2$ interaction contrast with the effect that the distinct position of the Rluc-tag had on the BRET signals detected when considering the $\alpha_{2A}$AR/$G\alpha_{i1}$ interaction (see previous section). To exclude that the dependency on the $G\alpha_{i1}$ tag position observed for the $G\alpha_{i1}$/$\alpha_{2A}$AR (FIG. 20) but not the $G\alpha_{i1}$/Gγ$_2$ (FIG. 27a) interaction could result from different experimental conditions, advantage was taken of the possibility of detecting BRET$^1$ and BRET$^2$ concomitantly in the same cells[26]. For this purpose, $G\alpha_{i1}$-91Rluc, $\alpha_{2A}$AR-Venus and GFP10-Gγ$_2$ were co-expressed and the two BRET signals were detected following the addition of the luciferase substrates, coelenterazine H or Deep-BlueC, for BRET$^1$ and BRET$^2$, respectively. As shown in FIG. 27b, activation of the receptor with UK14,304 led to an increase in the BRET between $G\alpha_{i1}$-91Rluc and $\alpha_{2A}$AR-Venus but a decrease in BRET$^2$ between $G\alpha_{i1}$-91Rluc and GFF$_{10}$-Gγ$_2$, confirming the results obtained when the two interactions were monitored independently.

Figures 3, 27A:
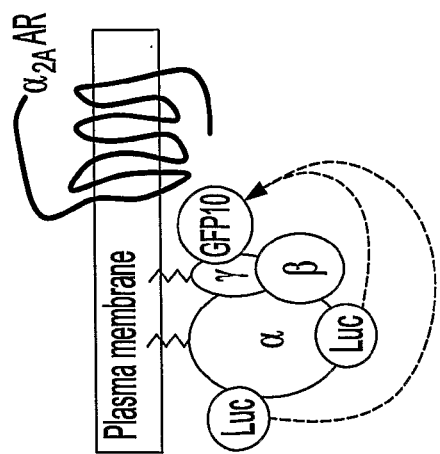
FIG. 27A: BRET measured in cells coexpressing either Gα$_{i1}$-91Rluc (FIG. 27A-2) or Gα$_{i1}$-122Rluc (FIG. 27A-3) with GFP10-Gγ$_2$ and α$_{2A}$AR, and stimulated (black) or not (white) with 10 μM UK14,304. Data represent the mean±s.e.m. of 3-4 independent experiments. *, P<0.05. Shown schematically in FIG. 27A-1.
Figures 2, 27A:
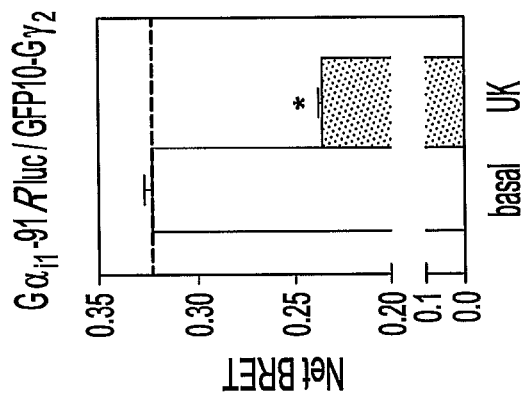
Figures 1, 27A:
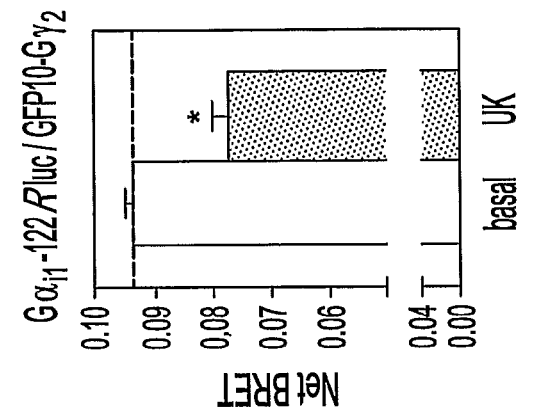
Figures 1, 27C:
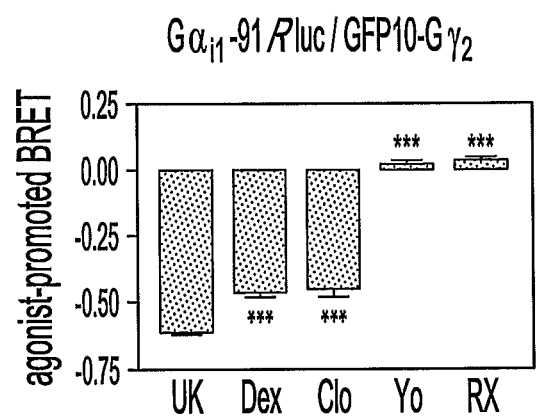
FIG. 27C: BRET measured as in FIG. 27A in the presence of α$_2$-adrenergic selective ligands (UK14,304 [UK], Dexmedetomidine [Dex], Clonidine [Clo], Yohimbine [Yo] and RX821002 [RX], 10 μM). Results are expressed as the difference in BRET signal observed in the presence and absence of ligand. *, P<0.05; ***, P<0.001 compared with UK-promoted BRET, respectively as FIG. 27C-1 and FIG. 27C-2.
Figures 2, 27C:
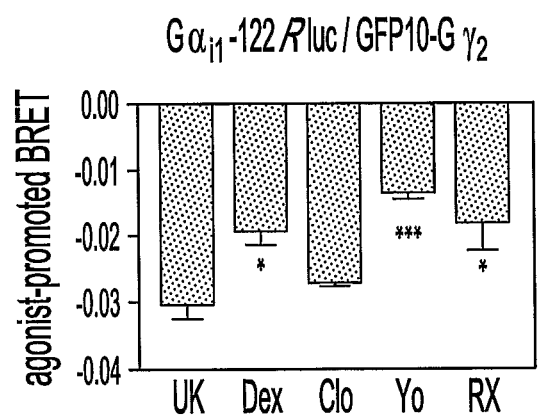

The effect of the panel of $\alpha_2$AR ligands on the Gα/Gβγ interaction was then examined. As shown in FIG. 27c, whether the Rluc was inserted in position 91 or 122 of $G\alpha_{i1}$, the full and partial agonists UK14,304, clonidine and dexmedetomidine decreased the BRET between $G\alpha_{i1}$-Rluc and GFP10-Gγ$_2$. However, as was the case for the $\alpha_{2A}$AR/$G\alpha_{i1}$ interaction, the antagonist yohimbine and RX821002 had no effect on the BRET signal between $G\alpha_{i1}$-91Rluc and GFP10-Gγ$_2$ (FIG. 27c) but promoted a significant decrease in the BRET signal between $G\alpha_{i1}$-122Rluc and GFP10-Gγ$_2$ (FIG. 26c). Since an antagonist should not lead to G protein subunit dissociation, the decrease in BRET cannot reflect a dissociation of the two subunits but most-likely results from a conformational rearrangement within the G protein heterotrimer.

Example 5

Insight into Structural Rearrangements of Gαβγ Complex

Figures 1, 28A:
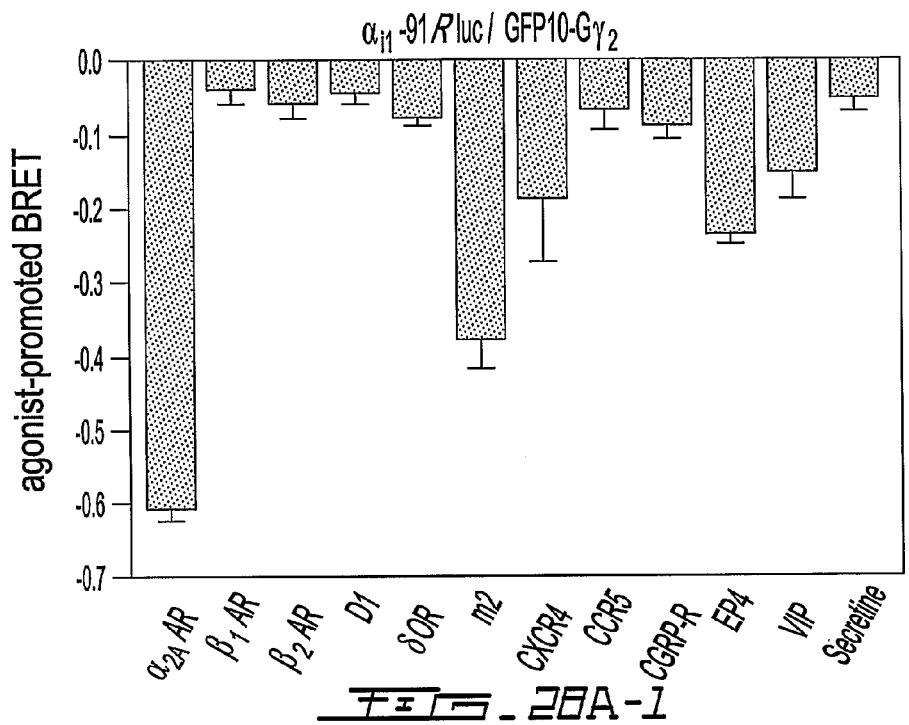
Figures 2, 28A:
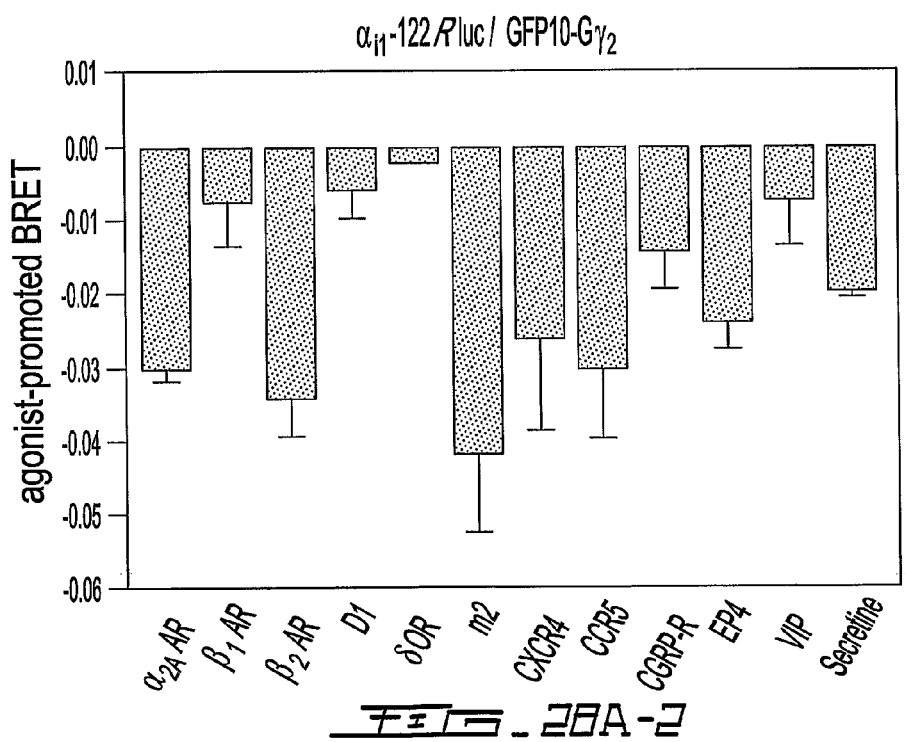

To further explore the structural rearrangements within the $G\alpha_{i1}β_1γ_2$ complex upon receptor activation, BRET between $G\alpha_{i1}$-91Rluc or $G\alpha_{i1}$-122Rluc and GFP10-Gγ$_2$ was monitored in response to the activation of a panel of receptors ($\alpha_{2A}$-, β$_1$- and β$_2$-adrenergic, dopamine-D1, δ-opioid, muscarinic-M2, chemokine-CXCR4 and -CCR5, calcitonin gene related peptide [CRLR+RAMP1], prostaglandine-EP4, vasoactive intestinal peptide and secretine). As shown in FIG. 28a, activation of each receptor with their cognate agonists led to BRET reductions for both $G\alpha_{i1}$-91Rluc and $G\alpha_{i1}$-122Rluc. Although the orientation of the change was the same, whatever the position of Rluc in the $G\alpha_{i1}$ subunit, the decrease in BRET was more dramatic for the Gαi-91 position, indicating that the relative movements of the AB- and BC-loops away from the amino-terminal of the Gγ$_2$ are of different amplitude.

In an effort to better understand the nature of the conformational rearrangements between Gγ$_2$ and $G\alpha_{i1}$ following activation, a third construct ($G\alpha_{i1}$-60Rluc) was engineered where RLuc was introduced in the linker 1 region connecting the helical and GTPase domains of $G\alpha_{i1}$ (FIG. 15b). In contrast to what was observed for the 91 and 122 position, all receptors tested promoted an increase in BRET between $G\alpha_{i1}$-60Rluc and GFP10-Gγ$_2$ (FIG. 28b). This opposite change indicates that while the AB- and BC-loops move away, the linker-1 region gets closer from the amino-terminal of G$\gamma_2$ during the activation process, further supporting that the BRET changes observed do not reflect a complete dissociation of the G$\alpha_{i1}\beta_1\gamma_2$ complex but rather a reorganization within the complex. The fact that all receptors tested promoted the same pattern of BRET changes between GFP10-G$\gamma_2$ and the three G$\alpha_{i1}$-Rluc biosensors suggests that they reflect a common Gi activation process.

DISCUSSION

Activation of Pre-Associated $\alpha_{2A}$AR/G$\alpha_{i1}\beta_1\gamma_2$ Complex The detection of a specific basal BRET signal between the $\alpha_{2A}$AR and either G$\alpha_{i1}$, G$\beta_1$ or G$\gamma_2$ clearly indicates that at least a fraction of the receptor exists in pre-associated complexes with G$\alpha\beta\gamma$ in the absence of receptor activation. This is consistent with a significant body of evidence indicating that receptor promoted activation of G proteins does not result only from random collision between proteins but involves more highly organized modules that include pre-coupled receptor/G protein complexes[27, 28]. Therefore, a question raised by the present data is whether the detected changes in receptor/G protein interactions result from the recruitment of G proteins to the activated receptor or from rearrangements within pre-existing receptor/G protein complexes.

Two lines of evidence support the second hypothesis. First, BRET$_{50}$ values obtained from BRET titration curves did not reveal any change in the apparent affinity of the $\alpha_{2A}$AR or $\beta_2$AR receptor for the G protein subunits following agonist stimulation. Second, depending on the position of the energy donor (Rluc) within G$\alpha_{i1}$, agonist stimulation of $\alpha_{2A}$AR-GFP2 led to either an increase (for G$\alpha_{i1}$-91Rluc) or a decrease (for G$\alpha_{i1}$-122Rluc) in the BRET between receptor and G$\alpha$ following similar kinetics. An active recruitment of the G protein to the receptor would be predicted to increase the relative affinity of the receptor for the G protein subunits that should be detected by an increase in BRET, independently of the position of the energy donor within G$\alpha_{i1}$. Thus, the data does not support the occurrence of a dynamic recruitment of the G protein to the receptor during the early event of G protein activation.

The agonist promoted conformational rearrangements within a pre-assembled receptor/G protein complex suggested by the data is also supported by similar results obtained with the Protease Activated Receptor and both G$\alpha_{12}$ and G$\alpha_{i1}$ presented by Ayoub et al (provide citation). These conclusions are consistent with recent computational modeling of the rhodopsin/transducin (Gt) complex. Indeed, analysis of the electrostatic and shape complementarity between the crystal structure of inactive rhodopsin and Gt suggested that light leads to conformational changes within a rhodopsin/Gt supramolecular complex formed prior to the activation of the photoreceptor[29].

Consistent with the latter conclusion is the observation that both the agonist-promoted increase (for G$\alpha_{i1}$-91Rluc) and decrease (for G$\alpha_{i1}$-122Rluc) in BRET between the receptor and G$\alpha_{i1}$ were stable for extended period of time with no indication of a change in the association status. It could, however, be argued that the stable BRET signals observed following agonist stimulation reflects a new steady-state in the association/dissociation equilibrium and that the different BRET levels reached for G$\alpha_{i1}$-91Rluc and G$\alpha_{i1}$-122Rluc result from the different position of the energy donor within the associated complex. If it were the case, one would predict that preventing the re-association branch of the cycle would affect the steady-state BRET signals observed following receptor activation and allow the detection of dissociation. Contrary to this prediction, a stable agonist-promoted increase in BRET was also detected between $\beta_2$AR-GFP10 and a mutant form of G$\alpha_{i1}$ (QL-G$\alpha_{i1}$-122Rluc) that is unable to hydrolyse GTP and thus should not re-associate following receptor activation (FIG. 29). These results therefore demonstrate that the agonist-promoted changes in BRET reflect conformational changes within metastable receptor/G protein complexes, with no evidence for dissociation. Further supporting the notion that the decrease in BRET signals do not reflect a simple dissociation between the receptor and the G protein subunits is the observation that antagonist that should not promote dissociation also lead to a reduction of the BRET between $\alpha_{2A}$AR-GFP2 and G$\alpha_{i1}$-122Rluc.

The conformational nature of the ligand-modulated BRET signals also applies when considering the interactions between the G protein subunits. Indeed, as was the case for the receptor/G protein interactions, both agonists and antagonists promoted decreases in BRET between G$\alpha_{i1}$-91Rluc or G$\alpha_{i1}$-122Rluc and GFP10-G$\gamma_2$. Moreover, receptor-promoted activation of the G protein could be detected either as a decrease (for G$\alpha_{i1}$-91Rluc or G$\alpha_{i1}$-122Rluc) or an increase (for G$\alpha_{i1}$-60Rluc) in BRET between G$\alpha_{i1}$-Rluc and GFP10-G$\gamma_2$, thus confirming that distinct position of the energy donor can probe the conformational change differentially. The lack of receptor-promoted G protein subunit dissociation that is suggested by the position-dependent changes in agonist-modulated BRET signals is consistent with a previous report by Bünneman et al[6]. In their study, opposite agonist-promoted FRET signals between G$\alpha_{i1}$-91YFP and either G$\gamma_2$-CFP (agonist-promoted decrease) or CFP-G$\gamma_2$ (agonist-promoted increase) led them to conclude to the absence of G protein subunit dissociation. In a more recent study, however, the observation that receptor activation promoted a decrease in FRET between G$\alpha_o$-91YFP and CFP-G$\gamma_2$ led them to conclude that the lack of dissociation may be unique to G$\alpha_{i1}$[7]. Although, the authors considered the possible contribution of distinct conformational rearrangements, they did not formally test this hypothesis by using different fluorophore positions in either G$\alpha_o$ or G$\gamma$ but yet concluded to a dissociation of the two subunits. This is particularly surprising when considering that the AB-loop primary sequence diverges considerably between G$\alpha_{i1}$ and G$\alpha_o$ (less then 40% identity). Contrasting with this proposed G protein-specific activation process (G$\alpha_{i1}$ not dissociating from G$\beta\gamma$ whereas G$\alpha_o$ does), BRET between Rluc-G$\gamma$ and G$\alpha$-71 GFP10 increased following stimulation of a panel of receptors ($\beta$- and $\beta$-adrenergic, dopamine-D1, vasopressin-V2, prostaglandine-EP4, vasointestinal peptide and secretine) (FIG. 30), suggesting that the lack of G protein subunit dissociation in the early step of activation is not unique to G$\alpha_{i1}$.

This data challenges the classical collision-based model whereby functional interactions between the various partners were believed to reflect true ligand-regulated association/dissociation cycles. However, this model was deduced largely from in vitro assays using purified proteins[4] in which the cellular factors influencing the dynamics of protein interactions could be easily recreated. More recently, agonist-promoted decreases in FRET between G$\alpha$ and G$\beta$ or G$\gamma$ in *Dictyostelium discoideum* and *Saccharomyces cerevisiae*, respectively, were interpreted as evidence of receptor-promoted dissociation of the G protein complex in living cells[30, 31]. Although a loss of FRET is consistent with dissociation, it can also reflect conformational rearrangements that promote an increase in the distance between the fluorophores inserted in the G$\alpha$ and G$\beta$ or G$\gamma$ subunits. Based on primary sequence comparison, the position used to insert the GFP variants into the *Dictyostelium discoideum* Gα subunit corresponds to the position 91 used to insert Rluc into the mammalian $G\alpha_{i1}$ in the present study. Consistent with the decrease in FRET previously observed, receptor activation led to a decrease in BRET between $G\alpha_{i1}$-91Rluc and GFP10-Gγ$_2$. Only the monitoring of a distinct position within $G\alpha_{i1}$ ($G\alpha_{i1}$-60Rluc) permitted the observation of the increase which suggested that a conformational change rather than a dissociation was being detected. Consistent with the notion that subunit dissociation may not be occurring in the early step of G protein activation, is the observation by Klein et al[5] that expression of a construct covalently attaching Gα to Gβ rescued α-mating factor responsiveness in a Gβ deficient yeast strain, demonstrating that physical dissociation of the subunits is not a pre-requisite for G protein activity.

The data presented above does not permit the exclusion of the occurrence of receptor-promoted dissociation of the complex but clearly demonstrates that structural rearrangements within a stable $\alpha_{2A}AR/G\alpha_{i1}\beta_1\gamma_2$ complex can be monitored in the early steps of the activation process.

Structural Rearrangements of the Receptor/G Protein Complex Following Receptor Activation The efficacy of resonance energy transfer depends on both the distance and the orientation between energy donors and acceptors inserted in specific positions within macromolecular complexes. Thus, in combination with ether types of structural information such as crystal coordinates and molecular modelling, variations in FRET or BRET efficacy have been used to monitor both intra- and inter-molecular conformational rearrangements and to propose or refine dynamic rearrangements within structural models[18, 20-22]. Applying this reasoning to the changes in BRET signals observed between the different positions within the receptor/G protein complexes allows inferences to be made concerning the conformational changes occurring during the initial steps of activation. When considering the relative movement of the receptor and G protein in relation to one another, the data suggests that the receptors' carboxyl tails, the AB-loop of the $G\alpha_{i1}$ helical domain and the N-terminal of Gγ$_2$ get closer following receptor activation. Indeed, for the three receptors tested ($\alpha_{2A}AR$, $\beta_2AR$ and CGRP receptor), agonist stimulation promoted an increases in the BRET signal between the receptor's carboxyl tails and both $G\alpha_{i1}$-91Rluc and GFP10-Gγ$_2$. Based on the crystal structure of the inactive $G\alpha_{i1}\beta_1\gamma_2$ heterotrimer[32], the N-terminal of Gγ$_2$ is in close apposition to the AB-loop of the $G\alpha_{i1}$ helical domain (FIG. 31a). It follows that receptor activation most-likely leads to a rearrangement that brings the bottom part of the heterotrimer closer to the receptors' carboxyl tail. In contrast with this conformational rearrangement that was perceived independently of the length of the receptor's carboxyl tail, the relative movement of the BC-loop of the Gα helical domain was sensed differentially depending on the receptor considered: a decrease in BRET was detected between $G\alpha_{i1}$-122Rluc and the $\alpha_{2A}AR$ and $\alpha_{2B}AR$ short C-tail whereas an increase was observed with the $\beta_2$ AR and CGRP longer C-tails.

Given the lack of structural information about the active receptor conformation and the receptor/G protein interface, it is difficult to propose a detailed conformational reorganization clearly describing the relative movement of the G protein vs the receptor's carboxyl-tail during activation. However, the observation that PTX pre-treatment greatly blunted agonist-promoted BRET changes between the receptor and all the tested positions within the G protein heterotrimer clearly demonstrates that the BRET changes reflects, at least in part, the relative movement of the G protein subunits during activation. The comparison of the BRET changes detected by the different positions within the G protein heterotrimer also allows inferences to be made about the conformational changes stabilized by various ligands. For instance, whereas the partial agonist dexmedetomidine promoted a partial increase in BRET between $\alpha_{2A}AR$ and either Gβ$_1$, Gγ$_2$ or the position 91 of $G\alpha_{i1}$ (when compared with the increase promoted by the full agonist UK14,304), the decrease in BRET detected between the receptor and the position 122 of $G\alpha_{i1}$ were of similar amplitude for dexmedetomidine and UK14, 340. This clearly indicates that the partial agonist promotes conformational changes that are distinct from those stabilized by the full agonist. These results therefore do not support the notion that partial agonism results from the stabilization of only a fraction of the receptor into an active conformation identical to that promoted by the full agonist. Therefore, the use of multiple BRET sensor sites within the receptor-G protein complex permits the detection of ligand-specific conformational changes that most likely reflect distinct "textures" in ligand efficacy[33, 34].

Structural Rearrangements of the Heterotrimeric G Protein Complex Following Receptor Activation When considering the movement of Gγ$_2$ relative to the three different insertion sites probed within $G\alpha_{i1}$ (60, 91 and 122), the profiles of agonist-promoted BRET changes were identical for the twelve receptors tested. In all cases, receptor activation led to an increase in BRET between Gγ$_2$ and $G\alpha_{i1}$-60 and a decrease between Gγ$_2$ and either $G\alpha_{i1}$-91 or $G\alpha_{i1}$-122. Such conservation of the BRET change profiles among a large selection of GPCRs strongly indicates that the changes observed reflects a common structural rearrangements characteristic of G protein activation.

Figure 31B:
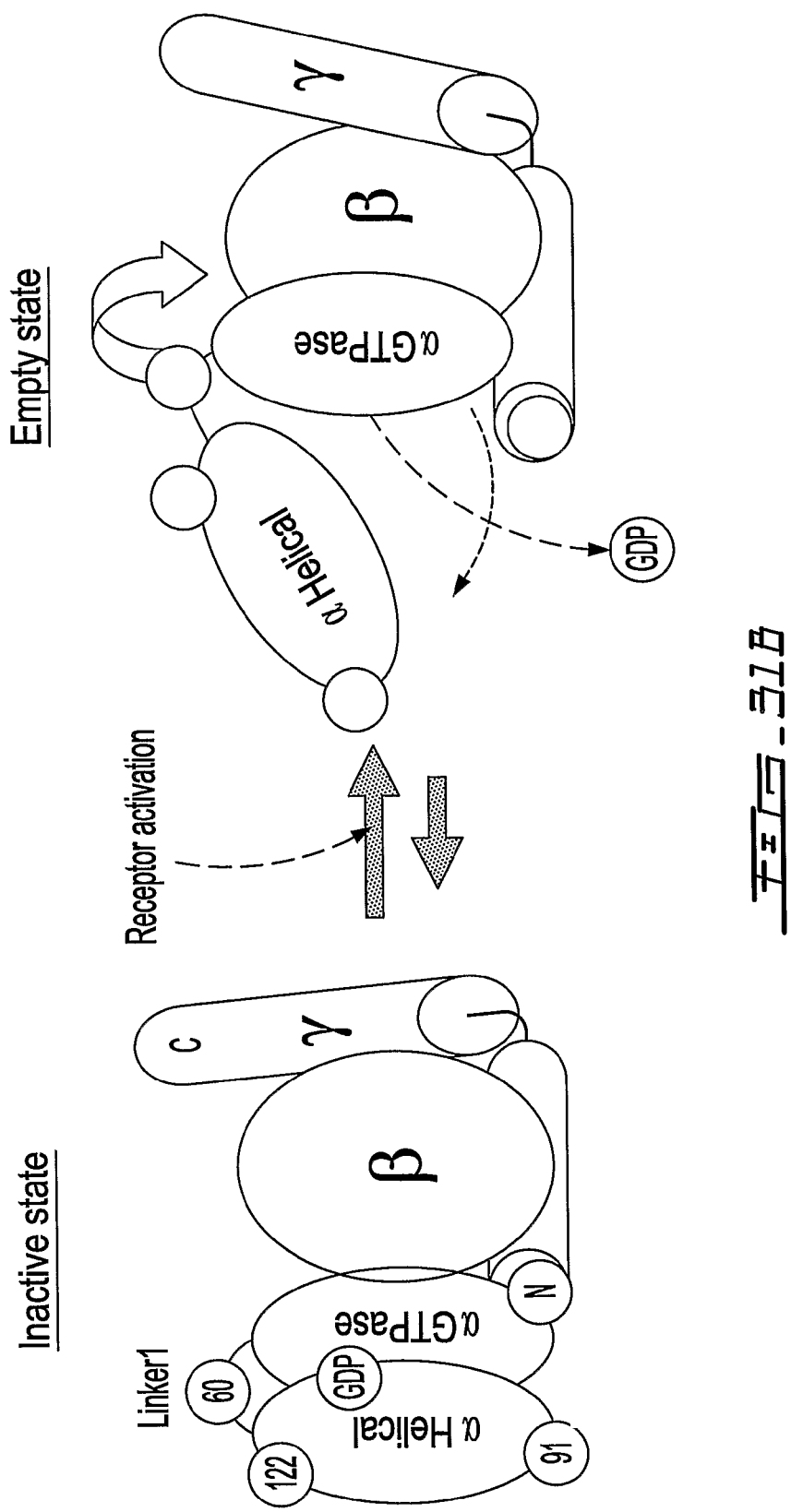
FIG. 31B: Schematic representation of structural rearrangement within Gα$_{i1}$β$_1$γ$_2$ detected by BRET following receptor activation. Rluc probes within Gα$_{i1}$ are shown in blue while GFP probe at the N-terminal of Gγ$_2$ is shown in green. The scheme represents an opening of Gα$_{i1}$-GTPase and Gα$_{i1}$H trough linker 1 (like a clamp), thus increasing RLuc91-Gγ$_2$N and RLuc122-Gγ$_2$N distances while shortening that of RLuc60-Gγ$_2$N. These rearrangements would thus create an exit route for the guanine nucleotide.
Figures 1, 32A:
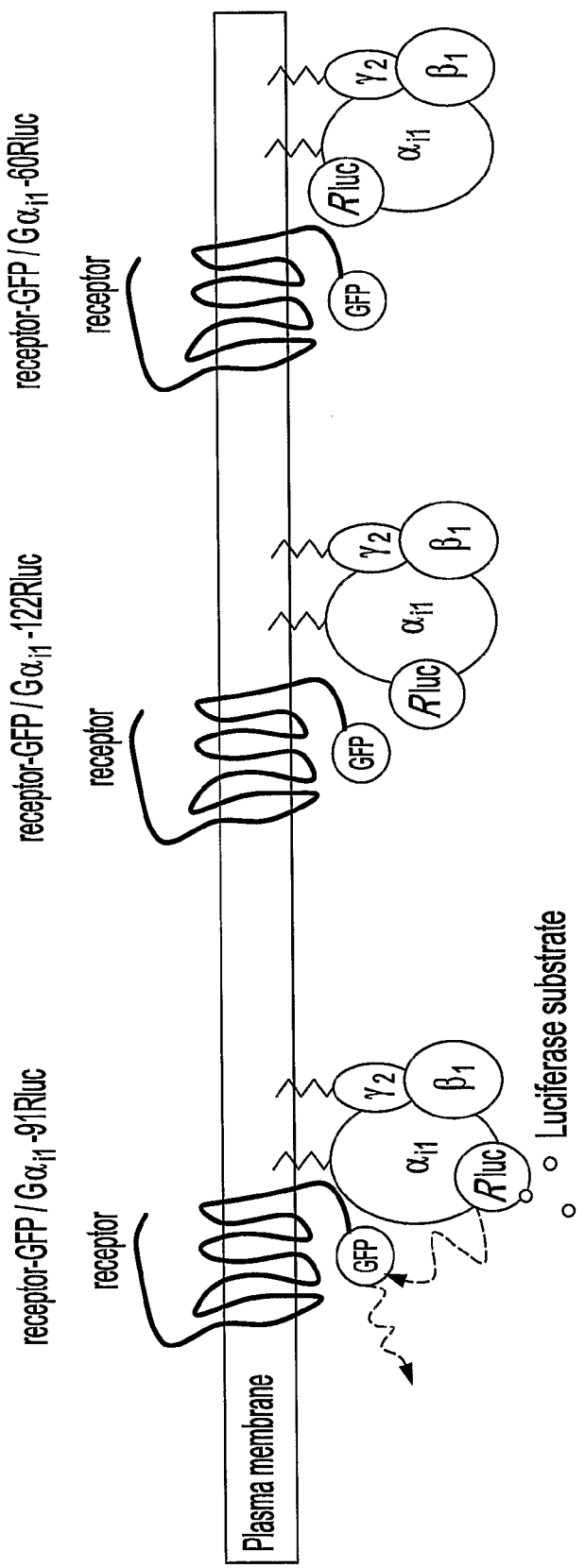
FIG. 32A: BRET assay between a GPCR and one of the heterotrimeric G proteins, either Gαi1 (at position 60, 91 or 122), Gβ1 or Gγ2, FIGS. 32A-1, 32A-2, and 32A-3, respectively.
Figures 2, 32A:
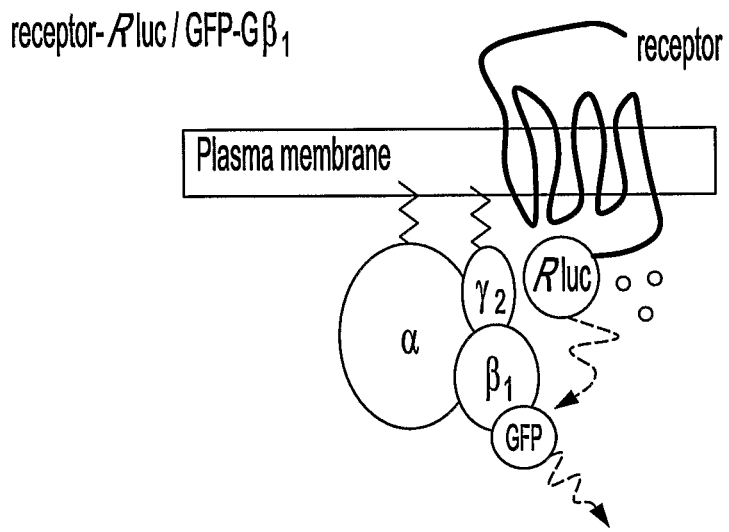
Figures 3, 32A:
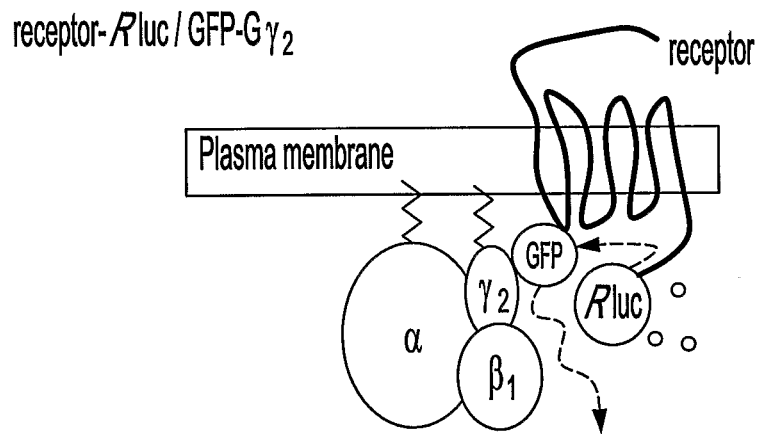
Figures 1, 32B:
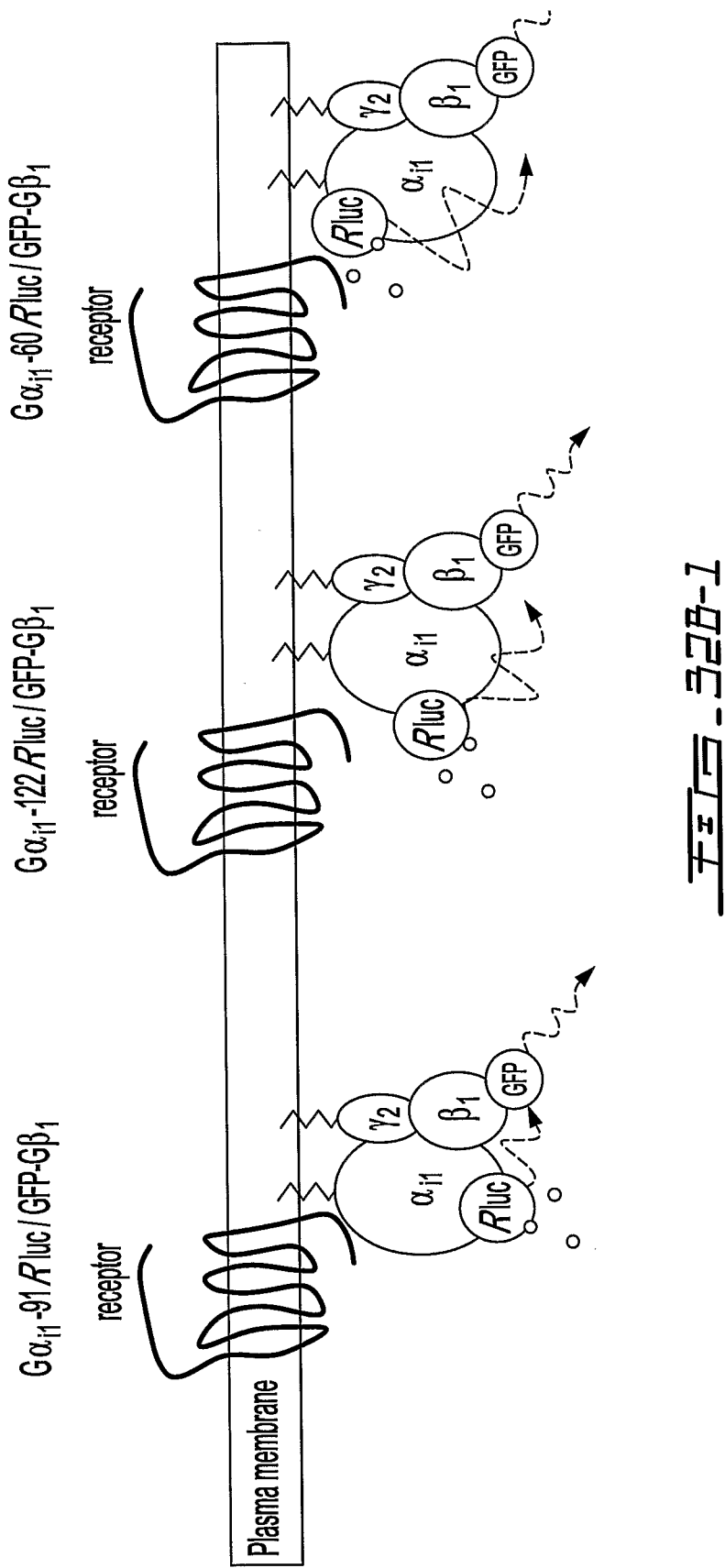
FIG. 32B: BRET assay between Gαi1 (at position 60, 91 or 122) and either Gβ1 or Gγ2.

Based on the crystal structure of $G\alpha_{i1}\beta_1\gamma_2$, the positions of the energy donors and acceptors allows the monitoring of the relative movements between the Gγ$_2$N and either, AB- (position 91) or BC- (position 122) loops within the helical domain or the linker 1 (position 60) connecting the helical domain to the GTPase domain of $G\alpha_{i1}$. Taken as a whole, the agonist-promoted BRET changes between the different sites suggest that the helical domain rotates away while the linker 1 region gets closer to Gγ$_2$N (FIG. 31b). This is consistent with the flexible linker 1 region acting as a hinge during the opening of the helical domain. Such a conformational changes that stabilizes GαH in an open conformation is required to create a in exit route for the nucleotide from the GTPase domain following activation. This finding is not inconsistent with the "lever arm" model of G protein activation[14, 15], since the movement of the GαN could lead to the opening of Gβγ away from Gα. However, the data indicates that the opening of the GαH during activation is not accompanied by a complete dissociation of Gα from Gβγ, since the Gα linker 1 region appears more closely associated to the Gγ following receptor stimulation. In that sense, the data is entirely compatible with the more recent "gear shift" model proposed by Cherfils et al. which is based on the homology with the activation process of small G proteins by their guanine nucleotide exchange factors[12]. In that model, the β-propeller region of Gβ is proposed to tighten its interaction with the Gα GTPase domain in the nucleotide empty state promoted by receptor activation. Such closer packing between the Gα GTPase domain and the Gβγ dimer is entirely consistent with the increased BRET observed between GγN and the linker 1 region of $G\alpha_{i1}$ (FIG. 28b). Also according to the model, GγN engages a gear that displaces GαH as a rigid body away from the GTPase domain, a movement that should also result in a greater separation between GαH and Gγ. This prediction is in agreement with the decrease in BRET observed between Gγ$_2$ and both the AB- and BC-loops of $G\alpha_{i1}$H (FIG. 28a). The data is also entirely consistent with a model based on molecular dynamic simulation of transducin, suggesting that nucleotide exchange mechanism of Gt is similar to that of small G proteins[13].

Taken together the results are consistent with a model whereby receptor activation promotes a "gear-shift"-like reorganization of a preassembled receptor/G protein complex that leads to the opening but not the dissociation of the Gα/βγ interface. Such opening allows GαH to move away form the Gα-GTPase domain, thus facilitating nucleotide exit. It follows that the BRET changes detected between G$\gamma_2$ and the various positions in G$\alpha_{i1}$ may correspond to the transition toward the nucleotide empty state. It may not be surprising that the dynamic changes monitored by BRET reflect the formation of this transient state since the crystal structure of the GTP- and GDP-bound state revealed only local changes in the nucleotide binding pocket that should not lead to BRET changes when considering the position of the energy donor and acceptor used in the present study. Although consistent with the "gear-shift" model the data may also be compatible with other structural reorganizations of the heterotrimer involving a relative rotation or clamp-like opening of the entire Gα subunit away from Gβγ such that the linker 1 region gets closer while the helical domain gets further from the N-terminus of Gγ.

Although the present invention has been described by way of specific embodiments and examples thereof, it will be apparent to persons of skill in the art that modifications may be made to it without departing from its spirit, scope and nature. For example, while the embodiments have been exemplified with G protein coupled receptors, the invention should also be extended to the tyrosine kinase and cytokine receptor families given the recent findings that these receptors can transduce cell signaling through heterotrimeric G proteins as well.

LIST OF REFERENCES

1. Gilman, A. G., "G proteins: transducers of receptor-generated signals", *Annu. Rev. Biochem.*, 56, 615-649 (1987).
2. Bourne, H. R., "How receptors talk to trimeric G proteins", *Curr. Opin. Cell Biol.*, 9, 134-142 (1997).
3. Cabrera-Vera, T. M. et al., "Insights into G protein structure, function, and regulation", *Endocr. Rev.*, 24, 765-781 (2003).
4. Rebois, R. V., Warner, D. R., & Basi, N. S., "Does subunit dissociation necessarily accompany the activation of all heterotrimeric G proteins?", *Cell Signal.*, 9, 141-151 (1997).
5. Klein, S., Reuveni, H., & Levitzki, A., "Signal transduction by a nondissociable heterotrimeric yeast G protein", *Proc. Natl. Acad. Sci. U.S.A*, 97, 3219-3223 (2000).
6. Bunemann, M., Frank, M., & Lohse, M. J., "Gi protein activation in intact cells involves subunit rearrangement rather than dissociation", *Proc. Natl. Acad. Sci. U.S.A*, 100, 16077-16082 (2003).
7. Frank, M., Thumer, L., Lohse, M. J., & Bunemann, M., "G Protein activation without subunit dissociation depends on a G{alpha}(i)-specific region", *J. Biol. Chem.*, 280, 24584-24590 (2005).
8. Gales, C. et al., "Real-time monitoring of receptor and G-protein interactions in living cells", *Nat. Methods*, 2, 177-184 (2005).
9. Sprang, S. R., "G protein mechanisms: insights from structural analysis", *Annu. Rev. Biochem.*, 66, 639-678 (1997).
10. Noel, J. P., Hamm, H. E., & Sigler, P. B., "The 2.2 A crystal structure of transducin-alpha complexed with GTP gamma S", *Nature*, 366, 654-663 (1993).
11. Sondek, J., Lambright, D. G., Noel, J. P., Hamm, H. E., & Sigler, P. B., "GTPase mechanism of Gproteins from the 1.7-A crystal structure of transducin alpha-GDP-AIF-4", *Nature*, 372, 276-279 (1994).
12. Cherfils, J. & Chabre, M., "Activation of G-protein Galpha subunits by receptors through Galpha-Gbeta and Galpha-Ggamma interactions", *Trends Biochem. Sci.*, 28, 13-17 (2003).
13. Ceruso, M. A., Periole, X., & Weinstein, H., "Molecular dynamics simulations of transducin: interdomain and front to back communication in activation and nucleotide exchange", *J. Mol. Biol.*, 338, 469-481 (2004).
14. Rondard, P. et al., "Mutant G protein alpha subunit activated by Gbeta gamma: a model for receptor activation?", *Proc. Natl. Acad. Sci. U.S.A*, 98, 6150-6155 (2001).
15. Iiri, T., Farfel, Z., & Bourne, H. R., G-protein diseases furnish a model for the turn-on switch, *Nature*, 394, 35-38 (1998).
16. Pfleger, K. D. & Eidne, K. A., "Monitoring the formation of dynamic G-protein-coupled receptor-protein complexes in living cells", *Biochem. J.*, 385, 625-637 (2005).
17. Miyawaki, A., "Visualization of the spatial and temporal dynamics of intracellular signaling", *Dev. Cell*, 4, 295-305 (2003).
18. Tateyama, M., Abe, H., Nakata, H., Saito, O., & Kubo, Y., "Ligand-induced rearrangement of the dimeric metabotropic glutamate receptor 1 alpha", *Nat. Struct. Mol. Biol.*, 11, 637-642 (2004).
19. Vilardaga, J. P., Bunemann, M., Krasel, C., Castro, M., & Lohse, M. J., "Measurement of the millisecond activation switch of G protein-coupled receptors in living cells", *Nat. Biotechnol.*, 21, 807-812 (2003).
20. Charest, P. G., Terrillon, S., & Bouvier, M., "Monitoring agonist-promoted conformational changes of beta-arrestin in living cells by intramolecular", *BRET. EMBO Rep.*, 6, 334-340 (2005).
21. Schaufele, F. et al., "The structural basis of androgen receptor activation: intramolecular and intermolecular amino-carboxy interactions", *Proc. Natl. Acad. Sci. U.S.A*, 102, 9802-9807 (2005).
22. Tsuboi, T., Lippiat, J. D., Ashcroft, F. M., & Rutter, G. A., "ATP-dependent interaction of the cytosolic domains of the inwardly rectifying K+ channel Kir6.2 revealed by fluorescence resonance energy transfer", *Proc. Natl. Acad. Sci. U.S.A*, 101, 76-81 (2004).
23. Mercier, J. F., Salahpour, A., Angers, S., Breit, A., & Bouvier, M., "Quantitative assessment of beta 1- and beta 2-adrenergic receptor homo- and heterodimerization by bioluminescence resonance energy transfer", *J. Biol. Chem.*, 277, 44925-44931 (2002).
24. Ramsay, D. et al., "High-affinity interactions between human alpha1A-adrenoceptor C-terminal splice variants produce homo- and heterodimers but do not generate the alpha1L-adrenoceptor", *Mol. Pharmacol.*, 66, 228-239 (2004).
25. Oakley, R. H., Laporte, S. A., Holt, J. A., Barak, L. S., & Caron, M. G., "Molecular determinants underlying the formation of stable intracellular G protein-coupled receptor-beta-arrestin complexes after receptor endocytosis*", *J. Biol. Chem.*, 276, 19452-19460 (2001).

26. Perroy, J., Pontier, S., Charest, P. G., Aubry, M., & Bouvier, M., "Real-time monitoring of ubiquitination in living cells by BRET", *Nat. Methods*, 1, 203-208 (2004).
27. Rebois, R. V. & Hebert, T. E., "Protein complexes involved in heptahelical receptor-mediated signal transduction", *Receptor Channels*, 9, 169-194 (2003).
28. Neubig, R. R., "Membrane organization in G-protein mechanisms", *FASEB J.*, 8, 939-946 (1994).
29. Fanelli, F. & Dell'orco, D., "Rhodopsin activation follows precoupling with transducin: inferences from computational analysis", *Biochemistry*, 44, 14695-14700 (2005).
30. Janetopoulos, C., Jin, T., & Devreotes, P., "Receptor-mediated activation of heterotrimeric G-proteins in living cells", *Science*, 291, 2408-2411 (2001).
31. Yi, T. M., Kitano, H., & Simon, M. I., "A quantitative characterization of the yeast heterotrimeric G protein cycle", *Proc. Natl. Acad. Sci. U.S.A*, 100, 10764-10769 (2003).
32. Wall, M. A. et al., "The structure of the G protein heterotrimer Gi alpha 1 beta 1 gamma 2", *Cell*, 83, 1047-1058 (1995).
33. Kenakin, T., "Ligand-selective receptor conformations revisited: the promise and the problem", *Trends Pharmacol. Sci.*, 24, 346-354 (2003).
34. Kenakin, T., "New concepts in drug discovery: collateral efficacy and permissive antagonism", *Nat. Rev. Drug Discov.*, 4, 919-927 (2005).
35. Nagai, T. et al., "A variant of yellow fluorescent protein with fast and efficient maturation for cell-biological applications", *Nat. Biotechnol.*, 20, 87-90 (2002).
36. Milligan, G., "Applications of bioluminescence- and fluorescence resonance energy transfer to drug discovery at G protein-coupled receptors", *Eur. J. Pharm. Sci.*, 21, 397-405 (2004).
37. Gales, C. et al., "Mutation of Asn-391 within the conserved NPXXY motif of the cholecystokinin B receptor abolishes Gq protein activation without affecting its association with the receptor", *J. Biol. Chem.*, 275, 17321-17327 (2000).
38. Krieger, E., Koraimann, G., & Vriend, G., "Increasing the precision of comparative models with YASARA NOVA—a self-parameterizing force field", *Proteins*, 47, 393-402 (2002).
39. Weng, G., Jordan J. D., & Chen Y., "Structural basis for the function of the heterotrimeric G-proteins", *Seminars in NEUROSCIENCE*, 9, 175-188. (1998).
40. Bockaert, J., Claeysen, S., Becamel, C., Pinloche, S. & Dumuis, A., "G protein-coupled receptors: dominant players in cell-cell communication", *Int Rev. Cytol.*, 212, 63-132 (2002).
41. Bouvier, M., "Oligomerization of G-protein-coupled transmitter receptors", *Nat. Rev. Neurosci.*, 2, 274-286 (2001).
42. Angers, S. et al., "Detection of beta 2-adrenergic receptor dimerization in living cells using bioluminescence resonance energy transfer (BRET)", *Proc. Natl. Acad. Sci. U.S.A*, 97, 3684-3689 (2000).
43. Yu, J. Z. & Rasenick, M. M., "Real-time visualization of a fluorescent G(alpha)(s): dissociation of the activated G protein from plasma membrane", *Mol. Pharmacol.*, 61, 352-359 (2002).
44. Ruiz-Velasco, V. & Ikeda, S. R., "Functional expression and FRET analysis of green fluorescent proteins fused to G-protein subunits in rat sympathetic neurons", *J. Physio*, 537, 679-692 (2001).
45. Evanko, D. S., Thiyagarajan, M. M., Siderovski, D. P. & Wedegaertner, P. B., "Gbeta gamma isoforms selectively rescue plasma membrane localization and palmitoylation of mutant Galphas and Galphaq", *J. Biol. Chem.*, 276, 23945-23953 (2001).
46. Wenzel-Seifert, K. & Seifert, R., "Molecular analysis of beta(2)-adrenoceptor coupling to G(s)-, G(i)-, and G(q)-proteins", *Mol. Pharmacol.*, 58, 954-966 (2000).
47. Huang, J. S., Ramamurthy, S. K., Lin, X. & Le Breton, G. C., "Cell signalling through thromboxane A2 receptors", *Cell Signal.*, 16, 521-533 (2004).
48. Kinsella, B. T., "Thromboxane A2 signalling in humans: a 'Tail' of two receptors", *Biochem. Soc. Trans.*, 29, 641-654 (2001).
49. Crespo, P., Cachero, T. G., Xu, N. & Gutkind, J. S., "Dual effect of beta-adrenergic receptors on mitogenactivated protein kinase. Evidence for a beta gamma-dependent activation and a G alpha s-cAMP mediated inhibition". *J. Biol. Chem.*, 270, 25259-25265 (1995).
50. Chung, F. Z., Wang, C. D., Potter, P. C., Venter, J. C. & Fraser, C. M., "Site-directed mutagenesis and continuous expression of human beta-adrenergic receptors. Identification of a conserved aspartate residue involved in agonist binding and receptor activation", *J. Biol. Chem.*, 263, 4052-4055 (1988).
51. Chidiac, P., Nouet, S. & Bouvier, M., "Agonist-induced modulation of inverse agonist efficacy at the beta 2-adrenergic receptor", *Mol. Pharmacol.*, 50, 662-669 (1996).
52. Levitzki, A. & Klein, S., "G-protein subunit dissociation is not an integral part of G-protein action". *Chembiochem.*, 3, 815-818 (2002).
53. Jones, S. B., Leone, S. L. & Bylund, D. B., "Desensitization of the alpha-2 adrenergic receptor in HT29 and opossum kidney cell lines", *J. Pharmacol. Exp. Ther.*, 254, 294-300 (1990).
54. Benovic, J. L., Bouvier, M., Caron, M. G. & Lefkowitz, R. J., "Regulation of adenylyl cyclase-coupled betaadrenergic receptors", *Annu. Rev. Cell Biol.*, 4, 405-428 (1988).
55. Clark, W. A., Jian, X., Chen, L. & Northup, J. K., "Independent and synergistic interaction of retinal G-protein subunits with bovine rhodopsin measured by surface plasmon resonance", *Biochem. J.*, 358, 389-397 (2001).
56. Waller, A. et al., "Techniques: GPCR assembly, pharmacology and screening by flow cytometry", *Trends Pharmacol. Sci.*, 25, 663-669 (2004).
57. Albert, P. R. & Robillard, L., "G protein specificity: traffic direction required", *Cell Signal.*, 14, 407-418 (2002).
58. Bertrand, L. et al., "The BRET$^2$/arrestin assay in stable recombinant cells: a platform to screen for compounds that interact with G protein-coupled receptors (GPCRS)", *J. Recept. Signal. Transduct. Res.*, 22, 533-541 (2002).
59. Perroy, J., Adam, L., Qanbar, R., Chemer, S. & Bouvier, M., "Phosphorylation-independent desensitization of GABA(B) receptor by GRK4", *EMBO J.*, 22, 3816-3824 (2003).
60. Morello, J. P. et al., "Pharmacological chaperones rescue cell-surface expression and function of misfolded V2 vasopressin receptor mutants", *J. Clin. Invest*, 105, 887-895 (2000).
61. Azzi, M. et al., "Allosteric effects of G protein overexpression on the binding of beta-adrenergic ligands with distinct inverse efficacies", *Mol. Pharmacol.*, 60, 999-1007 (2001).

What is claimed is:

1. A bioluminescence resonance energy transfer (BRET) technology-based bimolecular biosensor, comprising:

1) a G protein coupled receptor (GPCR) fused to a bioluminescent molecule or a fluorescent molecule; and 2) a G protein subunit that is part of a G protein heterotrimeric complex fused to a bioluminescent molecule or a fluorescent molecule, said subunit being selected from the group consisting of Gα, Gβ and Gγ, wherein when the GPCR is fused to a bioluminescent molecule, the G protein subunit is fused to a fluorescent molecule, and when the GPCR is fused to a fluorescent molecule, the G protein subunit is fused to a bioluminescent molecule; and wherein energy transferred by the bioluminescent molecule and accepted by the fluorescent molecule can be monitored.

2. The BRET technology-based bimolecular biosensor as defined in claim 1, wherein said bioluminescent molecule is luciferase and said energy acceptor is Green Fluorescent Protein (GFP) or a GFP variant.

3. The BRET technology-based bimolecular biosensor as defined in claim 2, wherein said bioluminescent molecule is *Renilla* luciferase (Rluc) and said GFP variant is GFP10, GFP2, eYFP or eYFPvenus.

4. The BRET technology-based bimolecular biosensor as defined in claim 1, wherein said G protein subunit is Gα.

5. The BRET technology-based bimolecular biosensor as defined in claim 4, wherein said Gα subunit is tagged at position 91 with luciferase and is encoded by an expression vector having the nucleotide sequence of SEQ ID NO: 2.

6. The BRET technology-based bimolecular biosensor as defined in claim 4, wherein said Gα is $G\alpha_s$, $G\alpha_o$, $G\alpha_{i1}$, $G\alpha_{i2}$, $G\alpha_{i3}$, $G\alpha_q$, $G\alpha_{11}$ or $G\alpha_{13}$.

7. The BRET technology-based bimolecular biosensor as defined in claim 4, wherein said Gα subunit is tagged at position 60 with luciferase and is encoded by an expression vector having the nucleotide sequence of SEQ ID NO: 1.

8. The BRET technology-based bimolecular biosensor as defined in claim 4, wherein said Gα subunit is tagged at position 122 with luciferase and is encoded by an expression vector having the nucleotide sequence of SEQ ID NO: 3.

9. The BRET technology-based bimolecular biosensor as defined in claim 4, wherein said Gα subunit is tagged at position 122 with luciferase and is encoded by an expression vector having the nucleotide sequence of SEQ ID NO: 3.

10. The BRET technology-based bimolecular biosensor as defined in claim 4, wherein said Gα subunit is tagged at position 91 with luciferase and is encoded by an expression vector having a degenerate nucleotide sequence of the nucleotide sequence of SEQ ID NO:2, and said degenerate nucleotide sequence encoding the same Gα subunit as SEQ ID NO:2.

11. The BRET technology-based bimolecular biosensor as defined in claim 4, wherein said Gα subunit is tagged at position 60 with luciferase and is encoded by an expression vector having a degenerate nucleotide sequence of the nucleotide sequence of SEQ ID NO:1, and said degenerate nucleotide sequence encoding the same Gα subunit as SEQ ID NO:1.

12. The BRET technology-based bimolecular biosensor as defined in claim 4, wherein said Gα subunit is tagged at position 122 with luciferase and is encoded by an expression vector having a degenerate nucleotide sequence of the nucleotide sequence of SEQ ID NO:3, and said degenerate nucleotide sequence encoding the same Gα subunit as SEQ ID NO:3.

13. The BRET technology-based bimolecular biosensor as defined in claim 1, wherein said G protein subunit is Gβ.

14. The BRET technology-based bimolecular biosensor as defined in claim 13, wherein said Gβ is Gβ1.

15. The BRET technology-based bimolecular biosensor as defined in claim 1, wherein said G protein subunit is Gγ.

16. The BRET technology-based bimolecular biosensor as defined in claim 15, wherein said G protein subunit is Gγ2.

17. The BRET technology-based bimolecular biosensor as defined in claim 1, wherein:
1) said GPCR is a mammalian GPCR; and
2) said G protein subunit is a mammalian G protein subunit.

18. A bioluminescence resonance energy transfer (BRET) technology-based bimolecular biosensor, comprising:
1) a first subunit consisting of a Gα protein subunit fused to a bioluminescent molecule or a fluorescent molecule; and
2) a second subunit consisting of a Gβ or Gγ protein subunit fused to a bioluminescent molecule or a fluorescent molecule,
wherein when the first subunit is fused with a bioluminescent molecule, said second subunit is fused with a fluorescent molecule, and when the first subunit is fused with a fluorescent molecule, said second subunit is fused with a bioluminescent molecule, and wherein energy is transferred by the bioluminescent molecule and accepted by the fluorescent molecule when the first subunit is in the presence of the second subunit and said energy transfer can be monitored.

19. The BRET technology-based bimolecular biosensor as defined in claim 18, wherein said Gα subunit is tagged at position 60 with luciferase and is encoded by an expression vector having the nucleotide sequence of SEQ ID NO: 1.

20. The BRET technology-based bimolecular biosensor as defined in claim 18, wherein said Gα subunit is tagged at position 91 with luciferase and is encoded by an expression vector having the nucleotide sequence of SEQ ID NO: 2.

21. The BRET technology-based bimolecular biosensor as defined in claim 18, wherein said Gα protein subunit is a $G\alpha_s$, $G\alpha_o$, $G\alpha_{i1}$, $G\alpha_{i2}$, $G\alpha_{i3}$, $G\alpha_q$, $G\alpha_{11}$ or $G\alpha_{13}$ protein subunit.

22. The BRET technology-based bimolecular biosensor as defined in claim 18, wherein said Gβ protein subunit is a Gβ1 protein subunit.

23. The BRET technology-based bimolecular biosensor as defined in claim 18, wherein said Gγ protein subunit is a Gγ2 protein subunit.

24. The BRET technology-based bimolecular biosensor as defined in claim 18, wherein said Gα is tagged with luciferase and said Gβ or Gγ protein subunit is tagged with a fluorescent molecule.

25. The BRET technology-based bimolecular biosensor as defined in claim 18, wherein said Gα is tagged with a fluorescent molecule and said Gβ or Gγ protein subunit is tagged with a luciferase.

26. The BRET technology-based bimolecular biosensor as defined in claim 18, wherein said G protein subunits are mammalian G-protein subunits.

27. The BRET technology-based bimolecular biosensor as defined in claim 18, wherein said Gα subunit is tagged at position 60 with luciferase and is encoded by an expression vector having a degenerate nucleotide sequence of the nucleotide sequence of SEQ ID NO:1, and said degenerate nucleotide sequence encoding the same Gα subunit as SEQ ID NO:1.

28. The BRET technology-based bimolecular biosensor as defined in claim 18, wherein said Gα subunit is tagged at position 91 with luciferase and is encoded by an expression vector having a degenerate nucleotide sequence of the nucleotide sequence of SEQ ID NO:2, and said degenerate nucleotide sequence encoding the same Gα subunit as SEQ ID NO:2.

29. The BRET technology-based bimolecular biosensor as defined in claim 18, wherein said Gα subunit is tagged at position 122 with luciferase and is encoded by an expression vector having a degenerate nucleotide sequence of the nucleotide sequence of SEQ ID NO:3, and said degenerate nucleotide sequence encoding the same Gα subunit as SEQ ID NO:3.

\* \* \* \* \*

SEQUENCE LISTING

<160> NUMBER OF SEQ ID NOS: 4

<210> SEQ ID NO 1
<211> LENGTH: 7403
<212> TYPE: DNA
<213> ORGANISM: Artificial
<220> FEATURE:
<223> OTHER INFORMATION: G alpha i1-60Rluc

<400> SEQUENCE: 1

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccaccatggg | ctgcacgctg | agcgccgagg | acaaggcggc | 960 |
| ggtggagcgg | agtaagatga | tcgaccgcaa | cctccgtgag | gacggcgaga | aggcggcgcg | 1020 |
| cgaggtcaag | ctgctgctgc | tcggtgctgg | tgaatctggt | aaaagtacaa | ttgtgaagca | 1080 |
| gatgaaaatt | atccatgaag | ctggttctgg | tggtggtgga | tccatgacca | gcaaggtgta | 1140 |
| cgacccccgag | cagaggaaga | ggatgatcac | cggcccccag | tggtgggcca | ggtgcaagca | 1200 |
| gatgaacgtg | ctggacagct | tcatcaacta | ctacgacagc | gagaagcacg | ccgagaacgc | 1260 |
| cgtgatcttc | ctgcacggca | acgccgctag | cagctacctg | tggaggcacg | tggtgccccca | 1320 |
| catcgagccc | gtggccaggt | gcatcatccc | cgatctgatc | ggcatgggca | agagcggcaa | 1380 |
| gagcggcaac | ggcagctaca | ggctgctgga | ccactacaag | tacctgaccg | cctggttcga | 1440 |
| gctcctgaac | ctgcccaaga | agatcatctt | cgtgggccac | gactggggcg | cctgcctggc | 1500 |
| cttccactac | agctacgagc | accaggacaa | gatcaaggcc | atcgtgcacg | ccgagagcgt | 1560 |
| ggtggacgtg | atcgagagct | gggacgagtg | gccagacatc | gaggaggaca | tcgccctgat | 1620 |
| caagagcgag | gagggcgaga | gatggtgct | ggagaacaac | ttcttcgtgg | agaccatgct | 1680 |
| gcccagcaag | atcatgagaa | agctggagcc | cgaggagttc | gccgcctacc | tggagccctt | 1740 |
| caaggagaag | ggcgaggtga | gaagacccac | cctgagctgg | cccagagaga | tcccctggt | 1800 |
| gaagggcggc | aagcccgacg | tggtgcagat | cgtgagaaac | tacaacgcct | acctgagagc | 1860 |
| cagcgacgac | ctgcccaaga | tgttcatcga | gagcgaccccc | ggcttcttca | gcaacgccat | 1920 |
| cgtggagggc | gccaagaagt | tccccaacac | cgagttcgtg | aaggtgaagg | gctgcactt | 1980 |
| cagccaggag | gacgcccccg | acgagatggg | caagtacatc | aagagcttcg | tggagagagt | 2040 |

```
gctgaagaac gagcagtctg gtggtggtgg atcctattca aagaggagt gtaaacaata     2100 caaagcagtg gtctacagta acaccatcca gtcaattatt gctatcatta gggctatggg     2160
gaggttgaag atagactttg gtgactcagc ccgggcggat gatgcacgcc aactctttgt     2220
gctagctgga gctgctgaag aaggctttat gactgcagaa cttgctggag ttataaagag     2280
attgtggaaa gatagtggtg tacaagcctg tttcaacaga tcccgagagt accagcttaa     2340
tgattctgca gcatactatt tgaatgactt ggacagaata gctcaaccaa attacatccc     2400
gactcaacaa gatgttctca gaactagagt gaaaactaca ggaattgttg aaacccattt     2460
tactttcaaa gatcttcatt ttaaaatgtt tgatgtggga ggtcagagat ctgagcggaa     2520
gaagtggatt cattgcttcg aaggagtgac ggcgatcatc ttctgtgtag cactgagtga     2580
ctacgacctg gttctagctg aagatgaaga aatgaaccga atgcatgaaa gcatgaaatt     2640
gtttgacagc atatgtaaca acaagtggtt tacagataca tccattatac ttttttctaaa    2700 caagaaggat ctcttttgaag aaaaaatcaa aaagagccct ctcactatat gctatccaga    2760
atatgcagga tcaaacacat atgaagaggc agctgcatat attcaatgtc agtttgaaga     2820
cctcaataaa agaaaggaca caaaggaaat atacacccac ttcacatgtg ccacagatac     2880
taagaatgtg cagtttgttt ttgatgctgt aacagatgtc atcataaaaa ataatctaaa     2940
agattgtggt ctcttttaac tcgagtctag agggcccgtt taaacccgct gatcagcctc     3000
gactgtgcct tctagttgcc agccatctgt tgtttgcccc tcccccgtgc cttccttgac     3060
cctggaaggt gccactccca ctgtcctttc ctaataaaat gaggaaattg catcgcattg     3120
tctgagtagg tgtcattcta ttctgggggg tggggtgggg caggacagca agggggagga     3180
ttgggaagac aatagcaggc atgctgggga tgcggtgggc tctatggctt ctgaggcgga     3240
aagaaccagc tggggctcta gggggtatcc ccacgcgccc tgtagcggcg cattaagcgc     3300
ggcgggtgtg gtggttacgc gcagcgtgac cgctacactt gccagcgccc tagcgcccgc     3360
tcctttcgct ttcttccctt cctttctcgc cacgttcgcc ggcttccccc gtcaagctct     3420
aaatcggggg ctccctttag ggttccgatt tagtgcttta cggcacctcg accccaaaaa     3480
acttgattag ggtgatggtt cacgtagtgg gccatcgccc tgatagacgg ttttcgccc     3540 tttgacgttg gagtccacgt tctttaatag tggactcttg ttccaaactg gaacaacact     3600
caaccctatc tcggtctatt cttttgattt ataagggatt ttgccgattt cggcctattg     3660
gttaaaaaat gagctgattt aacaaaaatt taacgcgaat taattctgtg aatgtgtgt     3720 cagttagggt gtggaaagtc cccaggctcc ccagcaggca gaagtatgca aagcatgcat     3780
ctcaattagt cagcaaccag gtgtggaaag tccccaggct cccagcagg cagaagtatg     3840 caaagcatgc atctcaatta gtcagcaacc atagtcccgc ccctaactcc gcccatcccg     3900
cccctaactc cgcccagttc cgcccattct ccgccccatg ctgactaatt tttttttatt     3960
tatgcagagg ccgaggccgc ctctgcctct gagctattcc agaagtagtg aggaggcttt     4020
tttggaggcc taggcttttg caaaaagctc ccgggagctt gtatatccat tttcggatct     4080
gatcaagaga caggatgagg atcgtttcgc atgattgaac aagatggatt gcacgcaggt     4140
tctccggccg cttgggtgga gaggctattc ggctatgact gggcacaaca gacaatcggc     4200
tgctctgatg ccgccgtgtt ccggctgtca gcgcaggggc gcccggttct ttttgtcaag     4260
accgacctgt ccggtgccct gaatgaactg caggacgagg cagcgcggct atcgtggctg     4320
gccacgacgg gcgttccttg cgcagctgtg ctcgacgttg tcactgaagc gggaagggac     4380
tggctgctat tgggcgaagt gccggggcag gatctcctgt catctcacct tgctcctgcc     4440
```

-continued

```
gagaaagtat ccatcatggc tgatgcaatg cggcggctgc atacgcttga tccggctacc    4500
tgcccattcg accaccaagc gaaacatcgc atcgagcgag cacgtactcg gatggaagcc    4560
ggtcttgtcg atcaggatga tctggacgaa gagcatcagg ggctcgcgcc agccgaactg    4620
ttcgccaggc tcaaggcgcg catgcccgac ggcgaggatc tcgtcgtgac ccatggcgat    4680
gcctgcttgc cgaatatcat ggtggaaaat ggccgctttt ctggattcat cgactgtggc    4740
cggctgggtg tggcggaccg ctatcaggac atagcgttgg ctacccgtga tattgctgaa    4800
gagcttggcg gcgaatgggc tgaccgcttc ctcgtgcttt acggtatcgc cgctcccgat    4860
tcgcagcgca tcgccttcta tcgccttctt gacgagttct tctgagcggg actctggggt    4920
tcgaaatgac cgaccaagcg acgcccaacc tgccatcacg agatttcgat tccaccgccg    4980
ccttctatga aaggttgggc ttcggaatcg ttttccggga cgccggctgg atgatcctcc    5040
agcgcgggga tctcatgctg gagttcttcg cccaccccaa cttgtttatt gcagcttata    5100
atggttacaa ataaagcaat agcatcacaa atttcacaaa taaagcattt ttttcactgc    5160
attctagttg tggtttgtcc aaactcatca atgtatctta tcatgtctgt ataccgtcga    5220
cctctagcta gagcttggcg taatcatggt catagctgtt tcctgtgtga aattgttatc    5280
cgctcacaat tccacacaac atacgagccg gaagcataaa gtgtaaagcc tggggtgcct    5340
aatgagtgag ctaactcaca ttaattgcgt tgcgctcact gcccgctttc cagtcgggaa    5400
acctgtcgtg ccagctgcat taatgaatcg gccaacgcgc ggggagaggc ggtttgcgta    5460
ttgggcgctc ttccgcttcc tcgctcactg actcgctgcg ctcggtcgtt cggctgcggc    5520
gagcggtatc agctcactca aaggcggtaa tacggttatc cacagaatca ggggataacg    5580
caggaaagaa catgtgagca aaaggccagc aaaaggccag gaaccgtaaa aaggccgcgt    5640
tgctggcgtt tttccatagg ctccgccccc ctgacgagca tcacaaaaat cgacgctcaa    5700
gtcagaggtg gcgaaacccg acaggactat aaagatacca ggcgtttccc cctggaagct    5760
ccctcgtgcg ctctcctgtt ccgaccctgc cgcttaccgg atacctgtcc gcctttctcc    5820
cttcgggaag cgtggcgctt tctcatagct cacgctgtag gtatctcagt tcggtgtagg    5880
tcgttcgctc caagctgggc tgtgtgcacg aaccccccgt tcagcccgac cgctgcgcct    5940
tatccggtaa ctatcgtctt gagtccaacc cggtaagaca cgacttatcg ccactggcag    6000
cagccactgg taacaggatt agcagagcga ggtatgtagg cggtgctaca gagttcttga    6060
agtggtggcc taactacggc tacactagaa gaacagtatt tggtatctgc gctctgctga    6120
agccagttac cttcggaaaa agagttggta gctcttgatc cggcaaacaa accaccgctg    6180
gtagcggttt ttttgtttgc aagcagcaga ttacgcgcag aaaaaaagga tctcaagaag    6240
atcctttgat cttttctacg gggtctgacg ctcagtggaa cgaaaactca cgttaaggga    6300
ttttggtcat gagattatca aaaaggatct tcacctagat ccttttaaat taaaaatgaa    6360
gttttaaatc aatctaaagt atatatgagt aaacttggtc tgacagttac caatgcttaa    6420
tcagtgaggc acctatctca gcgatctgtc tatttcgttc atccatagtt gcctgactcc    6480
ccgtcgtgta gataactacg atacgggagg gcttaccatc tggccccagt gctgcaatga    6540
taccgcgaga cccacgctca ccggctccag atttatcagc aataaaccag ccagccggaa    6600
gggccgagcg cagaagtggt cctgcaactt tatccgcctc catccagtct attaattgtt    6660
gccgggaagc tagagtaagt agttcgccag ttaatagttt gcgcaacgtt gttgccattg    6720
ctacaggcat cgtggtgtca cgctcgtcgt ttggtatggc ttcattcagc tccggttccc    6780
aacgatcaag gcgagttaca tgatccccca tgttgtgcaa aaaagcggtt agctccttcg    6840
```

-continued

| | | | | |
|---|---|---|---|---|
| gtcctccgat | cgttgtcaga | agtaagttgg | ccgcagtgtt | atcactcatg | gttatggcag | 6900 |
| cactgcataa | ttctcttact | gtcatgccat | ccgtaagatg | cttttctgtg | actggtgagt | 6960 |
| actcaaccaa | gtcattctga | gaatagtgta | tgcggcgacc | gagttgctct | tgcccggcgt | 7020 |
| caatacggga | taataccgcg | ccacatagca | gaactttaaa | agtgctcatc | attggaaaac | 7080 |
| gttcttcggg | gcgaaaactc | tcaaggatct | taccgctgtt | gagatccagt | tcgatgtaac | 7140 |
| ccactcgtgc | acccaactga | tcttcagcat | cttttacttt | caccagcgtt | tctgggtgag | 7200 |
| caaaaacagg | aaggcaaaat | gccgcaaaaa | agggaataag | ggcgacacgg | aaatgttgaa | 7260 |
| tactcatact | cttcctttttt | caatattatt | gaagcattta | tcagggttat | tgtctcatga | 7320 |
| gcggatacat | atttgaatgt | atttagaaaa | ataaacaaat | aggggttccg | cgcacatttc | 7380 |
| cccgaaaagt | gccacctgac | gtc | | | | 7403 |

<210> SEQ ID NO 2
<211> LENGTH: 7403
<212> TYPE: DNA
<213> ORGANISM: Artificial
<220> FEATURE:
<223> OTHER INFORMATION: G alpha i1-91Rluc

<400> SEQUENCE: 2

| | | | | |
|---|---|---|---|---|
| gacggatcgg | gagatctccc | gatccccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaactt | aagcttggta | ccaccatggg | ctgcacgctg | agcgccgagg | acaaggcggc | 960 |
| ggtggagcgg | agtaagatga | tcgaccgcaa | cctccgtgag | gacggcgaga | aggcggcgcg | 1020 |
| cgaggtcaag | ctgctgctgc | tcggtgctgg | tgaatctggt | aaaagtacaa | ttgtgaagca | 1080 |
| gatgaaaatt | atccatgaag | ctggttattc | agaagaggag | tgtaaacaat | acaaagcagt | 1140 |
| ggtctacagt | aacaccatcc | agtcaattat | tgctatcatt | agggctatgg | ggaggttgtc | 1200 |
| tggtggtggt | ggatccatga | ccagcaaggt | gtacgacccc | gagcagagga | agaggatgat | 1260 |
| caccggcccc | cagtggtggg | ccaggtgcaa | gcagatgaac | gtgctggaca | gcttcatcaa | 1320 |
| ctactacgac | agcgagaagc | acgccgagaa | cgccgtgatc | ttcctgcacg | gcaacgccgc | 1380 |
| tagcagctac | ctgtggaggc | acgtggtgcc | ccacatcgag | cccgtggcca | ggtgcatcat | 1440 |
| ccccgatctg | atcggcatgg | gcaagagcgg | caagagcggc | aacggcagct | acaggctgct | 1500 |

-continued

```
ggaccactac aagtacctga ccgcctggtt cgagctcctg aacctgccca agaagatcat    1560
cttcgtgggc cacgactggg gcgcctgcct ggccttccac tacagctacg agcaccagga    1620
caagatcaag gccatcgtgc acgccgagag cgtggtggac gtgatcgaga gctgggacga    1680
gtggccagac atcgaggagg acatcgccct gatcaagagc gaggagggcg agaagatggt    1740
gctggagaac aacttcttcg tggagaccat gctgcccagc aagatcatga aaagctgga    1800 gcccgaggag ttcgccgcct acctggagcc cttcaaggag aagggcgagg tgagaagacc    1860
caccctgagc tggcccagag agatccccct ggtgaagggc ggcaagcccg acgtggtgca    1920
gatcgtgaga aactcaaacg cctacctgag agccagcgac gacctgccca agatgttcat    1980
cgagagcgac cccggcttct tcagcaacgc catcgtggag ggcgccaaga agttccccaa    2040
caccgagttc gtgaaggtga agggcctgca cttcagccag gaggacgccc ccgacgagat    2100
gggcaagtac atcaagagct cgtggagag agtgctgaaa aacgagcagt ctggtggtgg    2160
tggatccaag atagactttg gtgactcagc ccggcggat gatgcacgcc aactctttgt    2220
gctagctgga gctgctgaag aaggctttat gactgcagaa cttgctggag ttataaagag    2280
attgtggaaa gatagtggtg tacaagcctg tttcaacaga tcccgagagt accagcttaa    2340
tgattctgca gcatactatt tgaatgactt ggacagaata gctcaaccaa attacatccc    2400
gactcaacaa gatgttctca gaactagagt gaaaactaca ggaattgttg aaacccattt    2460
tactttcaaa gatcttcatt ttaaaatgtt tgatgtggga ggtcagagat ctgagcggaa    2520
gaagtggatt cattgcttcg aaggagtgac ggcgatcatc ttctgtgtag cactgagtga    2580
ctacgacctg gttctagctg aagatgaaga aatgaaccga atgcatgaaa gcatgaaatt    2640
gtttgacagc atatgtaaca acaagtggtt tacagataca tccattatac ttttctaaa    2700 caagaaggat ctctttgaag aaaaaatcaa aaagagccct ctcactatat gctatccaga    2760
atatgcagga tcaaacacat atgaagaggc agctgcatat attcaatgtc agtttgaaga    2820
cctcaataaa agaaaggaca caaaggaaat atacacccac ttcacatgtg ccacagatac    2880
taagaatgtg cagtttgttt ttgatgctgt aacagatgtc atcataaaaa ataatctaaa    2940
agattgtggt ctcttttaac tcgagtctag agggcccgtt taaacccgct gatcagcctc    3000
gactgtgcct tctagttgcc agccatctgt tgtttgcccc tcccccgtgc cttccttgac    3060
cctggaaggt gccactccca ctgtcctttc ctaataaaat gaggaaattg catcgcattg    3120
tctgagtagg tgtcattcta ttctgggggg tggggtgggg caggacagca agggggagga    3180
ttgggaagac aatagcaggc atgctgggga tgcggtgggc tctatggctt ctgaggcgga    3240
aagaaccagc tggggctcta gggggtatcc ccacgcgccc tgtagcggcg cattaagcgc    3300
ggcgggtgtg gtggttacgc gcagcgtgac cgctacactt gccagcgccc tagcgcccgc    3360
tcctttcgct ttcttccctt cctttctcgc cacgttcgcc ggctttcccc gtcaagctct    3420
aaatcggggg ctcccttag ggttccgatt tagtgcttta cggcacctcg accccaaaaa    3480
acttgattag ggtgatggtt cacgtagtgg gccatcgccc tgatagacgg ttttcgccc    3540 tttgacgttg gagtccacgt tctttaatag tggactcttg ttccaaactg gaacaacact    3600
caaccctatc tcggtctatt cttttgattt ataagggatt ttgccgattt cggcctattg    3660
gttaaaaaat gagctgattt aacaaaaatt taacgcgaat taattctgtg aatgtgtgt    3720 cagttagggt gtggaaagtc cccaggctcc ccagcaggca gaagtatgca aagcatgcat    3780
ctcaattagt cagcaaccag gtgtggaaag tccccaggct ccccagcagg cagaagtatg    3840
caaagcatgc atctcaatta gtcagcaacc atagtcccgc ccctaactcc gcccatcccg    3900
```

```
cccctaactc cgcccagttc cgcccattct ccgccccatg gctgactaat ttttttttatt    3960 tatgcagagg ccgaggccgc ctctgcctct gagctattcc agaagtagtg aggaggcttt    4020
tttggaggcc taggcttttg caaaaagctc ccgggagctt gtatatccat tttcggatct    4080
gatcaagaga caggatgagg atcgtttcgc atgattgaac aagatggatt gcacgcaggt    4140
tctccggccg cttgggtgga gaggctattc ggctatgact gggcacaaca gacaatcggc    4200
tgctctgatg ccgccgtgtt ccggctgtca gcgcaggggc gcccggttct ttttgtcaag    4260
accgacctgt ccggtgccct gaatgaactg caggacgagg cagcgcggct atcgtggctg    4320
gccacgacgg gcgttccttg cgcagctgtg ctcgacgttg tcactgaagc gggaagggac    4380
tggctgctat tgggcgaagt gccggggcag gatctcctgt catctcacct tgctcctgcc    4440
gagaaagtat ccatcatggc tgatgcaatg cggcggctgc atacgcttga tccggctacc    4500
tgcccattcg accaccaagc gaaacatcgc atcgagcgag cacgtactcg gatggaagcc    4560
ggtcttgtcg atcaggatga tctggacgaa gagcatcagg ggctcgcgcc agccgaactg    4620
ttcgccaggc tcaaggcgcg catgcccgac ggcgaggatc tcgtcgtgac ccatggcgat    4680
gcctgcttgc cgaatatcat ggtggaaaat ggccgctttt ctggattcat cgactgtggc    4740
cggctgggtg tggcggaccg ctatcaggac atagcgttgg ctacccgtga tattgctgaa    4800
gagcttggcg gcgaatgggc tgaccgcttc ctcgtgcttt acggtatcgc cgctcccgat    4860
tcgcagcgca tcgccttcta tcgccttctt gacgagttct tctgagcggg actctggggt    4920
tcgaaatgac cgaccaagcg acgcccaacc tgccatcacg agatttcgat tccaccgccg    4980
ccttctatga aaggttgggc ttcggaatcg ttttccggga cgccggctgg atgatcctcc    5040
agcgcgggga tctcatgctg gagttcttcg cccaccccaa cttgtttatt gcagcttata    5100
atggttacaa ataaagcaat agcatcacaa atttcacaaa taaagcattt ttttcactgc    5160
attctagttg tggtttgtcc aaactcatca atgtatctta tcatgtctgt ataccgtcga    5220
cctctagcta gagcttggcg taatcatggt catagctgtt cctgtgtga aattgttatc    5280 cgctcacaat tccacacaac atacgagccg gaagcataaa gtgtaaagcc tggggtgcct    5340
aatgagtgag ctaactcaca ttaattgcgt tgcgctcact gcccgctttc cagtcgggaa    5400
acctgtcgtg ccagctgcat taatgaatcg gccaacgcgc ggggagaggc ggtttgcgta    5460
ttgggcgctc ttccgcttcc tcgctcactg actcgctgcg ctcggtcgtt cggctgcggc    5520
gagcggtatc agctcactca aaggcggtaa tacggttatc cacagaatca ggggataacg    5580
caggaaagaa catgtgagca aaaggccagc aaaaggccag gaaccgtaaa aaggccgcgt    5640
tgctggcgtt tttccatagg ctccgccccc ctgacgagca tcacaaaaat cgacgctcaa    5700
gtcagaggtg gcgaaacccg acaggactat aaagatacca ggcgtttccc cctggaagct    5760
ccctcgtgcg ctctcctgtt ccgaccctgc cgcttaccgg atacctgtcc gcctttctcc    5820
cttcgggaag cgtggcgctt tctcatagct cacgctgtag gtatctcagt tcggtgtagg    5880
tcgttcgctc caagctgggc tgtgtgcacg aaccccccgt tcagcccgac cgctgcgcct    5940
tatccggtaa ctatcgtctt gagtccaacc cggtaagaca cgacttatcg ccactggcag    6000
cagccactgg taacaggatt agcagagcga ggtatgtagg cggtgctaca gagttcttga    6060
agtggtggcc taactacggc tacactagaa gaacagtatt tggtatctgc gctctgctga    6120
agccagttac cttcggaaaa agagttggta gctcttgatc cggcaaacaa accaccgctg    6180
gtagcggttt ttttgtttgc aagcagcaga ttacgcgcag aaaaaaagga tctcaagaag    6240
atcctttgat cttttctacg gggtctgacg ctcagtggaa cgaaaactca cgttaaggga    6300
```

-continued

| | | |
|---|---|---|
| ttttggtcat gagattatca aaaggatct tcacctagat cctttaaat taaaaatgaa | 6360 | |
| gttttaaatc aatctaaagt atatatgagt aaacttggtc tgacagttac caatgcttaa | 6420 | |
| tcagtgaggc acctatctca gcgatctgtc tatttcgttc atccatagtt gcctgactcc | 6480 | |
| ccgtcgtgta gataactacg atacgggagg gcttaccatc tggccccagt gctgcaatga | 6540 | |
| taccgcgaga cccacgctca ccggctccag atttatcagc aataaaccag ccagccggaa | 6600 | |
| gggccgagcg cagaagtggt cctgcaactt tatccgcctc catccagtct attaattgtt | 6660 | |
| gccgggaagc tagagtaagt agttcgccag ttaatagttt gcgcaacgtt gttgccattg | 6720 | |
| ctacaggcat cgtggtgtca cgctcgtcgt ttggtatggc ttcattcagc tccggttccc | 6780 | |
| aacgatcaag gcgagttaca tgatccccca tgttgtgcaa aaaagcggtt agctccttcg | 6840 | |
| gtcctccgat cgttgtcaga agtaagttgg ccgcagtgtt atcactcatg gttatggcag | 6900 | |
| cactgcataa ttctcttact gtcatgccat ccgtaagatg cttttctgtg actggtgagt | 6960 | |
| actcaaccaa gtcattctga gaatagtgta tgcggcgacc gagttgctct tgcccggcgt | 7020 | |
| caatacggga taataccgcg ccacatagca gaactttaaa agtgctcatc attggaaaac | 7080 | |
| gttcttcggg gcgaaaactc tcaaggatct taccgctgtt gagatccagt tcgatgtaac | 7140 | |
| ccactcgtgc acccaactga tcttcagcat cttttacttt caccagcgtt tctgggtgag | 7200 | |
| caaaaacagg aaggcaaaat gccgcaaaaa agggaataag ggcgacacgg aaatgttgaa | 7260 | |
| tactcatact cttcctttt caatattatt gaagcattta tcagggttat tgtctcatga | 7320 | |
| gcggatacat atttgaatgt atttagaaaa ataaacaaat aggggttccg cgcacatttc | 7380 | |
| cccgaaaagt gccacctgac gtc | 7403 | |

<210> SEQ ID NO 3
<211> LENGTH: 7403
<212> TYPE: DNA
<213> ORGANISM: Artificial
<220> FEATURE:
<223> OTHER INFORMATION: G alpha i1-122Rluc

<400> SEQUENCE: 3

| | | |
|---|---|---|
| gacggatcgg gagatctccc gatccctat ggtgcactct cagtacaatc tgctctgatg | 60 | |
| ccgcatagtt aagccagtat ctgctccctg cttgtgtgtt ggaggtcgct gagtagtgcg | 120 | |
| cgagcaaaat ttaagctaca acaaggcaag gcttgaccga caattgcatg aagaatctgc | 180 | |
| ttagggttag gcgttttgcg ctgcttcgcg atgtacgggc cagatatacg cgttgacatt | 240 | |
| gattattgac tagttattaa tagtaatcaa ttacggggtc attagttcat agcccatata | 300 | |
| tggagttccg cgttacataa cttacggtaa atggcccgcc tggctgaccg cccaacgacc | 360 | |
| cccgcccatt gacgtcaata atgacgtatg ttcccatagt aacgccaata gggactttcc | 420 | |
| attgacgtca atgggtggag tatttacggt aaactgccca cttggcagta catcaagtgt | 480 | |
| atcatatgcc aagtacgccc cctattgacg tcaatgacgg taaatggccc gcctggcatt | 540 | |
| atgcccagta catgacctta tgggactttc ctacttggca gtacatctac gtattagtca | 600 | |
| tcgctattac catggtgatg cggttttggc agtacatcaa tgggcgtgga tagcggtttg | 660 | |
| actcacgggg atttccaagt ctccacccca ttgacgtcaa tgggagtttg ttttggcacc | 720 | |
| aaaatcaacg ggactttcca aaatgtcgta acaactccgc cccattgacg caaatgggcg | 780 | |
| gtaggcgtgt acggtgggag gtctatataa gcagagctct ctggctaact agagaaccca | 840 | |
| ctgcttactg gcttatcgaa attaatacga ctcactatag ggagacccaa gctggctagc | 900 | |
| gtttaaactt aagcttggta ccaccatggg ctgcacgctg agcgccgagg acaaggcggc | 960 | |

-continued

```
ggtggagcgg agtaagatga tcgaccgcaa cctccgtgag gacggcgaga aggcggcgcg   1020
cgaggtcaag ctgctgctgc tcggtgctgg tgaatctggt aaaagtacaa ttgtgaagca   1080
gatgaaaatt atccatgaag ctggttattc agaagaggag tgtaaacaat acaaagcagt   1140
ggtctacagt aacaccatcc agtcaattat tgctatcatt agggctatgg ggaggttgaa   1200
gatagacttt ggtgactcag cccgggcgga tgatgcacgc caactctttg tgctagctgg   1260
agctgctgaa gaaggcttta tgactgcaga atctggtggt ggtggatcca tgaccagcaa   1320
ggtgtacgac cccgagcaga ggaagaggat gatcaccggc ccccagtggt gggccaggtg   1380
caagcagatg aacgtgctgg acagcttcat caactactac gacagcgaga agcacgccga   1440
gaacgccgtg atcttcctgc acggcaacgc cgctagcagc tacctgtgga ggcacgtggt   1500
gccccacatc gagcccgtgg ccaggtgcat catccccgat ctgatcggca tgggcaagag   1560
cggcaagagc ggcaacggca gctacaggct gctggaccac tacaagtacc tgaccgcctg   1620
gttcgagctc ctgaacctgc ccaagaagat catcttcgtg ggccacgact ggggcgcctg   1680
cctggccttc cactacagct acgagcacca ggacaagatc aaggccatcg tgcacgccga   1740
gagcgtggtg gacgtgatcg agagctggga cgagtggcca gacatcgagg aggacatcgc   1800
cctgatcaag agcgaggagg cgagaagat ggtgctggag aacaacttct cgtggagac   1860
catgctgccc agcaagatca tgagaaagct ggagcccgag gagttcgccc cctacctgga   1920
gcccttcaag gagaagggcg aggtgagaag acccaccctg agctggccca gagagatccc   1980
cctggtgaag ggcggcaagc ccgacgtggt gcagatcgtg agaaactaca acgcctacct   2040
gagagccagc gacgacctgc ccaagatgtt catcgagagc gaccccggct cttcagcaa   2100
cgccatcgtg gagggcgcca agaagttccc caacaccgag ttcgtgaagg tgaagggcct   2160
gcacttcagc caggaggacg cccccgacga gatgggcaag tacatcaaga gcttcgtgga   2220
gagagtgctg aagaacgagc agtctggtgg tggtggatcc cttgctggag ttataaagag   2280
attgtggaaa gatagtggtg tacaagcctg tttcaacaga tcccgagagt accagcttaa   2340
tgattctgca gcatactatt tgaatgactt ggacagaata gctcaaccaa attacatccc   2400
gactcaacaa gatgttctca gaactagagt gaaaactaca ggaattgttg aaacccattt   2460
tactttcaaa gatcttcatt ttaaaatgtt tgatgtggga ggtcagagat ctgagcggaa   2520
gaagtggatt cattgcttcg aaggagtgac ggcgatcatc ttctgtgtag cactgagtga   2580
ctacgacctg gttctagctg aagatgaaga aatgaaccga atgcatgaaa gcatgaaatt   2640
gtttgacagc atatgtaaca acaagtggtt tacagataca tccattatac tttttctaaa   2700
caagaaggat ctctttgaag aaaaaatcaa aaagagccct ctcactatat gctatccaga   2760
atatgcagga tcaaacacat atgaagaggc agctgcatat attcaatgtc agtttgaaga   2820
cctcaataaa agaaaggaca caaggaaat atacacccac ttcacatgtg ccacagatac   2880
taagaatgtg cagtttgttt ttgatgctgt aacagatgtc atcataaaaa ataatctaaa   2940
agattgtggt ctctttaac tcgagtctag agggcccgtt taaacccgct gatcagcctc   3000
gactgtgcct tctagttgcc agccatctgt tgtttgcccc tcccccgtgc cttccttgac   3060
cctggaaggt gccactccca ctgtcctttc ctaataaaat gaggaaattg catcgcattg   3120
tctgagtagg tgtcattcta ttctgggggg tggggtgggg caggacagca aggggggagga   3180
ttgggaagac aatagcaggc atgctgggga tgcggtgggc tctatggctt ctgaggcgga   3240
aagaaccagc tggggctcta gggggtatcc ccacgcgccc tgtagcggcg cattaagcgc   3300
ggcgggtgtg gtggttacgc gcagcgtgac cgctacactt gccagcgccc tagcgcccgc   3360
```

```
tcctttcgct ttcttcccct cctttctcgc cacgttcgcc ggctttcccc gtcaagctct    3420
aaatcggggg ctcccttag ggttccgatt tagtgcttta cggcacctcg accccaaaaa    3480
acttgattag ggtgatggtt cacgtagtgg gccatcgccc tgatagacgg ttttcgccc    3540 tttgacgttg gagtccacgt tctttaatag tggactcttg ttccaaactg gaacaacact    3600
caaccctatc tcggtctatt cttttgattt ataagggatt ttgccgattt cggcctattg    3660
gttaaaaaat gagctgattt aacaaaaatt taacgcgaat taattctgtg gaatgtgtgt    3720
cagttagggt gtggaaagtc cccaggctcc ccagcaggca gaagtatgca aagcatgcat    3780
ctcaattagt cagcaaccag gtgtggaaag tccccaggct ccccagcagg cagaagtatg    3840
caaagcatgc atctcaatta gtcagcaacc atagtcccgc ccctaactcc gcccatcccg    3900
cccctaactc cgcccagttc cgcccattct ccgccccatg gctgactaat ttttttatt    3960 tatgcagagg ccgaggccgc ctctgcctct gagctattcc agaagtagtg aggaggcttt    4020
tttggaggcc taggctttg caaaaagctc ccgggagctt gtatatccat tttcggatct    4080
gatcaagaga caggatgagg atcgtttcgc atgattgaac aagatggatt gcacgcaggt    4140
tctccggccg cttgggtgga gaggctattc ggctatgact gggcacaaca gacaatcggc    4200
tgctctgatg ccgccgtgtt ccggctgtca gcgcaggggc gcccggttct ttttgtcaag    4260
accgacctgt ccggtgccct gaatgaactg caggacgagg cagcgcggct atcgtggctg    4320
gccacgacgg gcgttccttg cgcagctgtg ctcgacgttg tcactgaagc gggaagggac    4380
tggctgctat tgggcgaagt gccggggcag gatctcctgt catctcacct tgctcctgcc    4440
gagaaagtat ccatcatggc tgatgcaatg cggcggctgc atacgcttga tccggctacc    4500
tgcccattcg accaccaagc gaaacatcgc atcgagcgag cacgtactcg gatggaagcc    4560
ggtcttgtcg atcaggatga tctggacgaa gagcatcagg ggctcgcgcc agccgaactg    4620
ttcgccaggc tcaaggcgcg catgcccgac ggcgaggatc tcgtcgtgac ccatggcgat    4680
gcctgcttgc cgaatatcat ggtggaaaat ggccgctttt ctggattcat cgactgtggc    4740
cggctgggtg tggcggaccg ctatcaggac atagcgttgg ctacccgtga tattgctgaa    4800
gagcttggcg gcgaatgggc tgaccgcttc ctcgtgcttt acggtatcgc cgctcccgat    4860
tcgcagcgca tcgccttcta tcgccttctt gacgagttct tctgagcggg actctggggt    4920
tcgaaatgac cgaccaagcg acgcccaacc tgccatcacg agatttcgat tccaccgccg    4980
ccttctatga aaggttgggc ttcggaatcg ttttccggga cgccggctgg atgatcctcc    5040
agcgcgggga tctcatgctg gagttcttcg cccacccca cttgtttatt gcagcttata    5100
atggttacaa ataaagcaat agcatcacaa atttcacaaa taaagcattt ttttcactgc    5160
attctagttg tggtttgtcc aaactcatca atgtatctta tcatgtctgt ataccgtcga    5220
cctctagcta gagcttggcg taatcatggt catagctgtt tcctgtgtga aattgttatc    5280
cgctcacaat tccacacaac atacgagccg gaagcataaa gtgtaaagcc tggggtgcct    5340
aatgagtgag ctaactcaca ttaattgcgt tgcgctcact gcccgctttc cagtcggaa     5400 acctgtcgtg ccagctgcat taatgaatcg gccaacgcgc ggggagaggc ggtttgcgta    5460
ttgggcgctc ttccgcttcc tcgctcactg actcgctgcg ctcggtcgtt cggctgcggc    5520
gagcggtatc agctcactca aaggcggtaa tacggttatc cacagaatca ggggataacg    5580
caggaaagaa catgtgagca aaaggccagc aaaaggccag gaaccgtaaa aaggccgcgt    5640
tgctggcgtt tttccatagg ctccgccccc ctgacgagca tcacaaaaat cgacgctcaa    5700
gtcagaggtg gcgaaacccg acaggactat aaagatacca ggcgtttccc cctggaagct    5760
```

```
ccctcgtgcg ctctcctgtt ccgaccctgc cgcttaccgg atacctgtcc gcctttctcc    5820
cttcgggaag cgtggcgctt tctcatagct cacgctgtag gtatctcagt tcggtgtagg    5880
tcgttcgctc caagctgggc tgtgtgcacg aaccccccgt tcagcccgac cgctgcgcct    5940
tatccggtaa ctatcgtctt gagtccaacc cggtaagaca cgacttatcg ccactggcag    6000
cagccactgg taacaggatt agcagagcga ggtatgtagg cggtgctaca gagttcttga    6060
agtggtggcc taactacggc tacactagaa gaacagtatt tggtatctgc gctctgctga    6120
agccagttac cttcggaaaa agagttggta gctcttgatc cggcaaacaa accaccgctg    6180
gtagcggttt ttttgtttgc aagcagcaga ttacgcgcag aaaaaaagga tctcaagaag    6240
atcctttgat cttttctacg gggtctgacg ctcagtggaa cgaaaactca cgttaaggga    6300
ttttggtcat gagattatca aaaaggatct tcacctagat ccttttaaat taaaaatgaa    6360
gttttaaatc aatctaaagt atatatgagt aaacttggtc tgacagttac caatgcttaa    6420
tcagtgaggc acctatctca gcgatctgtc tatttcgttc atccatagtt gcctgactcc    6480
ccgtcgtgta gataactacg atacgggagg gcttaccatc tggccccagt gctgcaatga    6540
taccgcgaga cccacgctca ccggctccag atttatcagc aataaaccag ccagccggaa    6600
gggccgagcg cagaagtggt cctgcaactt tatccgcctc catccagtct attaattgtt    6660
gccgggaagc tagagtaagt agttcgccag ttaatagttt gcgcaacgtt gttgccattg    6720
ctacaggcat cgtggtgtca cgctcgtcgt ttggtatggc ttcattcagc tccggttccc    6780
aacgatcaag gcgagttaca tgatccccca tgttgtgcaa aaaagcggtt agctccttcg    6840
gtcctccgat cgttgtcaga agtaagttgg ccgcagtgtt atcactcatg gttatggcag    6900
cactgcataa ttctcttact gtcatgccat ccgtaagatg cttttctgtg actggtgagt    6960
actcaaccaa gtcattctga gaatagtgta tgcggcgacc gagttgctct tgcccggcgt    7020
caatacggga taataccgcg ccacatagca gaactttaaa agtgctcatc attggaaaac    7080
gttcttcggg gcgaaaactc tcaaggatct taccgctgtt gagatccagt tcgatgtaac    7140
ccactcgtgc acccaactga tcttcagcat cttttacttt caccagcgtt tctgggtgag    7200
caaaaacagg aaggcaaaat gccgcaaaaa agggaataag ggcgacacgg aaatgttgaa    7260
tactcatact cttccttttt caatattatt gaagcattta tcagggttat tgtctcatga    7320
gcggatacat atttgaatgt atttagaaaa ataaacaaat aggggttccg cgcacatttc    7380
cccgaaaagt gccacctgac gtc                                            7403
```

<210> SEQ ID NO 4
<211> LENGTH: 6
<212> TYPE: PRT
<213> ORGANISM: Artificial Sequence
<220> FEATURE:
<223> OTHER INFORMATION: peptide linker

<400> SEQUENCE: 4

Ser Gly Gly Gly Gly Ser